US011623931B2

(12) United States Patent
Molette et al.

(10) Patent No.: US 11,623,931 B2
(45) Date of Patent: Apr. 11, 2023

(54) BICYCLIC COMPOUNDS FOR DIAGNOSIS AND THERAPY

(71) Applicant: AC IMMUNE SA, Lausanne (CH)

(72) Inventors: Jérôme Molette, Prevessin Moens (FR); Emanuele Gabellieri, Lausanne (CH); Vincent Darmency, Bougy-Villars (CH)

(73) Assignee: AC IMMUNE SA, Lausanne (CH)

( * ) Notice: Subject to any disclaimer, the term of this patent is extended or adjusted under 35 U.S.C. 154(b) by 0 days.

(21) Appl. No.: 16/894,682

(22) Filed: Jun. 5, 2020

(65) Prior Publication Data

US 2020/0299305 A1 Sep. 24, 2020

Related U.S. Application Data

(62) Division of application No. 16/084,223, filed as application No. PCT/EP2017/055754 on Mar. 10, 2017, now abandoned.

(30) Foreign Application Priority Data

Mar. 11, 2016 (EP) .................................... 16159878
Nov. 18, 2016 (EP) .................................... 16199577

(51) Int. Cl.

| | |
|---|---|
| *C07D 495/04* | (2006.01) |
| *C07D 417/14* | (2006.01) |
| *C07D 513/04* | (2006.01) |
| *A61K 51/04* | (2006.01) |
| *C07B 59/00* | (2006.01) |

(52) U.S. Cl.

CPC ........ *C07D 495/04* (2013.01); *A61K 51/0431* (2013.01); *C07B 59/002* (2013.01); *C07D 417/14* (2013.01); *C07D 513/04* (2013.01); *C07B 2200/05* (2013.01)

(58) Field of Classification Search

CPC .... A61K 51/04; C07D 495/04; C07D 417/14; C07D 513/04

See application file for complete search history.

(56) References Cited

FOREIGN PATENT DOCUMENTS

| | | | |
|---|---|---|---|
| EP | 2377860 | A1 | 10/2011 |
| JP | 2004506723 | A | 3/2004 |
| JP | 2011529086 | A | 12/2011 |
| JP | 2012142510 | A | 7/2012 |
| JP | 2013040945 | A | 2/2013 |
| WO | 2010/071819 | A1 | 6/2010 |
| WO | 2016/087373 | A1 | 6/2016 |
| WO | 2017/069275 | A1 | 4/2017 |

OTHER PUBLICATIONS

"Office Action issued by the Brazilian National Institute of Industrial Property for counterpart application No. BR112018068066-4"' dated Apr. 15, 2021.

"Office Action issued by the Japanese Patent Office (JPO) dated Mar. 2, 2021", for counterpart Japanese Patent Application No. 2018-548003.

Iaroshenko, V. O. et al., 2, 3-Unsubstituted chromenes and their enaminone precursors as versatile reagents for the synthesis of fused pyridines, Organic & Biomolecular Chemistry, 2012, vol. 10, No. 4, pp. 890-894.

Iaroshenko, V. O. et al., Synthesis of thiazolo[4, 5-d]pyridines, Synthesis, 2008, No. 15, pp. 2337-2346.

Krayushkin, M. M. et al., A new approach to condensed pyridines, Mendeleev Communications, 2005, No. 4, pp. 151-152.

AC Immune SA, "Notice of Reasons for Rejection for JP 2021-137179," dated Sep. 26, 2022, 11 pages.

*Primary Examiner* — Michael G. Hartley
*Assistant Examiner* — Jagadishwar R Samala
(74) *Attorney, Agent, or Firm* — F. Brent Nix, Esq.; Johnson, Marcou, Isaacs & Nix, LLC

(57) ABSTRACT

The present invention relates to novel compounds that can be employed in the diagnosis, monitoring of disease progression or monitoring of drug activity, of a group of disorders and abnormalities associated with alpha-synuclein (α-synuclein, A-synuclein, aSynuclein, A-syn, α-syn, aSyn) aggregates including, but not limited to, Lewy bodies and/or Lewy neurites, such as Parkinson's disease. The instant compounds are particularly useful in determining a predisposition to such a disorder, monitoring residual disorder, or predicting the responsiveness of a patient who is suffering from such a disorder to the treatment with a certain medicament. The present compounds can also be used to treat, alleviate or prevent a disorder or abnormality associated with alpha-synuclein aggregates.

10 Claims, No Drawings

BICYCLIC COMPOUNDS FOR DIAGNOSIS AND THERAPY

CROSS-REFERENCE TO RELATED APPLICATIONS

This application is a divisional application of U.S. application Ser. No. 16/084,223, filed Sep. 11, 2018, which is a National Stage application of International Application No. PCT/EP2017/055754, filed Mar. 10, 2017, which claims the benefit of European Patent Application No. 16159878.4 filed Mar. 11, 2016 and European Patent Application No. 16199577.4 filed Nov. 18, 2016. The entire contents of the above-identified applications are hereby fully incorporated herein by reference.

FIELD OF THE INVENTION

The present invention relates to novel compounds that can be employed in the diagnosis, monitoring of disease progression or monitoring of drug activity, of a group of disorders and abnormalities associated with alpha-synuclein (α-synuclein, A-synuclein, aSynuclein, A-syn, α-syn, aSyn) aggregates including, but not limited to, Lewy bodies and/or Lewy neurites, such as Parkinson's disease. The instant compounds are particularly useful in determining a predisposition to such a disorder, monitoring residual disorder, or predicting the responsiveness of a patient who is suffering from such a disorder to the treatment with a certain medicament. The present compounds can also be used to treat, alleviate or prevent a disorder or abnormality associated with alpha-synuclein aggregates.

BACKGROUND OF THE INVENTION

Many diseases of aging are based on or associated with extracellular or intracellular deposits of amyloid or amyloid-like proteins that contribute to the pathogenesis as well as to the progression of the disease. The best characterized amyloid protein that forms extracellular aggregates is amyloid beta (AR).

Amyloid-like proteins, that form mainly intracellular aggregates, include, but are not limited to tau, alpha-synuclein, and huntingtin (htt). Diseases involving alpha-synuclein aggregates are generally listed as synucleinopathies (or α-synucleinopathies) and this includes, but is not limited to, Parkinson's disease (PD). Synucleinopathies include Parkinson's disease (sporadic, familial with alpha-synuclein mutations, familial with mutations other than alpha-synuclein, pure autonomic failure and Lewy body dysphagia), dementia with Lewy bodies ("pure" Lewy body dementia), sporadic Alzheimer's disease, familial Alzheimer's disease with APP mutations, familial Alzheimer's disease with PS-1, PS-2 or other mutations, familial British dementia, Lewy body variant of Alzheimer's disease and normal aging (Down syndrome). Synucleinopathies with neuronal and glial aggregates of alpha synuclein include multiple system atrophy (Shy-Drager syndrome, striatonigral degeneration and olivopontocerebellar atrophy). Other diseases that may have alpha-synuclein-immunoreactive lesions include traumatic brain injury, chronic traumatic encephalopathy, tauopathies (Pick's disease, frontotemporal dementia, progressive supranuclear palsy, corticobasal degeneration and Niemann-Pick type C1 disease), motor neuron disease, amyotrophic lateral sclerosis (sporadic, familial and ALS-dementia complex of Guam), neuroaxonal dystrophy, neurodegeneration with brain iron accumulation type 1 (Hallervorden-Spatz syndrome), prion diseases, ataxia telangiectatica, Meige's syndrome, subacute sclerosing panencephalitis, Gaucher disease as well as other lysosomal storage disorders (including Kufor-Rakeb syndrome and Sanfilippo syndrome) and rapid eye movement (REM) sleep behavior disorder (Jellinger, Mov Disord 2003, 18 Suppl. 6, S2-12; Galvin et al. JAMA Neurology 2001, 58 (2), 186-190; Kovari et al., Acta Neuropathol. 2007, 114(3), 295-8; Saito et al., J Neuropathol Exp Neurol. 2004, 63(4), 323-328; McKee et al., Brain, 2013, 136(Pt 1), 43-64; Puschmann et al., Parkinsonism Relat Disord 2012, 18S1, S24-S27; Usenovic et al., J Neurosci. 2012, 32(12), 4240-4246; Winder-Rhodes et al., Mov Disord. 2012, 27(2), 312-315; Ferman et al., J Int Neuropsychol Soc. 2002, 8(7), 907-914).

Alpha-synuclein is a 140 amino acid natively unfolded protein (Iwai et al., Biochemistry 1995, 34(32), 10139-10145). The sequence of alpha-synuclein can be divided into three main domains: 1) the N-terminal region comprising of residues 1-60, which contains the 11-mer amphipatic imperfect repeat residues with highly conserved hexamer (KTKEGV). This region has been implicated in regulating alpha-synuclein binding to membranes and its internalization; 2) the hydrophobic Non Amyloid beta Component (NAC) domain spanning residues 61-95; which is essential for alpha-synuclein fibrillization; and 3) the C-terminal region spanning residues 96-140 which is highly acidic and proline-rich, has no distinct structural propensity. Alpha-synuclein has been shown to undergo several post translational modifications, including truncations, phosphorylation, ubiquitination, oxidation and/or transglutaminase covalent cross linking (Fujiwara et al., Nat Cell Biol 2002, 4(2); 160-164; Hasegawa et al., J Biol Chem 2002, 277(50), 49071-49076; Li et al., Proc Natl Acad Sci USA 2005, 102(6), 2162-2167; Oueslati et al, Prog Brain Res 2010, 183, 115-145; Schmid et al., J Biol Chem 2009, 284(19), 13128-13142). Interestingly, the majority of these modifications involve residues within the C-terminal region.

Several phosphorylation sites have been detected in the carboxyl-terminal region on Tyr-125, -133, and -136, and on Ser-129 (Negro et al., FASEB J 2002, 16(2), 210-212). Tyr-125 residues can be phosphorylated by two Src family protein tyrosine kinases, c-Src and Fyn (Ellis et al., J Biol Chem 2001, 276(6), 3879-3884; Nakamura et al., Biochem Biophys Res Commun 2001, 280(4), 1085-1092). Phosphorylation by Src family kinases does not suppress or enhance the tendency of alpha-synuclein to polymerize. Alpha-synuclein has proved to be an outstanding substrate for protein tyrosine kinase $p72^{syk}$ (Syk) in vitro; once it is extensively Tyr-phosphorylated by Syk or tyrosine kinases with similar specificity, it loses the ability to form oligomers, suggesting a putative anti-neurodegenerative role for these tyrosine kinases (Negro et al., FASEB J 2002, 16(2), 210-212). Alpha-synuclein can be Ser-phosphorylated by protein kinases CKI and CKII (Okochi et al., J Biol Chem 2000, 275(1), 390-397). The residue Ser-129 is also phosphorylated by G-protein-coupled receptor protein kinases (Pronin et al., J Biol Chem 2000, 275(34), 26515-26522). Extensive and selective phosphorylation of alpha-synuclein at Ser-129 is evident in synucleinopathy lesions, including Lewy bodies (Fujiwara et al., Nat Cell Biol 2002, 4(2); 160-164). Other post-translational modifications in the carboxyl-terminal, including glycosylation on Ser-129 (McLean et al., Neurosci Lett 2002, 323(3), 219-223) and nitration on Tyr-125, -133, and-136 (Takahashi et al., Brain Res 2002, 938(1-2), 73-80), may affect aggregation of alpha-synuclein. Truncation of the carboxyl-terminal region by proteolysis has been reported to play a role in alpha-synuclein fibrillogenesis in various neurodegenerative diseases (Rochet et al., Biochemistry 2000, 39(35), 10619-10626). Full-length as well as partially truncated and insoluble aggregates of alpha-synuclein have been detected in highly purified Lewy bodies (Crowther et al., FEBS Lett 1998, 436(3), 309-312).

Abnormal protein aggregation appears to be a common feature in aging brain and in several neurodegenerative diseases, although a clear role in the disease process remains to be defined. In in vitro models, alpha-synuclein (or some of its truncated forms) readily assembles into filaments resembling those isolated from brain of patients with LB dementia and familiar PD (Crowther et al., FEBS Lett 1998, 436(3), 309-312). Alpha-synuclein and its mutated forms (A53T and A30P) have a random coil conformation and do not form significant secondary structures in aqueous solution at low concentrations; however, at higher concentrations they are prone to self-aggregate, producing amyloid fibrils (Wood et al., J Biol Chem 1999, 274(28), 19509-19512). Several differences in the aggregation behavior of the PD-linked mutants and the wild-type protein have been documented. Monomeric alpha-synuclein aggregates in vitro form stable fibrils via a metastable oligomeric (i.e., protofibril) state (Volles et al., Biochemistry 2002, 41(14), 4595-4602).

Parkinson's disease (PD) is the most common neurodegenerative motor disorder. PD is mainly an idiopathic disease, although in at least 5% of the PD patients the pathology is linked to mutations in one or several specific genes (Lesage et al., Hum. Mol. Genet., 2009, 18, R48-59). The pathogenesis of PD remains elusive, however, growing evidence suggests a role for the pathogenic folding of the alpha-synuclein protein that leads to the formation of amyloid-like fibrils. Indeed, the hallmarks of PD are the presence of intracellular alpha-synuclein aggregate structures called Lewy Bodies in the nigral neurons, as well as the death of dopaminergic neurons in the substantia nigra and elsewhere. Alpha-synuclein is a natively unfolded presynaptic protein that can misfold and aggregate into larger oligomeric and fibrillar forms which are linked to the pathogenesis of PD. Recent studies have implicated small soluble oligomeric and protofibrillar forms of alpha-synuclein as the most neurotoxic species (Lashuel et al., J. Mol. Biol., 2002, 322, 1089-102), however the precise role of alpha-synuclein in the neuronal cell toxicity remains to be clarified (review: Cookson, Annu. Rev. Biochem., 2005, 74, 29-52).

The diagnosis of Parkinson's disease is largely clinical and depends on the presence of a specific set of symptoms and signs (the initial core feature being bradykinesia, rigidity, rest tremor and postural instability), the absence of atypical features, a slowly progressive course, and a response to drug therapy. The diagnosis requires clinical skills but is open to a degree of subjectivity and error, as several other degenerative and non-degenerative diseases can mimic PD (MSA, progressive supranuclear palsy (PSP), AD, essential tremor, dystonic tremor), (Guideline No. 113: Diagnosis and pharmacological management of Parkinson's disease, January 2010. SIGN). The final confirmation of the diagnosis is made by post-mortem neuropathological analysis.

Computed tomography (CT) and conventional magnetic resonance imaging (MRI) brain scans of people with PD usually appear normal. These techniques are nevertheless useful to rule out other diseases that can be secondary causes of parkinsonism, such as basal ganglia tumors, vascular pathology and hydrocephalus. A specific technique of MRI, diffusion MRI, has been reported to be useful at discriminating between typical and atypical parkinsonism, although its exact diagnostic value is still under investigation. Dopaminergic function in the basal ganglia can be measured with different PET and SPECT radiotracers. Examples are ioflupane ($^{123}$I) (trade name DaTSCAN) and iometopane (Dopascan) for SPECT or fluorodeoxyglucose ($^{18}$F) and DTBZ for PET. A pattern of reduced dopaminergic activity in the basal ganglia can aid in diagnosing PD (Brooks, J. Nucl. Med., 2010, 51, 596-609; Redmond, Neuroscientist, 2002, 8, 457-88; Wood, Nat. Rev. Neurol., 2014, 10, 305).

Strategies are being developed to apply recent advances of the cause of Parkinson disease to the development of biochemical biomarkers (Schapira Curr Opin Neurol 2013; 26(4):395-400). Such biomarkers that have been investigated in different body fluids (cerebrospinal fluid (CSF), plasma, saliva) include alpha-synuclein levels but also DJ-1, Tau and Abeta, as well as neurofilaments proteins, interleukins, osteopontin and hypocrontin (Schapira Curr Opin Neurol 2013; 26(4):395-400), but so far none of these biomarkers alone or in combination can be used as determinant diagnostic test. To our knowledge none approved alpha-synuclein agent is currently on the market or available for clinical despite a crucial needs for Parkinson's disease research and drug development (Eberling et al., J Parkinsons Dis. 2013; 3(4):565-7).

The ability to image alpha-synuclein deposition in the brain would be a huge achievement for Parkinson's disease research and drug development. The accumulation of aggregated alpha-Synuclein in the brain is a pathological hallmark of PD and a priority target for drug development given its hypothesized contribution to neurodegeneration. In vivo imaging of alpha-synuclein pathology could be useful as a biomarker of the presence of the disease and disease progression and as a pharmacodynamics tool for drug development. The development of an alpha-Synuclein PET imaging agent is considered as very important for the diagnosis and monitoring the effects of therapeutics targeting alpha-synuclein (Eberling, Dave and Frasier, J. Parkinson's Disease, 3, 565-567 (2013)). Despite a huge effort to identify an alpha-Synuclein PET ligand, so far compounds that bind with reasonably high affinity to artificial alpha-synuclein fibrils were identified but they are not optimal for a number of reasons: low or no affinity to pathological aggregates of alpha-synuclein present in the diseased brains, low or non-selectivity for alpha-synuclein over other aggregated proteins and inappropriate physicochemical properties (Eberling et al., J Parkinsons Dis. 2013; 3(4):565-7; Neal et al., Mol Imaging Biol. 2013; 15:585-595; Bagchi et al., PLoS One 2013; 8(2):e55031; Yu et al., Bioorganic and Medicinal chemistry 2012; 20:4625-4634; Zhang et al., Appl Sci (Basel) 2014; 4(1):66-78; Chu et al., J Med Chem, 2015, 58 (15):6002-17).

In order to achieve high alpha-synuclein selectivity, molecular probes have been used which recognize and bind to the pathological alpha-synuclein. In order to reduce background signal interference resulting from non-specific off-target binding, and to reduce dosing requirements, alpha-synuclein imaging compounds should bind with high affinity and selectivity to their target. For imaging of alpha-synuclein aggregates associated with neurological disorders such as Parkinson's disease, imaging compounds need to penetrate the blood brain barrier and pass into the relevant regions of the brain. For targeting intracellular amyloid-like inclusions such as alpha-synuclein, cell permeability is a further requirement of imaging compounds. A further prerequisite in order to avoid unnecessary accumulation of compound which may result in increased risk of unwanted side-effects, is a fast compound wash-out from the brain (or other targeting organ).

WO 2011/128455 refers to specific compounds which are suitable for treating disorders associated with amyloid proteins or amyloid-like proteins. US 2012/0302755 relates to certain imaging agents for detecting neurological dysfunction. Further compounds for the diagnosis of neurodegenerative disorders on the olfactory epithelium are discussed in WO 2012/037928.

WO 2010/063701 refers to a certain in vivo imaging agent for use in a method to determine the presence of, or susceptibility to, Parkinson's disease, wherein the in vivo imaging agent comprises an α-synuclein binder labelled with an in vivo imaging moiety, and wherein the in vivo imaging agent binds to α-synuclein with a binding affinity.

US 2014/0142089 relates to a method for preventing or treating a degenerative brain disease, the method comprising administering to a subject in need thereof an effective amount of a pharmaceutical composition comprising a specific compound, a pharmaceutically acceptable salt, an isomer, a solvate, a hydrate, and a combination thereof.

WO 2009/155017 describes aryl or heteroaryl substituted azabenzoxazole derivatives, which are stated to be useful as tracers in positron emission tomography (PET) imaging to study amyloid deposits in brain in vivo to allow diagnosis of Alzheimer's disease.

WO 2016/033445 refers to specific compound for imaging huntingtin protein.

SUMMARY OF THE INVENTION

It was an object of the present invention to provide compounds that can be employed in the diagnosis, monitoring of disease progression, monitoring of drug activity, of a disorder or abnormality associated with alpha-synuclein aggregates including, but not limited to, Lewy bodies and/or Lewy neurites, such as Parkinson's disease. In particular, the compounds should be suitable for determining a predisposition to such a disorder, monitoring residual disorder, or predicting the responsiveness of a patient who is suffering from such a disorder to the treatment with a certain medicament.

Furthermore, there exists a need in the art for compounds which can be used as imaging agents for alpha-synuclein aggregates including, but not limited to, Lewy bodies and/or Lewy neurites. In particular, it was an object of the present invention to provide compounds that are suitable as a diagnostic composition for positron emission tomography imaging of synucleinopathies, e.g., wherein the compounds are detectably labeled with $^{18}F$. The present inventors have surprisingly found that these objects can be achieved by the compounds of formulae (I) and (II) as described hereinafter.

In another aspect, it was an object of the present invention to provide compounds that can be employed to treat, alleviate or prevent a disorder or abnormality associated with alpha-synuclein aggregates including, but not limited to, Lewy bodies and/or Lewy neurites, such as Parkinson's disease.

The compounds of formulae (I) and (II) display high binding affinity to different alpha-synuclein aggregates in human tissues. Moreover, the compounds of formulae (I) and (II) display high selectivity for aSyn over Aβ and tau pathological deposits enabling the differentiation of PD from other proteinopathies that share common clinical and pathological features. Due to their unique design features, these compounds display properties such as appropriate lipophilicity and molecular weight, brain uptake and pharmacokinetics, cell permeability, solubility, and autofluorescence in order to be successful imaging probes for detection and quantification of alpha-synuclein aggregates including, but not limited to, Lewy bodies and/or Lewy neurites load in vivo, ex vivo and in vitro.

The present invention discloses novel compounds of formulae (I) and (II) having enhanced binding properties to alpha-synuclein aggregates including, but not limited to, Lewy bodies and/or Lewy neurites. The compounds of this invention may be labeled (e.g., radiolabeled), so that they may be used for ex vivo and in vivo imaging to detect alpha-synuclein aggregates including, but not limited to, Lewy bodies and/or Lewy neurites. The present invention provides methods for the detection of alpha-synuclein aggregates including, but not limited to, Lewy bodies and/or Lewy neurites, ex vivo using a compound of formulae (I) and (II) or a pharmaceutical composition thereof. The present invention provides compounds of formulae (I) and (II) for use as diagnostic imaging agents, particularly for presymptomatic detection of Parkinson's disease and/or other α-synucleinopathies, e.g., using positron emission tomography (PET). The invention would serve as a biomarker for monitoring of topographic progression of pathology, leading to improvement of clinical diagnosis and clinical study design. The present invention further provides a pharmaceutical composition comprising a compound of formula (I) or (II) and a pharmaceutically acceptable carrier or excipient.

The present invention is summarized in the following items:

1. A compound of formula (I):

(I)

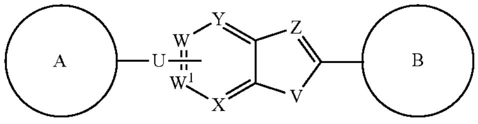

and all detectably labeled derivatives, stereoisomers, racemic mixtures, pharmaceutically acceptable salts, hydrates, solvates, prodrugs and polymorphs thereof; wherein

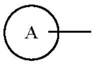

is selected from the group consisting of

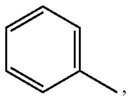, 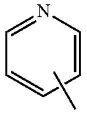, 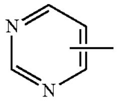, 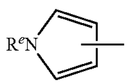,

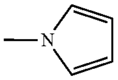, 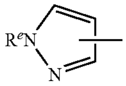, 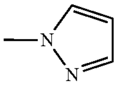, 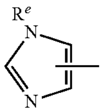,

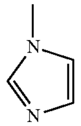, 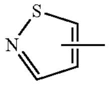, 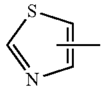, 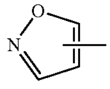,

-continued

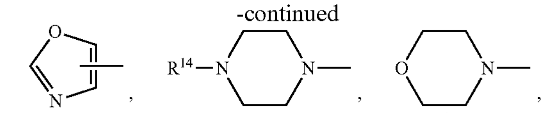

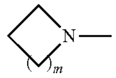 and —CN, wherein 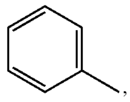,

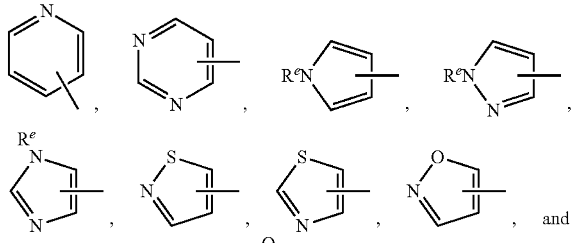

and

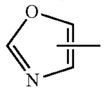

can be attached at any available position to the moiety U, and wherein

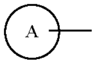

can be optionally substituted by one or more substituents $R^A$;

wherein

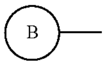

is selected from the group consisting of

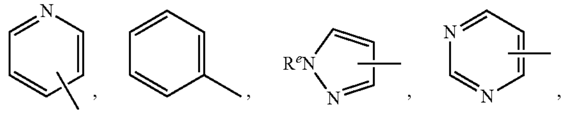

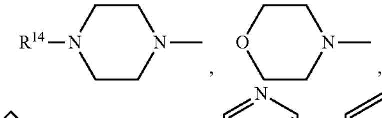

, and

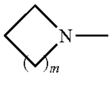, wherein 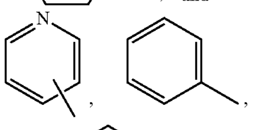,

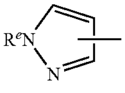, and 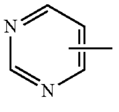

can be attached at any available position, and wherein

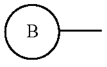

can be optionally substituted by one or more substituents $R^B$;

V is selected from the group consisting of S, $NR^a$ and $CR^bR^b$,

Z is selected from the group consisting of N and $CR^c$,

W is selected from the group consisting of N and $CR^c$ or W is C if W is attached to U;

$W^1$ is selected from the group consisting of N and $CR^c$ or $W^1$ is C if $W^1$ is attached to U;

X is selected from the group consisting of N and $CR^c$ or X is C if X is attached to U;

Y is selected from the group consisting of N and $CR^c$ or Y is C if Y is attached to U;

U is selected from the group consisting of $—NR^a—$, —CH=CH—, —C≡C— and a bond;

for each occurrence, $R^a$ is independently selected from the group consisting of hydrogen, alkyl, and haloalkyl;

for each occurrence, $R^b$ is independently selected from the group consisting of hydrogen, alkyl, haloalkyl, and halogen;

for each occurrence, $R^c$ is independently selected from the group consisting of hydrogen, alkyl, haloalkyl, and halogen;

for each occurrence, $R^d$ is independently selected from the group consisting of halogen, —OH, —O-alkyl and hydrogen;

for each occurrence, $R^e$ is independently selected from the group consisting of hydrogen, $—(CH_2CH_2—O)_n—R^f$, $—(CH_2CH_2—O)_n—(CH_2CH_2)—R^d$, alkyl, carbocyclyl and heterocyclyl, wherein alkyl, carbocyclyl and heterocyclyl can be optionally substituted, for each occurrence, $R^f$ is independently selected from the group consisting of hydrogen, and alkyl, wherein alkyl can be optionally substituted;

for each occurrence, $R^A$ is independently selected from the group consisting of halogen, CN, $—O—R^{10}$, $—NR^{10}R^{11}$, $—CONR^{10}R^{11}$, $—N(R^{10})—C(O)—R^{11}$, $—N(R^{10})—C(O)—O—R^{11}$, $—(O—CH_2CH_2)_n—R^d$, =O, alkyl, carbocyclyl, carbocyclylalkyl, heterocyclyl, heterocyclylalkyl, alkenyl, and alkynyl, wherein alkyl, carbocyclyl, carbocyclylalkyl, heterocyclyl, heterocyclylalkyl, alkenyl, and alkynyl can be optionally substituted, or if more than one group $R^A$ is present and two of the groups $R^A$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted;

for each occurrence, $R^B$ is independently selected from the group consisting of halogen, CN, $—O—R^{10}$, $—NR^{10}R^{11}$, $—CONR^{10}R^{11}$, $—N(R^{10})—C(O)—R^{11}$, $—N(R^{10})—C(O)—O—R^{11}$, $—(O—CH_2CH_2)_n—R^d$, =O, alkyl, carbocyclyl, carbocyclylalkyl, heterocyclyl, heterocyclylalkyl, alkenyl, and alkynyl, wherein alkyl, carbocyclyl, carbocyclylalkyl, heterocyclyl, heterocyclylalkyl, alkenyl, and alkynyl can be optionally substituted, or if more than one group $R^B$ is present and two of the groups $R^B$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted;

for each occurrence, $R^{10}$ is independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{11}$ is independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{14}$ is independently selected from the group consisting of hydrogen, $-(CH_2CH_2-O)_n-R^f$, $-(CH_2CH_2-O)_n-(CH_2CH_2)-R^d$, alkyl, carbocyclyl and heterocyclyl, wherein alkyl, carbocyclyl and heterocyclyl can be optionally substituted;

for each occurrence, n is independently 1 to 4; and for each occurrence, m is independently 1 to 4.

2. The compound according to item 1, which is a compound of the formula (Ia):

(Ia)

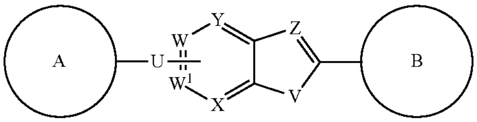

wherein A, U, B, X, Y, W, $W^1$ and Z are as defined in item 1.

3. The compound according to item 1, which is a compound of the formula (Ib) or (Ic):

(Ib)

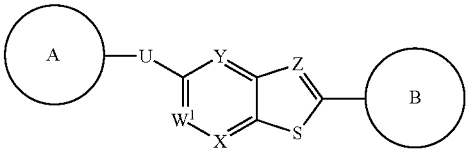

(Ic)

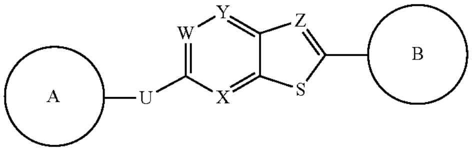

wherein A, U, B, X, Y, W, $W^1$ and Z are as defined in item 1.

4. The compound according to item 1, which is a compound of the formula (Id), (Ie), (If), (Ig), (Ih) or (Ii):

(Id)

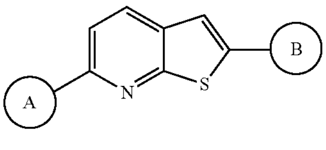

(Ie)

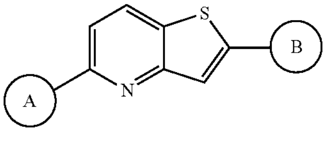

-continued (If)

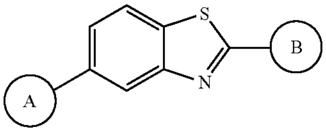

(Ig)

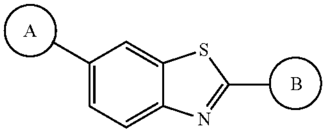

(Ih)

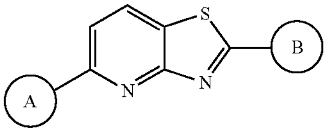

(Ii)

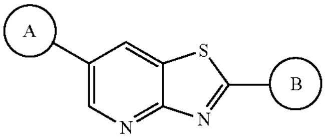

wherein A and B are as defined in item 1.

5. The compound according to any one of items 1 to 4, wherein

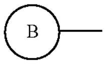

is

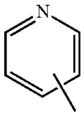, wherein 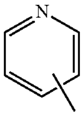, can be attached at any available position, and wherein

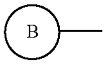

can be optionally substituted by one or more substituents $R^B$.

6. A compound of formula (II):

(II)

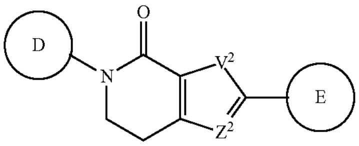

and all detectably labeled derivatives, stereoisomers, racemic mixtures, pharmaceutically acceptable salts, hydrates, solvates, prodrugs and polymorphs thereof;

wherein

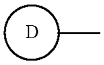

is selected from the group consisting of

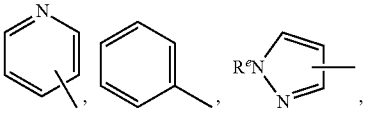

hydrogen and alkyl, wherein

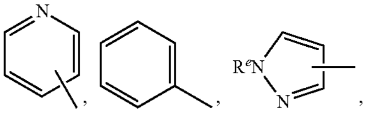

and alkyl can be attached at any available position, and wherein

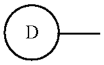

can be optionally substituted by one or more substituents $R^D$; wherein

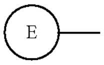

is selected from the group consisting of

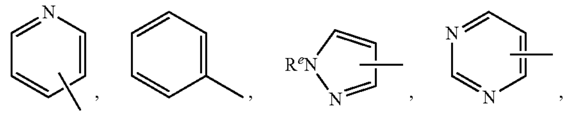

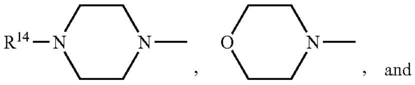

, and

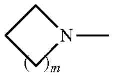

, wherein

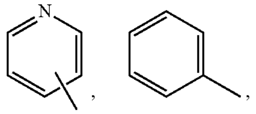

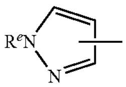

, and

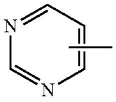

can be attached at any available position, and wherein

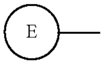

can be optionally substituted by one or more substituents $R^E$;

$V^2$ is selected from the group consisting of S, $NR^a$ and $CR^bR^b$, $Z^2$ is selected from the group consisting of N and $CR^c$, for each occurrence, $R^a$ is independently selected from the group consisting of hydrogen, alkyl, and haloalkyl;

for each occurrence, $R^b$ is independently selected from the group consisting of hydrogen, alkyl, haloalkyl, and halogen;

for each occurrence, $R^c$ is independently selected from the group consisting of hydrogen, alkyl, haloalkyl, and halogen;

for each occurrence, $R^d$ is independently selected from the group consisting of halogen, —OH, —O-alkyl and hydrogen;

for each occurrence, $R^e$ is independently selected from the group consisting of hydrogen, $—(CH_2CH_2—O)_n—R^f$, $—(CH_2CH_2—O)_n—(CH_2CH_2)—R^d$, alkyl, carbocyclyl and heterocyclyl, wherein alkyl, carbocyclyl and heterocyclyl can be optionally substituted, for each occurrence, $R^f$ is independently selected from the group consisting of hydrogen, and alkyl, wherein alkyl can be optionally substituted;

for each occurrence, $R^D$ is independently selected from the group consisting of halogen, CN, $—O—R^{10}$, $—NR^{10}R^{11}$, $—CONR^{10}R^{11}$, $—N(R^{10})—C(O)—R^{11}$, $—N(R^{10})—C(O)—O—R^{11}$, $—(O—CH_2CH_2)_n—R^d$, =O, alkyl, carbocyclyl, carbocyclylalkyl, heterocyclyl, heterocyclylalkyl, alkenyl, and alkynyl, wherein alkyl, carbocyclyl, carbocyclylalkyl, heterocyclyl, heterocyclylalkyl, alkenyl, and alkynyl can be optionally substituted, or if more than one group $R^D$ is present and two of the groups $R^D$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted;

for each occurrence, $R^E$ is independently selected from the group consisting of halogen, CN, $—O—R^{10}$, $—NR^{10}R^{11}$, $—CONR^{10}R^{11}$, $—N(R^{10})—C(O)—R^{11}$, $—N(R^{10})—C(O)—O—R^{11}$, $—(O—CH_2CH_2)_n—R^d$, =O, alkyl, carbocyclyl, carbocyclylalkyl, heterocyclyl, heterocyclylalkyl, alkenyl, and alkynyl, wherein alkyl, carbocyclyl, carbocyclylalkyl, heterocyclyl, heterocyclylalkyl, alkenyl, and alkynyl can be optionally substituted, or if more than one group $R^E$ is present and two of the groups $R^E$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted;

for each occurrence, $R^{10}$ is independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{11}$ is independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{14}$ is independently selected from the group consisting of hydrogen, $—(CH_2CH_2—O)_n—R^f$, $—(CH_2CH_2—O)_n—(CH_2CH_2)—R^d$, alkyl, carbocyclyl and heterocyclyl, wherein alkyl, carbocyclyl and heterocyclyl can be optionally substituted;

for each occurrence, n is independently 1 to 4; and for each occurrence, m is independently 1 to 4.

7. The compound according to item 6, which is a compound of the formula (IIa):

(IIa)

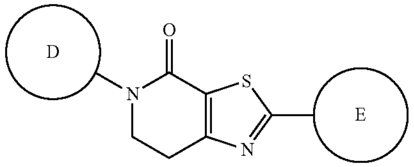

wherein D and E are as defined in item 6.

8. The compound according to any one of items 1 to 7, wherein the compound is detectably labeled, preferably with $^2H$, $^3H$, $^{18}F$, $^{123}I$, $^{124}I$, $^{125}I$, $^{131}I$, $^{11}C$, $^{13}N$, $^{15}O$, and $^{77}Br$, more preferably with $^{18}F$.

9. A diagnostic composition comprising a compound according to any one of items 1 to 8 and a pharmaceutically acceptable carrier, diluent, adjuvant and/or excipient.

10. The compound according to any one of items 1 to 8 for use in diagnostics.

11. The compound according to any one of items 1 to 8 for use in the imaging of alpha-synuclein aggregates including, but not limited to, Lewy bodies and/or Lewy neurites.

12. The compound for use according to item 11, wherein the compound is for use in the positron emission tomography imaging of alpha-synuclein aggregates including, but not limited to, Lewy bodies and/or Lewy neurites.

13. The compound according to any one of items 1 to 8 for use in the diagnostics of a disorder or abnormality associated with alpha-synuclein aggregates including, but not limited to, Lewy bodies and/or Lewy neurites or a predisposition therefor.

14. The compound for use according to item 13, wherein the disorder is selected from Parkinson's disease (including sporadic, familial with alpha-synuclein mutations, familial with mutations other than alpha-synuclein, pure autonomic failure or Lewy body dysphagia), dementia with Lewy bodies (including "pure" Lewy body dementia), sporadic Alzheimer's disease, familial Alzheimer's disease with APP mutations, familial Alzheimer's disease with PS-1, PS-2 or other mutations, familial British dementia, Lewy body variant of Alzheimer's disease, normal aging (including Down syndrome), multiple system atrophy (including Shy-Drager syndrome, striatonigral degeneration or olivopontocerebellar atrophy), traumatic brain injury, chronic traumatic encephalopathy, tauopathies (including Pick's disease, frontotemporal dementia, progressive supranuclear palsy, corticobasal degeneration or Niemann-Pick type C1 disease), motor neuron disease, amyotrophic lateral sclerosis (including sporadic, familial or ALS-dementia complex of Guam), neuroaxonal dystrophy, neurodegeneration with brain iron accumulation type 1 (including Hallervorden-Spatz syndrome), prion diseases, ataxia telangiectatica, Meige's syndrome, subacute sclerosing panencephalitis, Gaucher disease, lysosomal storage disorders (including Kufor-Rakeb syndrome and Sanfilippo syndrome) and rapid eye movement (REM) sleep behavior disorder, preferably Parkinson's disease.

15. A method of imaging of alpha-synuclein aggregates including, but not limited to, Lewy bodies and/or Lewy neurites, wherein an effective amount of a compound according to any one of items 1 to 8 is administered to a patient in need thereof.

16. The method according to item 15, wherein the method is positron emission tomography imaging of alpha-synuclein aggregates including, but not limited to, Lewy bodies and/or Lewy neurites.

17. A method of diagnosing a disorder or abnormality associated with alpha-synuclein aggregates including, but not limited to, Lewy bodies and/or Lewy neurites or a predisposition therefor in a subject, wherein a diagnostically effective amount of a compound according to any one of items 1 to 8 is administered to a patient in need thereof.

18. The method according to item 17, wherein the disorder is selected from Parkinson's disease (including sporadic, familial with alpha-synuclein mutations, familial with mutations other than alpha-synuclein, pure autonomic failure or Lewy body dysphagia), dementia with Lewy bodies (including "pure" Lewy body dementia), sporadic Alzheimer's disease, familial Alzheimer's disease with APP mutations, familial Alzheimer's disease with PS-1, PS-2 or other mutations, familial British dementia, Lewy body variant of Alzheimer's disease, normal aging (including Down syndrome), multiple system atrophy (including Shy-Drager syndrome, striatonigral degeneration or olivopontocerebellar atrophy), traumatic brain injury, chronic traumatic encephalopathy, tauopathies (including Pick's disease, frontotemporal dementia, progressive supranuclear palsy, corticobasal degeneration or Niemann-Pick type C1 disease), motor neuron disease, amyotrophic lateral sclerosis (including sporadic, familial or ALS-dementia complex of Guam), neuroaxonal dystrophy, neurodegeneration with brain iron accumulation type 1 (including Hallervorden-Spatz syndrome), prion diseases, ataxia telangiectatica, Meige's syndrome, subacute sclerosing panencephalitis, Gaucher disease, lysosomal storage disorders (including Kufor-Rakeb syndrome and Sanfilippo syndrome) and rapid eye movement (REM) sleep behavior disorder, preferably Parkinson's disease.

19. A method of collecting data for the diagnosis of a disorder or abnormality associated with alpha-synuclein aggregates including, but not limited to, Lewy bodies and/or Lewy neurites in a patient comprising:

(a) bringing a sample or specific body part or body area of the patient suspected to contain alpha-synuclein aggregates including, but not limited to, Lewy bodies and/or Lewy neurites into contact with a compound as defined in any one of items 1 to 8;

(b) allowing the compound to bind to the alpha-synuclein aggregates including, but not limited to, Lewy bodies and/or Lewy neurites;

(c) detecting the compound bound to the alpha-synuclein aggregates including, but not limited to, Lewy bodies and/or Lewy neurites; and (d) optionally correlating the presence or absence of compound binding with the alpha-synuclein aggregates including, but not limited to, Lewy bodies and/or Lewy neurites with the presence or absence of alpha-synuclein aggregates including, but not limited to, Lewy bodies and/or Lewy neurites in the sample or specific body part or body area.

20. A method of collecting data for determining a predisposition to a disorder or abnormality associated with alpha-synuclein aggregates including, but not limited to, Lewy bodies and/or Lewy neurites in a patient comprising detecting the specific binding of a compound as defined in any one of items 1 to 8 to alpha-synuclein aggregates including, but not limited to, Lewy bodies and/or Lewy neurites in a sample or specific body part or body area of the patient which comprises the steps of:
 (a) bringing the sample or specific body part or body area suspected to contain the alpha-synuclein aggregates including, but not limited to, Lewy bodies and/or Lewy neurites into contact with the compound as defined in any one of items 1 to 8, which compound specifically binds to the alpha-synuclein aggregates including, but not limited to, Lewy bodies and/or Lewy neurites;
 (b) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;
 (c) detecting the formation of the compound/(alpha-synuclein aggregates including, but not limited to, Lewy bodies and/or Lewy neurites) complex;
 (d) optionally correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area; and
 (e) optionally comparing the amount of the compound/(alpha-synuclein aggregates including, but not limited to, Lewy bodies and/or Lewy neurites) complex to a normal control value.

21. A method of collecting data for monitoring residual disorder in a patient suffering from a disorder or abnormality associated with alpha-synuclein aggregates including, but not limited to, Lewy bodies and/or Lewy neurites who has been treated with a medicament, wherein the method comprises:
 (a) bringing a sample or specific body part or body area suspected to contain alpha-synuclein aggregates including, but not limited to, Lewy bodies and/or Lewy neurites into contact with a compound as defined in any one of items 1 to 8, which compound specifically binds to the alpha-synuclein aggregates including, but not limited to, Lewy bodies and/or Lewy neurites;
 (b) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;
 (c) detecting the formation of the compound/(alpha-synuclein aggregates including, but not limited to, Lewy bodies and/or Lewy neurites) complex;
 (d) optionally correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area; and
 (e) optionally comparing the amount of the compound/(alpha-synuclein aggregates including, but not limited to, Lewy bodies and/or Lewy neurites) complex to a normal control value.

22. The method according to item 21, wherein step (d) is present and wherein the method further comprises steps (i) to (vi) before step (a):
 (i) bringing a sample or specific body part or body area suspected to contain alpha-synuclein aggregates including, but not limited to, Lewy bodies and/or Lewy neurites into contact with the compound as defined in any one of items 1 to 8, which compound specifically binds to the alpha-synuclein aggregates including, but not limited to, Lewy bodies and/or Lewy neurites;
 (ii) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;
 (iii) detecting the formation of the compound/(alpha-synuclein aggregates including, but not limited to, Lewy bodies and/or Lewy neurites) complex;
 (iv) correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area;
 (v) optionally comparing the amount of the compound/(alpha-synuclein aggregates including, but not limited to, Lewy bodies and/or Lewy neurites) complex to a normal control value; and
 (vi) treating the patient with the medicament;
 and wherein the method further comprises step (A) after step (d) or step (e):
 (A) comparing the amount of the compound/(alpha-synuclein aggregates including, but not limited to, Lewy bodies and/or Lewy neurites) complex determined in step (iv) to the amount of the compound/(alpha-synuclein aggregates including, but not limited to, Lewy bodies and/or Lewy neurites) complex determined in step (d).

23. The method according to item 21 or 22, wherein steps (a) to (c) and optionally steps (d) and (e) are repeated one or more times.

24. A method of collecting data for predicting responsiveness of a patient suffering from a disorder or abnormality associated with alpha-synuclein aggregates including, but not limited to, Lewy bodies and/or Lewy neurites and being treated with a medicament comprising:
 (a) bringing a sample or specific body part or body area suspected to contain alpha-synuclein aggregates including, but not limited to, Lewy bodies and/or Lewy neurites into contact with a compound as defined in any one of items 1 to 8, which compound specifically binds to the alpha-synuclein aggregates including, but not limited to, Lewy bodies and/or Lewy neurites;
 (b) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;
 (c) detecting the formation of the compound/(alpha-synuclein aggregates including, but not limited to, Lewy bodies and/or Lewy neurites) complex;

(d) optionally correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area; and (e) optionally comparing the amount of the compound/(alpha-synuclein aggregates including, but not limited to, Lewy bodies and/or Lewy neurites) complex to a normal control value.

25. The method according to item 24, wherein step (d) is present and wherein the method further comprises steps (i) to (vi) before step (a):

(i) bringing a sample or specific body part or body area suspected to contain alpha-synuclein aggregates including, but not limited to, Lewy bodies and/or Lewy neurites into contact with the compound as defined in any one of items 1 to 8, which compound specifically binds to the alpha-synuclein aggregates including, but not limited to, Lewy bodies and/or Lewy neurites;

(ii) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;

(iii) detecting the formation of the compound/(alpha-synuclein aggregates including, but not limited to, Lewy bodies and/or Lewy neurites) complex;

(iv) correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area;

(v) optionally comparing the amount of the compound/(alpha-synuclein aggregates including, but not limited to, Lewy bodies and/or Lewy neurites) complex to a normal control value; and (vi) treating the patient with the medicament;

and wherein the method further comprises step (A) after step (d) or step (e):

(A) comparing the amount of the compound/(alpha-synuclein aggregates including, but not limited to, Lewy bodies and/or Lewy neurites) complex determined in step (iv) to the amount of the compound/(alpha-synuclein aggregates including, but not limited to, Lewy bodies and/or Lewy neurites) complex determined in step (d).

26. The method according to item 24 or 25, wherein steps (a) to (c) and optionally steps (d) and (e) are repeated one or more times.

27. A method of diagnosing a disorder or abnormality associated with alpha-synuclein aggregates including, but not limited to, Lewy bodies and/or Lewy neurites in a patient comprising:

(a) bringing a sample or specific body part or body area of the patient suspected to contain alpha-synuclein aggregates including, but not limited to, Lewy bodies and/or Lewy neurites into contact with a compound as defined in any one of items 1 to 8;

(b) allowing the compound to bind to the alpha-synuclein aggregates including, but not limited to, Lewy bodies and/or Lewy neurites;

(c) detecting the compound bound to the alpha-synuclein aggregates including, but not limited to, Lewy bodies and/or Lewy neurites; and (d) optionally correlating the presence or absence of compound binding with the alpha-synuclein aggregates including, but not limited to, Lewy bodies and/or Lewy neurites with the presence or absence of alpha-synuclein aggregates including, but not limited to, Lewy bodies and/or Lewy neurites in the sample or specific body part or body area.

28. A method of determining a predisposition to a disorder or abnormality associated with alpha-synuclein aggregates including, but not limited to, Lewy bodies and/or Lewy neurites in a patient comprising detecting the specific binding of a compound as defined in any one of items 1 to 8 to alpha-synuclein aggregates including, but not limited to, Lewy bodies and/or Lewy neurites in a sample or specific body part or body area of the patient which comprises the steps of:

(a) bringing the sample or specific body part or body area suspected to contain the alpha-synuclein aggregates including, but not limited to, Lewy bodies and/or Lewy neurites into contact with the compound as defined in any one of items 1 to 8, which compound specifically binds to the alpha-synuclein aggregates including, but not limited to, Lewy bodies and/or Lewy neurites;

(b) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;

(c) detecting the formation of the compound/(alpha-synuclein aggregates including, but not limited to, Lewy bodies and/or Lewy neurites) complex;

(d) optionally correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area; and (e) optionally comparing the amount of the compound/(alpha-synuclein aggregates including, but not limited to, Lewy bodies and/or Lewy neurites) complex to a normal control value.

29. A method of monitoring residual disorder in a patient suffering from a disorder or abnormality associated with alpha-synuclein aggregates including, but not limited to, Lewy bodies and/or Lewy neurites who has been treated with a medicament, wherein the method comprises:

(a) bringing a sample or specific body part or body area suspected to contain alpha-synuclein aggregates including, but not limited to, Lewy bodies and/or Lewy neurites into contact with a compound as defined in any one of items 1 to 8, which compound specifically binds to the alpha-synuclein aggregates including, but not limited to, Lewy bodies and/or Lewy neurites;

(b) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;

(c) detecting the formation of the compound/(alpha-synuclein aggregates including, but not limited to, Lewy bodies and/or Lewy neurites) complex;

(d) optionally correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area; and (e) optionally comparing the amount of the compound/(alpha-synuclein aggregates including, but not limited to, Lewy bodies and/or Lewy neurites) complex to a normal control value.

30. The method according to item 29, wherein step (d) is present and wherein the method further comprises steps (i) to (vi) before step (a):

(i) bringing a sample or specific body part or body area suspected to contain alpha-synuclein aggregates including, but not limited to, Lewy bodies and/or Lewy neurites into contact with the compound as defined in any one of items 1 to 8, which compound specifically binds to the alpha-synuclein aggregates including, but not limited to, Lewy bodies and/or Lewy neurites;

(ii) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;

(iii) detecting the formation of the compound/(alpha-synuclein aggregates including, but not limited to, Lewy bodies and/or Lewy neurites) complex;

(iv) correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area;

(v) optionally comparing the amount of the compound/(alpha-synuclein aggregates including, but not limited to, Lewy bodies and/or Lewy neurites) complex to a normal control value; and (vi) treating the patient with the medicament;

and wherein the method further comprises step (A) after step (d) or step (e):

(A) comparing the amount of the compound/(alpha-synuclein aggregates including, but not limited to, Lewy bodies and/or Lewy neurites) complex determined in step (iv) to the amount of the compound/(alpha-synuclein aggregates including, but not limited to, Lewy bodies and/or Lewy neurites) complex determined in step (d).

31. The method according to item 29 or 30, wherein steps (a) to (c) and optionally steps (d) and (e) are repeated one or more times.

32. A method of predicting responsiveness of a patient suffering from a disorder or abnormality associated with alpha-synuclein aggregates including, but not limited to, Lewy bodies and/or Lewy neurites and being treated with a medicament comprising:

(a) bringing a sample or specific body part or body area suspected to contain alpha-synuclein aggregates including, but not limited to, Lewy bodies and/or Lewy neurites into contact with a compound as defined in any one of items 1 to 8, which compound specifically binds to the alpha-synuclein aggregates including, but not limited to, Lewy bodies and/or Lewy neurites;

(b) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;

(c) detecting the formation of the compound/(alpha-synuclein aggregates including, but not limited to, Lewy bodies and/or Lewy neurites) complex;

(d) optionally correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area; and (e) optionally comparing the amount of the compound/(alpha-synuclein aggregates including, but not limited to, Lewy bodies and/or Lewy neurites) complex to a normal control value.

33. The method according to item 32, wherein step (d) is present and wherein the method further comprises steps (i) to (vi) before step (a):

(i) bringing a sample or specific body part or body area suspected to contain alpha-synuclein aggregates including, but not limited to, Lewy bodies and/or Lewy neurites into contact with the compound as defined in any one of items 1 to 8, which compound specifically binds to the alpha-synuclein aggregates including, but not limited to, Lewy bodies and/or Lewy neurites;

(ii) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;

(iii) detecting the formation of the compound/(alpha-synuclein aggregates including, but not limited to, Lewy bodies and/or Lewy neurites) complex;

(iv) correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area;

(v) optionally comparing the amount of the compound/(alpha-synuclein aggregates including, but not limited to, Lewy bodies and/or Lewy neurites) complex to a normal control value; and (vi) treating the patient with the medicament;

and wherein the method further comprises step (A) after step (d) or step (e):

(A) comparing the amount of the compound/(alpha-synuclein aggregates including, but not limited to, Lewy bodies and/or Lewy neurites) complex determined in step (iv) to the amount of the compound/(alpha-synuclein aggregates including, but not limited to, Lewy bodies and/or Lewy neurites) complex determined in step (d).

34. The method according to item 32 or 33, wherein steps (a) to (c) and optionally steps (d) and (e) are repeated one or more times.

35. The method according to any one of items 19 to 34, wherein the disorder is selected from Parkinson's disease (including sporadic, familial with alpha-synuclein mutations, familial with mutations other than alpha-synuclein, pure autonomic failure or Lewy body dysphagia), dementia with Lewy bodies (including "pure" Lewy body dementia), sporadic Alzheimer's disease, familial Alzheimer's disease with APP mutations, familial Alzheimer's disease with PS-1, PS-2 or other mutations, familial British dementia, Lewy body variant of Alzheimer's disease, normal aging (including Down syndrome), multiple system atrophy (including Shy-Drager syndrome, striatonigral degeneration or olivopontocerebellar atrophy), traumatic brain injury, chronic traumatic encephalopathy, tauopathies (including Pick's disease, frontotemporal dementia, progressive supranuclear palsy, corticobasal degeneration or Niemann-Pick type C1 disease), motor neuron disease, amyotrophic lateral sclerosis (including sporadic, familial or ALS-dementia complex of Guam), neuroaxonal dystrophy, neurodegeneration with brain iron accumulation type 1 (including Hallervorden-Spatz syndrome), prion diseases, ataxia telangiectatica, Meige's syndrome, subacute sclerosing panencephalitis, Gaucher disease, lysosomal storage disorders (including Kufor-Rakeb syndrome and Sanfilippo syndrome) and rapid eye movement (REM) sleep behavior disorder, preferably Parkinson's disease.

36. A method of determining the amount of alpha-synuclein aggregates including, but not limited to, Lewy bodies and/or Lewy neurites in a sample or specific body part or body area of a patient comprising:
  (a) providing the sample or specific body part or body area;
  (b) testing the sample or specific body part or body area for the presence of alpha-synuclein aggregates including, but not limited to, Lewy bodies and/or Lewy neurites with a compound as defined in any one of items 1 to 8;
  (c) determining the amount of compound bound to the alpha-synuclein aggregates including, but not limited to, Lewy bodies and/or Lewy neurites; and
  (d) calculating the amount of alpha-synuclein aggregates including, but not limited to, Lewy bodies and/or Lewy neurites in the sample or specific body part or body area.

37. The method according to any one of items 19 to 36, wherein the sample is a tissue and/or a body fluid representative of the specific body part or body area under investigation.

38. A mixture comprising a compound as defined in any one of items 1 to 8 and at least one compound selected from an imaging agent different from the compound as defined in any one of items 1 to 8, preferably an abeta or tau imaging agent, a pharmaceutically acceptable carrier, a diluent and an excipient.

39. A mixture comprising a compound as defined in any one of items 1 to 8 and at least one compound selected from a therapeutic agent different from the compound as defined in any one of items 1 to 8, a pharmaceutically acceptable carrier, a diluent and an excipient.

40. A pharmaceutical composition comprising a compound according to any one of items 1 to 8 and a pharmaceutically acceptable carrier, diluent, adjuvant or excipient.

41. The compound as defined in any one of items 1 to 8 for use in the treatment, alleviation or prevention of a disorder or abnormality associated with alpha-synuclein aggregates.

42. A method of treating, alleviating or preventing a disorder or abnormality associated with alpha-synuclein aggregates, wherein a therapeutically effective amount of a compound as defined in any one of items 1 to 8 is administered to a patient in need thereof.

43. The compound for use according to item 41 or the method according to item 42, wherein the disorder is selected from Parkinson's disease (including sporadic, familial with alpha-synuclein mutations, familial with mutations other than alpha-synuclein, pure autonomic failure or Lewy body dysphagia), dementia with Lewy bodies (including "pure" Lewy body dementia), sporadic Alzheimer's disease, familial Alzheimer's disease with APP mutations, familial Alzheimer's disease with PS-1, PS-2 or other mutations, familial British dementia, Lewy body variant of Alzheimer's disease, normal aging (including Down syndrome), multiple system atrophy (including Shy-Drager syndrome, striatonigral degeneration or olivopontocerebellar atrophy), traumatic brain injury, chronic traumatic encephalopathy, tauopathies (including Pick's disease, frontotemporal dementia, progressive supranuclear palsy, corticobasal degeneration or Niemann-Pick type C1 disease), motor neuron disease, amyotrophic lateral sclerosis (including sporadic, familial or ALS-dementia complex of Guam), neuroaxonal dystrophy, neurodegeneration with brain iron accumulation type 1 (including Hallervorden-Spatz syndrome), prion diseases, ataxia telangiectatica, Meige's syndrome, subacute sclerosing panencephalitis, Gaucher disease, lysosomal storage disorders (including Kufor-Rakeb syndrome and Sanfilippo syndrome) and rapid eye movement (REM) sleep behavior disorder, preferably Parkinson's disease.

44. A compound of formula (IIIa) or (IIIb)

(IIIa)

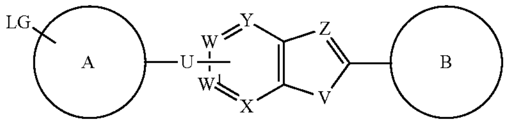

(IIIb)

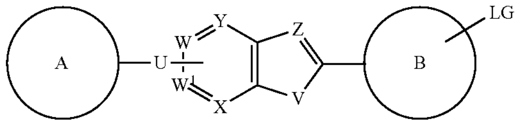

wherein $R^e$, $R^{14}$, $R^A$, m, B, U, Y, W, $W^1$, X, Z and V are as defined in item 1,

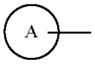

is selected from the group consisting of

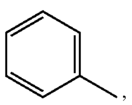, 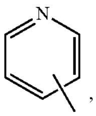, 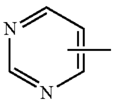, 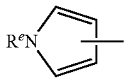, 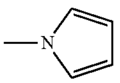, 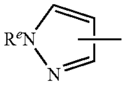, 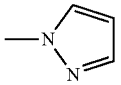, 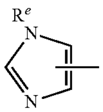, 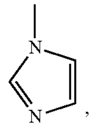, 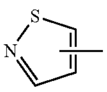, 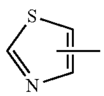, 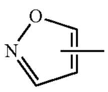, 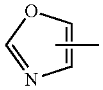, 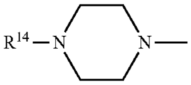, 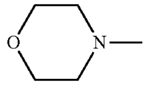, and -continued

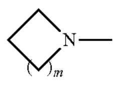 wherein 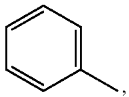, 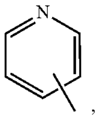,

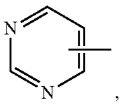, 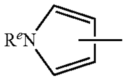, 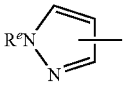, 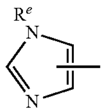,

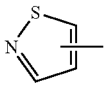, 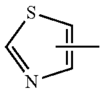, 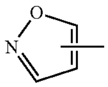, and

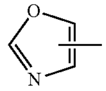

can be attached at any available position to the moiety U, and wherein

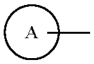

can be optionally substituted by one or more substituents $R^A$; and LG is a leaving group.

45. A compound of formula (IVa) or (IVb)

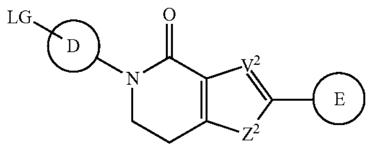

(IVa)

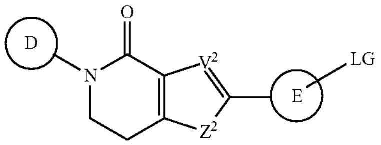

(IVb)

wherein $R^e$, $R^D$, E, $V^2$ and $Z^2$ are as defined in item 6;

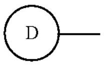

is selected from the group consisting of

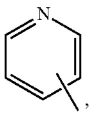, 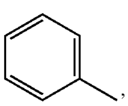, 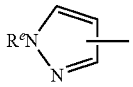

and alkyl, wherein

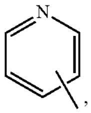, 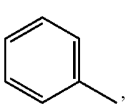, 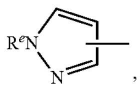, and alkyl can be attached at any available position, and wherein

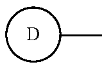

can be optionally substituted by one or more substituents $R^D$; and

LG is a leaving group.

46. The compound according to item 44 or 45, wherein LG is selected from nitro, halogen, trimethylammonium, $C_{1-4}$ alkyl sulfonate or $C_{6-10}$ aryl sulfonate.

47. A method for preparing the compound according to item 8, wherein the compound is labelled by $^{18}F$, comprising reacting the compound according to item 44 or 45 with a $^{18}F$-fluorinating agent, so that LG is replaced by $^{18}F$.

48. The method according to item 47, wherein the $^{18}F$-fluorinating agent is selected from $K^{18}F$, $H^{18}F$, $Cs^{18}F$, $Na^{18}F$ and tetrabuylammonium [$^{18}F$]fluoride.

49. Use of the compound according to any one of items 1 to 8 as an in vitro analytical reference or an in vitro screening tool.

50. A test kit for detection and/or diagnosis of a disorder or abnormality associated with alpha-synuclein aggregates, wherein the test kit comprises at least one compound as defined in any one of items 1 to 8.

51. The test kit according to item 50 comprising a container containing at least one compound as defined in any one of items 1 to 8 and instructions for using the at least one compound for the purpose of binding to alpha-synuclein aggregates to form a compound/protein complex and detecting the formation of the compound/protein complex such that presence or absence of the compound/protein complex correlates with the presence or absence of the alpha-synuclein aggregates.

52. A kit for preparing a radiopharmaceutical preparation, wherein the kit comprises a sealed vial containing at least one compound as defined in item 44 or 45.

Definitions

Within the meaning of the present application the following definitions apply:

"Alkyl" refers to a saturated straight or branched organic moiety consisting of carbon and hydrogen atoms. Examples of suitable alkyl groups have 1 to 6 carbon atoms, preferably 1 to 4 carbon atoms, and include methyl, ethyl, propyl, isopropyl, n-butyl, t-butyl and isobutyl.

"Carbocyclyl" refers to a cyclic organic moiety consisting of carbon and hydrogen atoms. Examples of suitable carbocyclyl groups have 3 to 10 carbon atoms, preferably 3, 4, 5 or 6 carbon atoms. The carbocyclyl group can be unsaturated or saturated. The term "carbocyclyl" also covers an aromatic cyclic organic moiety (aryl group) consisting of carbon and hydrogen atoms. Examples of the carbocyclyl group include cyclopentyl, cyclohexyl and phenyl.

"Heterocyclyl" refers to a carbocyclyl group as defined above in which at least one of the carbon atoms has been replaced by a heteroatom which is, e.g., selected from N, O or S, or heteroatom (e.g., N, O and/or S)-containing moiety.

The heterocyclyl group can be unsaturated or saturated. It covers both heteroalkyl groups and heteroaryl groups. The heterocyclyl can also be annelated, connected in a bridged manner or connected in a spiro manner such as 6-membered bicyclic rings, 7-membered bicyclic rings, 8-membered bicyclic rings, 6-membered spirocyclic rings, 7-membered spirocyclic rings or 8-membered spirocyclic rings. Examples include azetidine, pyrrolidine, pyrrole, tetrahydrofuran, furan, thiolane, thiophene, imidazolidine, pyrazolidine, imidazole, pyrazole, oxazolidine, isoxazolidine, oxazole, isoxazole, thiazolidine, isothiazolidine, thiazole, isothiazole, dioxolane, dithiolane, triazole, furazan, oxadiazoles, thiadiazole, dithiazole, tetrazole, piperidine, oxane, thiane, pyridine, pyran, thiopyran, piperazine, diazine (including pyrazine and pyrimidine), morpholine, oxazine, thiomorpholine, thiazine, dioxane, dioxine, dithiane, dithiine, triazine, trioxane, tetrazine, azepane, azepine, oxepane, oxepine, thiepane, thiepine, 3-azabicyclo[3.1.0]hexane, azaspiro[3.3]heptane, diazaspiro[3.3]heptane, azabicyclo [3.2.1]octane and diazabicyclo[3.2.1]octane.

Examples of preferred heterocyclyl groups include azetidine, morpholine, piperazine, pyrrolidine, tetrahydrofuran, piperidine, azaspiro[3.3]heptane, etc. Examples of possible heteroaryl groups include pyridine, pyrazole, etc.

“Alkenyl” refers to an organic moiety consisting of carbon and hydrogen atoms which includes at least one double bond. Examples of suitable alkenyl groups have 2 to 6 carbon atoms, preferably 2 to 4 carbon atoms, and include propenyl and butenyl.

“Alkynyl” refers to an organic moiety consisting of carbon and hydrogen atoms which includes at least one triple bond. Examples of suitable alkynyl groups have 2 to 6 carbon atoms, preferably 2 to 4 carbon atoms, and include propinyl and butinyl.

“Aryl” refers to homocyclic aromatic organic moieties containing 1 or 2 rings consisting of carbon and hydrogen atoms which preferably have 6 to 12 carbon atoms, more preferably 5 or 6 carbon atoms. Examples are, but not limited to, phenyl, biphenyl, and naphthyl.

“Heteroaryl” refers to an aryl group as defined above in which at least one of the carbon atoms has been replaced by a heteroatom which is, e.g., selected from N, O or S, or heteroatom (e.g., N, O and/or S)-containing moiety. Examples of possible heteroaryl groups include pyridine, etc.

“Hal” or “halogen” refers to F, Cl, Br, and I. With respect to diagnostic and pharmaceutical applications, F (e.g., $^{19}F$ and $^{18}F$) is particularly preferred.

“Carbocyclylalkyl” refers to a group carbocyclyl-alkyl-.

“Heterocyclylalkyl” refers to a group heterocyclyl-alkyl-.

“5- to 8-Membered ring system containing carbon atoms and optionally one or more heteroatoms selected from O, S, or N or optionally one or more heteroatom (e.g., N, O and/or S)-containing moieties” refers to ring system having 5 to 8 carbon atoms and optionally one or more heteroatoms selected from O, S, or N or optionally one or more heteroatom (e.g., N, O and/or S)-containing moieties. The term is also meant to include monocyclic, bicyclic, and polycyclic versions thereof. If more than one ring is present, the rings can be annelated, connected in a bridged manner or connected in a spiro manner. The ring(s) can be either carbocyclic or heterocyclic and can be saturated, unsaturated or aromatic. Examples of these heterocyclic groups include, but are not restricted to, azetidine (azacyclobutane), pyrrolidine (azacyclopentane), pyrrole, imidazolidine, pyrazolidine, imidazole, pyrazole, oxazolidine, isoxazolidine, oxazole, isoxazole, thiazolidine, isothiazolidine, thiazole, isothiazole, triazole, furazan, oxadiazoles, thiadiazole, dithiazole, tetrazole, imidazoline, piperidine (azacyclohexane), pyridine, piperazine, pyrrolidine, diazine (including pyrazine and pyrimidine), morpholine, thiomorpholine, thiazine, triazine, tetrazine, azepane, and azepine. Preferably the 5- to 8-membered ring containing carbon atoms and optionally one or more heteroatoms selected from O, S, or N or optionally one or more heteroatom (e.g., N, O and/or S)-containing moieties is selected from, imidazoline, dioxolane, piperidine, piperazine, pyrrolidine, tetrahydrofuran, dioxane, phenyl, pyridine, thiazole, diazines (including pyrazine and pyrimidine), and oxadiazoles, more preferably imidazoline, dioxolane, piperidine, piperazine, pyrrolidine, phenyl and pyridine. The 5- to 8-membered ring containing carbon atoms and optionally one or more heteroatoms selected from O, S, or N or optionally one or more heteroatom (e.g., N, O and/or S)-containing moieties can be attached at any available position. Preferably, the “5- to 8-membered ring system containing carbon atoms and optionally one or more heteroatoms selected from O, S, or N or optionally one or more heteroatom (e.g., N, O and/or S)-containing moieties” is a “5- to 8-membered ring containing carbon atoms and optionally one or more heteroatoms selected from O, S, or N or optionally one or more heteroatom (e.g., N, O and/or S)-containing moieties”, more preferably it is a 4-, 5- or 6-membered (preferably saturated) ring containing carbon atoms and optionally one or more heteroatoms selected from O, S, or N. Specific examples are the 5- or 6-membered rings containing carbon atoms and optionally one or more heteroatoms selected from O, S, or N given in the above list.

If more than one group $R^A$, $R^B$, $R^D$ or $R^E$, respectively, is present and two of the groups $R^A$, $R^B$, $R^D$ or $R^E$, respectively, are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties. In this embodiment, the 5- to 8-membered ring can be any 5- to 8-membered ring containing carbon atoms and optionally one or more heteroatoms selected from O, S, or N or optionally one or more heteroatom (e.g., N, O and/or S)-containing moieties. Examples thereof can be found in the list of examples given for the “5- to 8-membered ring system containing carbon atoms and optionally one or more heteroatoms selected from O, S, or N or optionally one or more heteroatom (e.g., N, O and/or S)-containing moieties”, as well as in the lists of examples of the carbocyclyl, aryl, and heterocyclyl groups. The ring formed by two adjacent groups $R^A$, $R^B$, $R^D$ or $R^E$, respectively, is preferably a 5- or 6-membered, saturated or unsaturated ring containing carbon atoms and optionally one or more heteroatoms selected from O, S, or N or optionally one or more heteroatom (e.g., N, O and/or S)-containing moieties. Specific examples of the 5- or 6-membered, saturated or unsaturated rings containing carbon atoms and optionally one or more heteroatoms selected from O, S, or N or optionally one or more heteroatom (e.g., N, O and/or S)-containing moieties are given in the above list. In all of these embodiments, the heteroatom is preferably N and/or O. In all of these embodiments, the ring preferably contains 0, 1, 2 or 3 heteroatom(s). In all of these embodiments, the ring preferably contains 0 or 1 heteroatom (e.g., N, O and/or S)-containing moieties.

“Heteroatom-containing moieties” are moieties which contain e.g., N, O and/or S. Examples of such moieties include —C(O)—, —C(O)O—, —C(O)N($R^{50}$)— and —N($R^{50}$)— in which $R^{50}$ is, for each occurrence, independently selected from the group consisting of H or $C_{1-4}$ alkyl, wherein $C_{1-4}$ alkyl can be optionally substituted.

The term "leaving group" (LG) as employed herein is any leaving group and means an atom or group of atoms that can be replaced by another atom or group of atoms. Examples are given e.g. in Synthesis (1982), p. 85-125, table 2, Carey and Sundberg, Organische Synthese, (1995), page 279-281, table 5.8; or Netscher, Recent Res. Dev. Org. Chem., 2003, 7, 71-83, scheme 1, 2, 10 and 15 and others). (Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50, explicitly: scheme 4 pp. 25, scheme 5 pp 28, table 4 pp 30, FIG. 7 pp 33). Preferably, the "leaving group" (LG) is selected from nitro, halogen, trimethylammonium, $C_{1-4}$ alkyl sulfonate and $C_{6-10}$ aryl sulfonate.

If a group is defined as being "optionally substituted" (unless defined otherwise), as chemically appropriate, it can have one or more substituents selected from -Hal, —CN, —OH, $—(O—CH_2CH_2)_n—R$, $—(CH_2CH_2—O)_n—R^*$, $—(CH_2CH_2—O)_n—(CH_2CH_2)—R$ (with R═H or Hal and R*═H, $(CH_2CH_2)_n$Hal, $CHal_3$ or $CH_3$), $—C_{1-6}$ alkyl, $—C_{1-6}$ alkoxy, $—SO_2$-alkyl, $—NH_2$, $—NH(C_{1-6}$ alkyl) or $—N(C_{1-6}$ alkyl$)_2$, preferably -Hal, —CN, —OH, $—(O—CH_2CH_2)_n—R$, $—(CH_2CH_2—O)_n—R^*$, or $—(CH_2CH_2—O)_n—(CH_2CH_2)—R$, more preferably -Hal or —OH. In addition, typical substituents of the aryl groups include one or more alkyl groups, e.g. 1 or 2 alkyl groups, particularly 1 or 2 methyl groups. In these definitions n is 1 to 6.

Compounds of the present invention having one or more optically active carbons can exist as racemates and racemic mixtures, stereoisomers (including diastereomeric mixtures and individual diastereomers, enantiomeric mixtures and single enantiomers, mixtures of conformers and single conformers), tautomers, atropisomers, and rotamers. All isomeric forms are included in the present invention. Compounds described in this invention containing olefinic double bonds include E and Z geometric isomers. Also included in this invention are all salt forms, polymorphs, hydrates and solvates.

The term "polymorphs" refers to the various crystalline structures of the compounds of the present invention. This may include, but is not limited to, crystal morphologies (and amorphous materials) and all crystal lattice forms. Salts of the present invention can be crystalline and may exist as more than one polymorph. Solvates, hydrates as well as anhydrous forms of the salt are also encompassed by the invention. The solvent included in the solvates is not particularly limited and can be any pharmaceutically acceptable solvent. Examples include water and $C_{1-4}$ alcohols (such as methanol or ethanol).

"Pharmaceutically acceptable salts" are defined as derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, nonaqueous media like ethers, ethyl acetate, ethanol, isopropanol, or acetonitrile. Lists of suitable salts can be found in Remington's Pharmaceutical Sciences, $18^{th}$ ed., Mack Publishing Company, Easton, Pa., 1990, p. 1445, the disclosure of which is hereby incorporated by reference.

"Pharmaceutically acceptable" is defined as those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The compounds of the present invention can also be provided in the form of a prodrug, namely a compound which is metabolized in vivo to the active metabolite.

The patients or subjects in the present invention are typically animals, particularly mammals, more particularly humans.

Alpha-synuclein aggregates are multimeric beta-sheet rich assemblies of alpha-synuclein monomers that can form either soluble oligomers or soluble/insoluble protofibrils or mature fibrils which coalesce into intracellular deposits detected as a range of Lewy pathologies in Parkinson's disease and other synucleinopathies. Alpha-synuclein aggregates that are composing Lewy pathologies can be detected as having the following morphologies: Lewy bodies, Lewy neurites, premature Lewy bodies or pale bodies, perikaryal deposits with diffuse, granular, punctate or pleomorphic patterns. Moreover, alpha-synuclein aggregates are the major component of intracellular fibrillary inclusions detected in oligodendrocytes (also referred to as glial cytoplasmic inclusions) and in neuronal somata, axons and nuclei (referred to as neuronal cytoplasmic inclusions) that are the histological hallmarks of multiple system atrophy. Alpha-synuclein aggregates in Lewy pathologies often display substantial increase in post-translational modifications such as phosphorylation, ubiquitination, nitration, and truncation.

Lewy bodies are abnormal aggregates of protein that develop inside nerve cells in Parkinson's disease (PD), Lewy body dementia and other synucleinopathies. Lewy bodies appear as spherical masses that displace other cell components. Morphologically, Lewy bodies can be classified as being brainstem or cortical type. Classic brainstem Lewy bodies are eosinophilic cytoplasmic inclusions consisting of a dense core surrounded by a halo of 5-10-nm-wide radiating fibrils, the primary structural component of which is alpha-synuclein; cortical Lewy bodies differ by lacking a halo. The presence of Lewy bodies is a hallmark of Parkinson's disease.

Lewy neurites are abnormal neuronal processes in diseased neurons, containing granular material, abnormal α-synuclein filaments similar to those found in Lewy bodies, dot-like, varicose structures and axonal spheroids. Like Lewy bodies, Lewy neurites are a feature of α-synucleinopathies such as dementia with Lewy bodies, Parkinson's disease, and multiple system atrophy.

The preferred definitions given in the "Definition"-section apply to all of the embodiments described below unless stated otherwise.

DETAILED DESCRIPTION OF THE INVENTION

The compounds of the present invention will be described in the following. It is to be understood that all possible combinations of the following definitions are also envisaged.

In one embodiment, the present invention relates to a compound of formula (I):

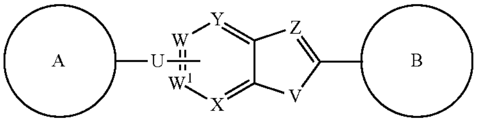

(I)

and all detectably labeled derivatives, stereoisomers, racemic mixtures, pharmaceutically acceptable salts, hydrates, solvates, prodrugs and polymorphs thereof.

A preferred embodiment of the compound of formula (I) is

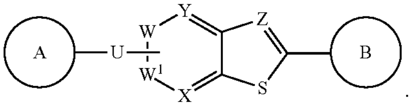

(Ia)

Preferred compounds are also compounds of the formula (Ib) or (Ic):

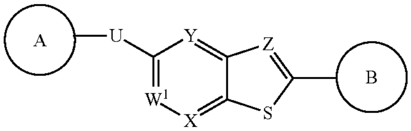

(Ib)

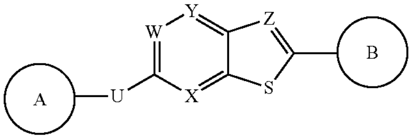

(Ic)

In another embodiment, the compounds of the formula (Id), (Ie), (If), (Ig), (Ih) or (Ii):

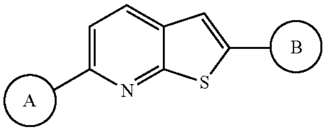

(Id)

-continued

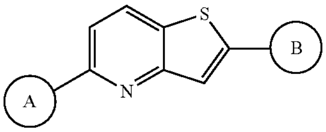

(Ie)

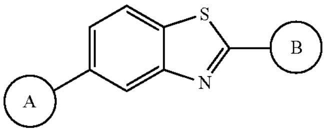

(If)

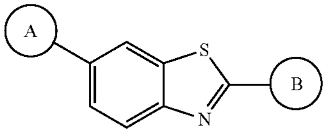

(Ig)

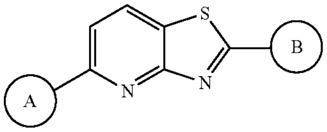

(Ih)

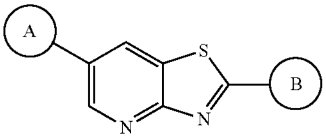

(Ii)

are preferred.

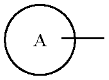

is selected from the group consisting of

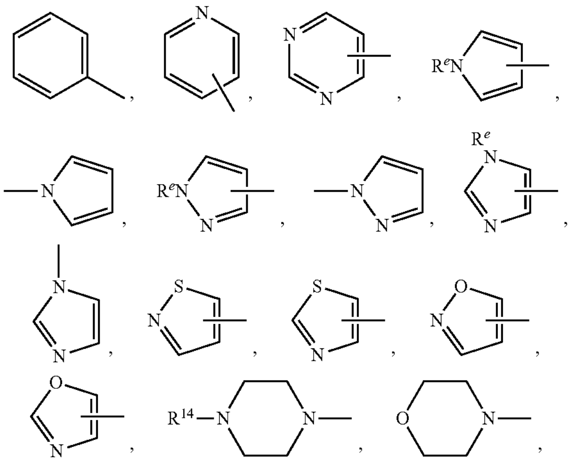

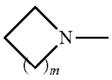

and —CN, wherein

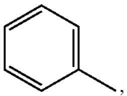

,

-continued

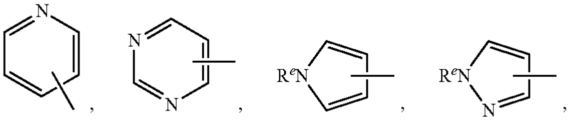

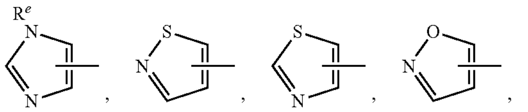

and

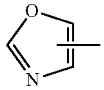

can be attached at any available position to the moiety U.

In one embodiment,

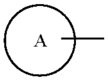

is —CN.

In another embodiment

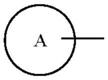

is selected from the group consisting of

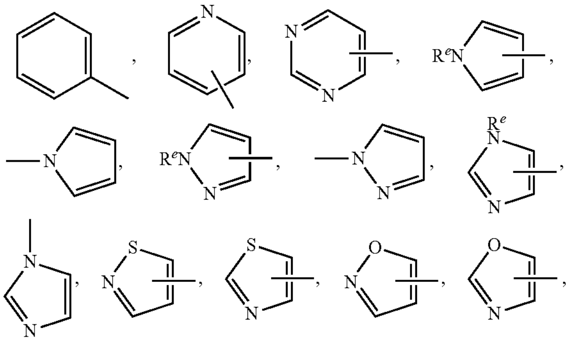

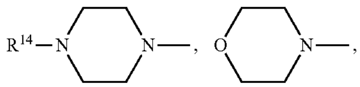

and

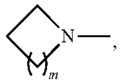

wherein

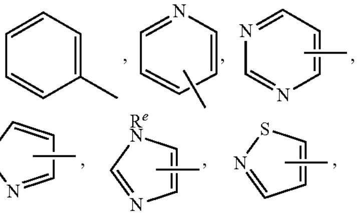

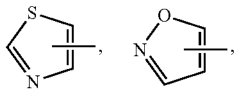

and

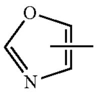

can be attached at any available position to the moiety U.

More preferably,

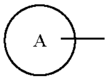

is selected from the group consisting of

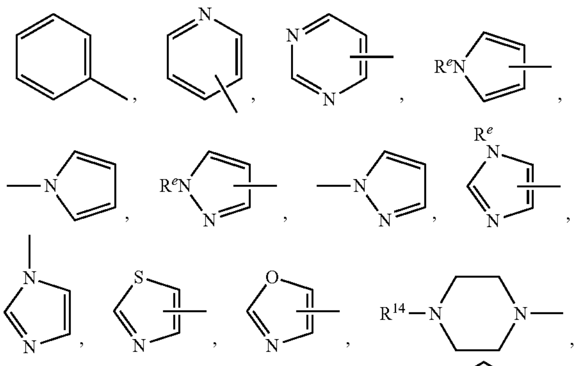

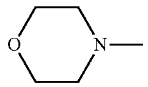

and

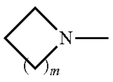

wherein

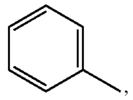

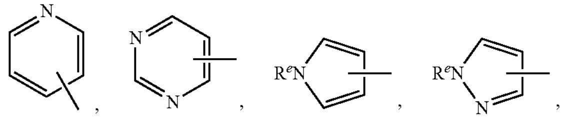

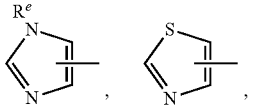

and

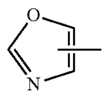

can be attached at any available position to the moiety U.

Even more preferably,

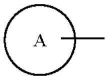

is selected from the group consisting of

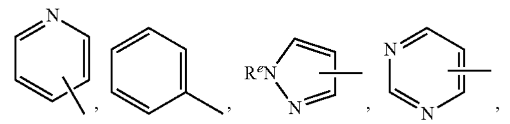

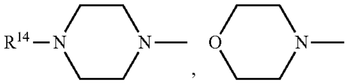

and

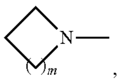

wherein

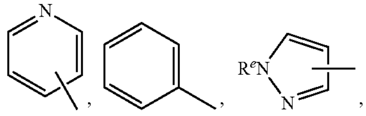

and

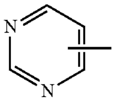

can be attached at any available position to the moiety U.

Examples of preferred groups include
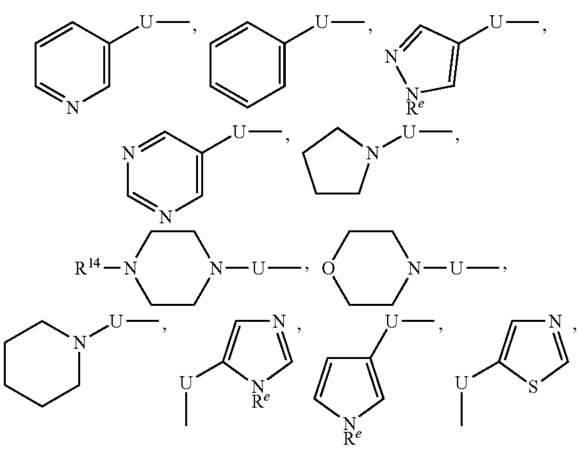
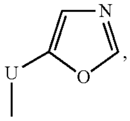, and 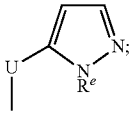
more preferably
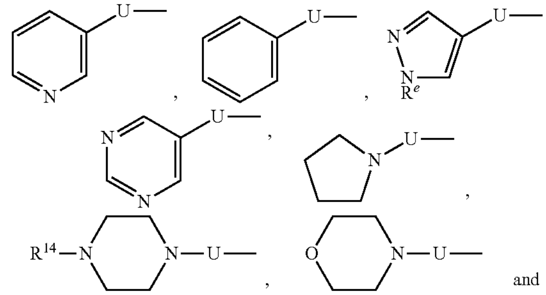
and
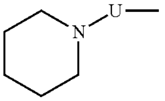
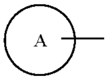
(including any of the preferred options thereof) can be optionally substituted by one or more substituents $R^A$. Examples of preferred substituted groups include
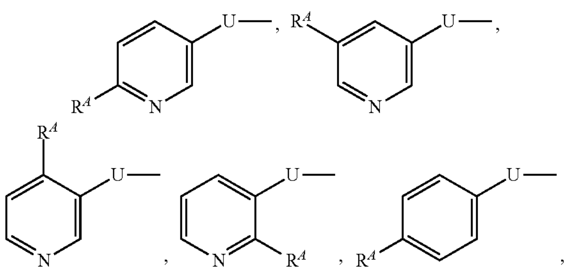
-continued
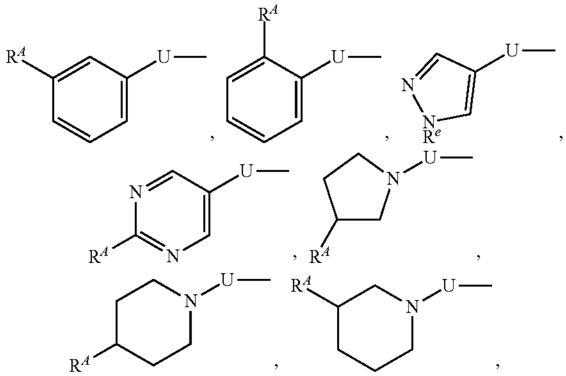
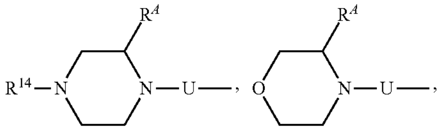 and
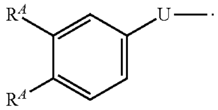
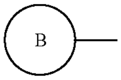
is selected from the group consisting of
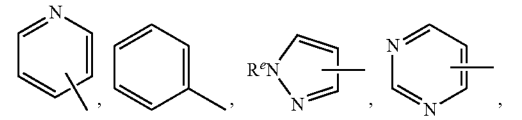
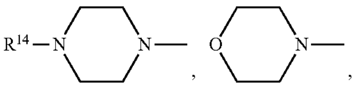 and 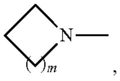
wherein 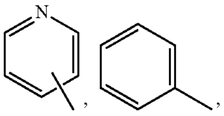 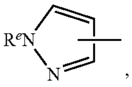 and
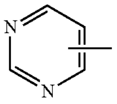
can be attached at any available position.
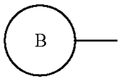

is preferably selected from the group consisting of

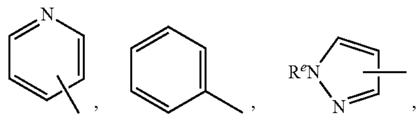

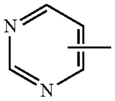

, wherein

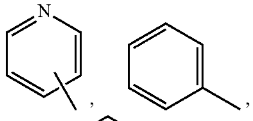

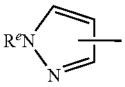

, and

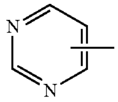

can be attached at any available position.

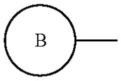

is more preferably selected from the group consisting of

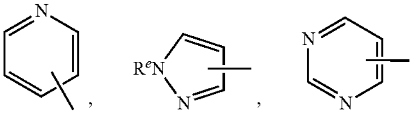

, wherein

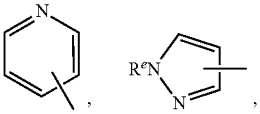

, and

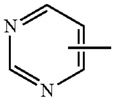

can be attached at any available position.

Examples of preferred groups include

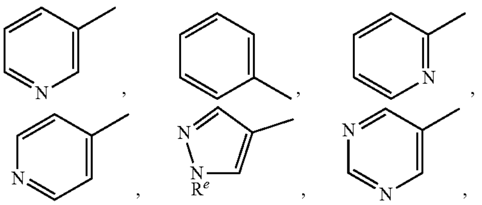

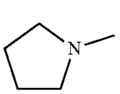

, and

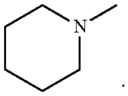

.

Examples of more preferred groups include

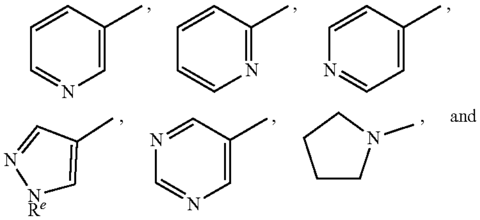

and

-continued

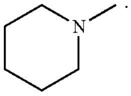

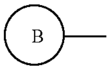

(including any of the preferred options thereof) can be optionally substituted by one or more substituents $R^B$.

In one embodiment,

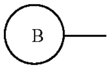

is

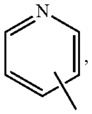

, wherein

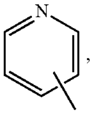

can be attached at any available position, and wherein

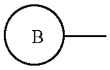

can be optionally substituted by one or more substituents $R^B$.

V is selected from the group consisting of S, $NR^a$ and $CR^bR^b$. Preferably V is S.

Z is selected from the group consisting of N and $CR^c$. In one embodiment Z is N. In another embodiment, Z is $CR^c$.

W is selected from the group consisting of N and $CR^c$ or W is C if W is attached to U.

$W^1$ is selected from the group consisting of N and $CR^c$ or $W^1$ is C if $W^1$ is attached to U.

X is selected from the group consisting of N and $CR^c$ or X is C if X is attached to U.

Y is selected from the group consisting of N and $CR^c$ or Y is C if Y is attached to U.

U is selected from the group consisting of —$NR^a$—, —CH═CH—, —C≡C— and a bond.

In a preferred embodiment of the present invention, at least one of Z, X, $W^1$, W and Y is N. More preferably, V is S and at least one of Z, X, $W^1$, W and Y is N.

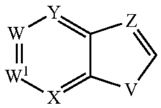

is preferably selected from the group consisting of

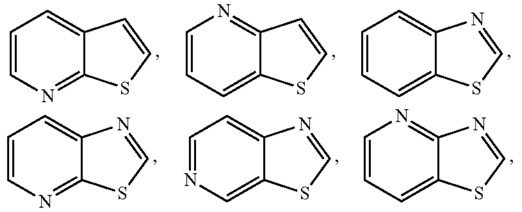

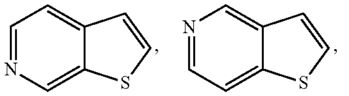

and

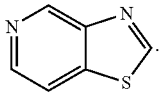

More preferably,

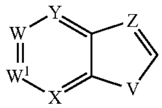

is selected from the group consisting of

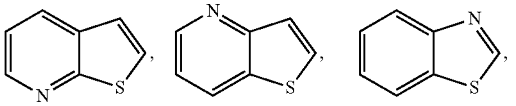

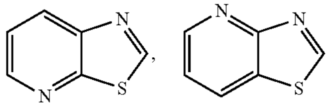

and

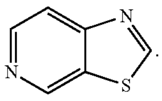

Even more preferably from

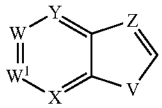

is preferred selected from the group consisting of

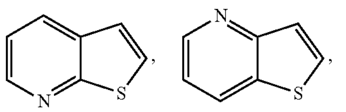

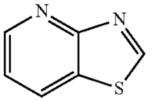

and

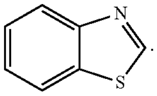

In a preferred embodiment,

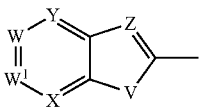

is selected from the from group consisting of

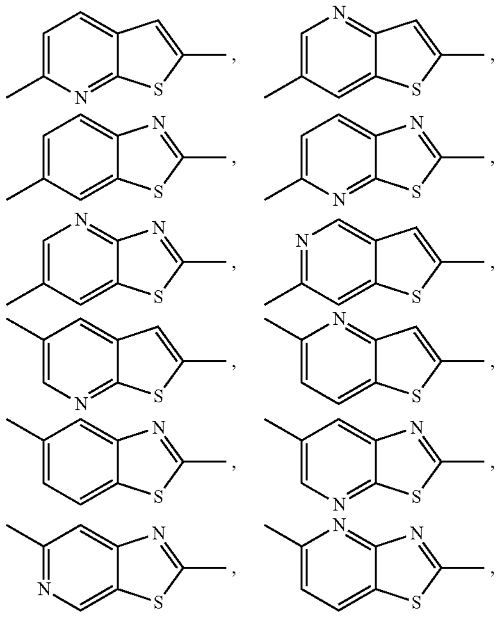

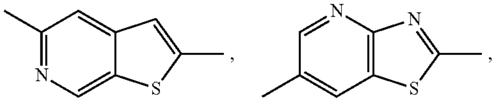

and

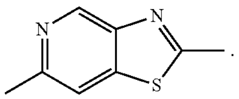

In a more preferred embodiment,

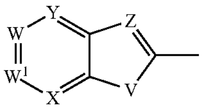

is selected from the group consisting of

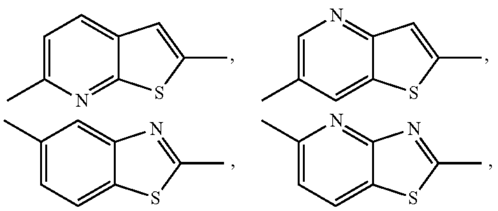

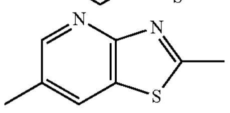

and

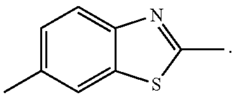

In a more preferred embodiment,

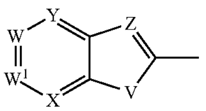

is selected from the group consisting of

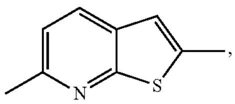
,
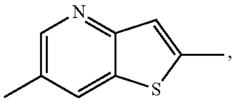
,
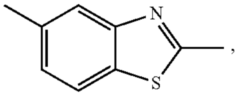
,
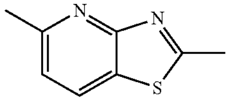
and
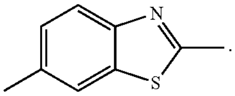
.

For each occurrence, $R^a$ is independently selected from the group consisting of hydrogen, alkyl, and haloalkyl. For each occurrence, $R^a$ is preferably independently selected from the group consisting of hydrogen, and alkyl.

For each occurrence, $R^b$ is independently selected from the group consisting of hydrogen, alkyl, haloalkyl, and halogen. For each occurrence, $R^b$ is preferably independently selected from the group consisting of hydrogen, and alkyl.

For each occurrence, $R^c$ is independently selected from the group consisting of hydrogen, alkyl, haloalkyl, and halogen. For each occurrence, $R^c$ is preferably hydrogen.

For each occurrence, $R^d$ is independently selected from the group consisting of -halogen, —OH, —O-alkyl and -hydrogen.

For each occurrence, $R^e$ is independently selected from the group consisting of hydrogen, $—(CH_2CH_2—O)_n—R^f$, $—(CH_2CH_2—O)_n—(CH_2CH_2)—R^d$, alkyl, carbocyclyl and heterocyclyl, wherein alkyl, carbocyclyl and heterocyclyl can be optionally substituted. For each occurrence, $R^e$ is preferably independently selected from the group consisting of hydrogen, and alkyl.

For each occurrence, $R^f$ is independently selected from the group consisting of hydrogen, and alkyl, wherein alkyl can be optionally substituted. For each occurrence, $R^f$ is preferably independently selected from the group consisting of hydrogen, and alkyl.

For each occurrence, $R^A$ is independently selected from the group consisting of halogen, —CN, $—O—R^{10}$, $—NR^{10}R^{11}$, $—CONR^{10}R^{11}$, $—N(R^{10})—C(O)—R^{11}$, $—N(R^{10})—C(O)—O—R^{11}$, $—(O—CH_2CH_2)_n—R^d$, =O, alkyl, carbocyclyl, carbocyclylalkyl, heterocyclyl, heterocyclylalkyl, alkenyl, and alkynyl. For each occurrence, $R^A$ is preferably independently selected from the group consisting of halogen, —CN, $—O—R^{10}$, $—NR^{10}R^{11}$, $—CONR^{10}R^{11}$, $—N(R^{10})—C(O)—R^{11}$, $—N(R^{10})—C(O)—O—R^{11}$, $—(O—CH_2CH_2)_n—R^d$, =O, alkyl, carbocyclyl, carbocyclylalkyl, heterocyclyl, and heterocyclylalkyl. For each occurrence, $R^A$ is more preferably independently selected from the group consisting of halogen, —CN, $—O—R^{10}$, $—NR^{10}R^{11}$, $—N(R^{10})—C(O)—O—R^{11}$, $—(O—CH_2CH_2)_n—R^d$, =O, alkyl, and heterocyclyl. In a preferred embodiment, $R^A$ is selected from halogen, $—O(CH_2)_2F$, $—O(CH_2)_2OH$, optionally substituted morpholino, optionally substituted-pyrrolidine (such as F-pyrrolidine), and optionally substituted-piperidine (such as F-piperidine), more preferably $R^A$ is optionally substituted-pyrrolidine (such as F-pyrrolidine) or optionally substituted-piperidine (such as F-piperidine). In a preferred embodiment, $R^A$ is an optionally substituted-pyrrolidine (such as F-pyrrolidine).

The alkyl, carbocyclyl, carbocyclylalkyl, heterocyclyl, heterocyclylalkyl, alkenyl, and alkynyl can be optionally substituted. Examples of possible substituents of the alkyl group include -Hal, —CN, —OH, —O-alkyl, $—CF_3$, and $—OCF_3$. Examples of possible substituents of the carbocyclyl, carbocyclylalkyl, heterocyclyl, heterocyclylalkyl, alkenyl, and alkynyl include -Hal, —CN, —OH, —O-alkyl, $—CF_3$, $—OCF_3$, and alkyl.

If more than one group $R^A$ is present and two of the groups $R^A$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted. Examples of the 5- to 8-membered ring include $—O—CH_2—CH_2—O—$ and $—O—CH_2—O—$.

For each occurrence, $R^B$ is independently selected from the group consisting of halogen, —CN, $—O—R^{10}$, $—NR^{10}R^{11}$, $—CONR^{10}R^{11}$, $—N(R^{10})—C(O)—R^{11}$, $—N(R^{10})—C(O)—O—R^{11}$, $—(O—CH_2CH_2)_n—R^d$, =O, alkyl, carbocyclyl, carbocyclylalkyl, heterocyclyl, heterocyclylalkyl, alkenyl, and alkynyl. For each occurrence, $R^B$ is preferably independently selected from the group consisting of halogen, —CN, $—O—R^{10}$, $—NR^{10}R^{11}$, $—CONR^{10}R^{11}$, $—N(R^{10})—C(O)—R^{11}$, $—N(R^{10})—C(O)—O—R^{11}$, $—(O—CH_2CH_2)_n—R^d$, alkyl, carbocyclyl, carbocyclylalkyl, heterocyclyl, and heterocyclylalkyl. For each occurrence, $R^B$ is more preferably independently selected from the group consisting of halogen, —CN, $—O—R^{10}$, $—NR^{10}R^{11}$, $—N(R^{10})—C(O)—O—R^{11}$, $—(O—CH_2CH_2)_n—R^d$, alkyl, and heterocyclyl. In a preferred embodiment, $R^B$ is selected from halogen, $—O—R^{10}$, $—O(CH_2)_2F$, $—NR^{10}R^{11}$, $—N(R^{10})—C(O)—O—R^{11}$, optionally substituted piperidine, optionally substituted pyrrolidone, optionally substituted tetrahydropyrane, and optionally substituted azaspiro[3.3]heptane (with $R^{10}$ and $R^{11}$ being independently hydrogen or alkyl). In a more preferred embodiment, $R^B$ is an optionally substituted-pyrrolidine and an optionally substituted-piperidine.

The alkyl, carbocyclyl, carbocyclylalkyl, heterocyclyl, heterocyclylalkyl, alkenyl, and alkynyl can be optionally substituted. Examples of possible substituents of the alkyl group include -Hal, —CN, —OH, —O-alkyl, $—CF_3$, and $—OCF_3$. Examples of possible substituents of the carbocyclyl, carbocyclylalkyl, heterocyclyl, heterocyclylalkyl, alkenyl, and alkynyl include -Hal, —CN, —OH, —O-alkyl, $—CF_3$, $—OCF_3$, and alkyl.

If more than one group $R^B$ is present and two of the groups $R^B$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted. Examples of the 5- to 8-membered ring include $—O—CH_2—CH_2—O—$ and $—O—CH_2—O—$.

For each occurrence, $R^{10}$ is independently selected from the group consisting of hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted. For each occurrence, $R^{10}$ is preferably independently selected from the group consisting of hydrogen, and alkyl. Examples of the optional substituents include —OH, —O-alkyl and Hal.

For each occurrence, $R^{11}$ is independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted. For each occurrence, $R^{11}$ is preferably independently selected from the group consisting of hydrogen, and alkyl. Examples of the optional substituents include —OH, —O-alkyl and Hal.

For each occurrence, $R^{14}$ is independently selected from the group consisting of hydrogen, $-(CH_2CH_2-O)_n-R^f$, $-(CH_2CH_2-O)_n-(CH_2CH_2)-R^d$, alkyl, carbocyclyl and heterocyclyl, wherein alkyl, carbocyclyl and heterocyclyl can be optionally substituted. For each occurrence, $R^{14}$ is preferably independently selected from the group consisting of hydrogen, and alkyl. Examples of the optional substituents include —OH, —O-alkyl and Hal.

For each occurrence, n is independently 1 to 4; preferably for each occurrence n is 1 or 2.

For each occurrence, m is independently 1 to 4, preferably for each occurrence, m is 2 or 3.

Preferred compounds of formula (I) are the compounds given in the example section of the present application. Particularly preferred compounds are

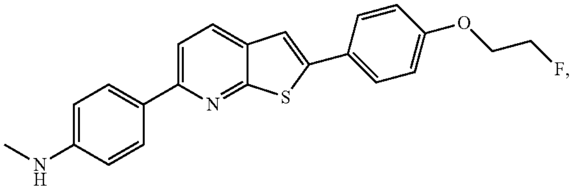

,

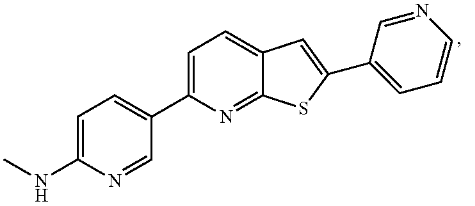

,

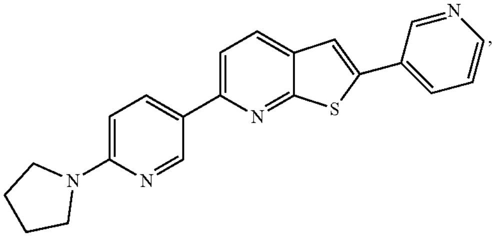

,

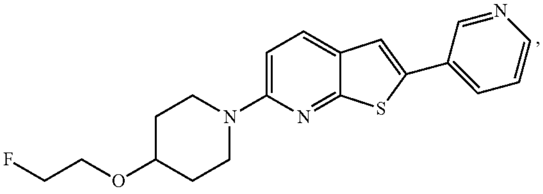

,

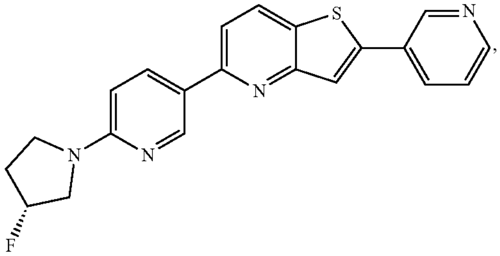

,

-continued

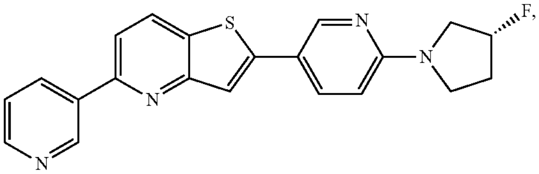

,

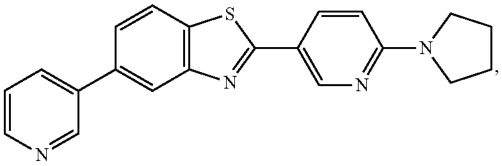

,

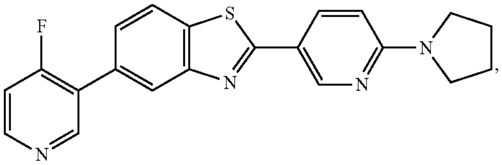

,

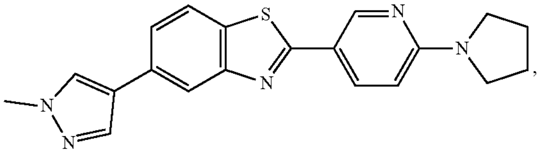

,

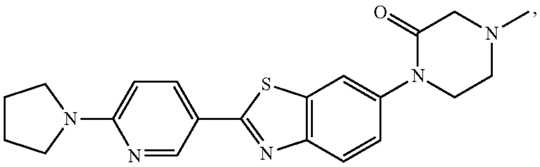

,

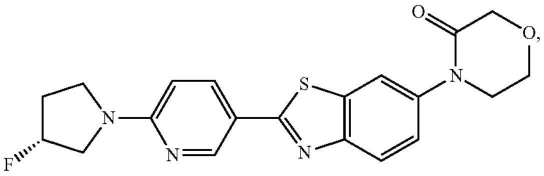

,

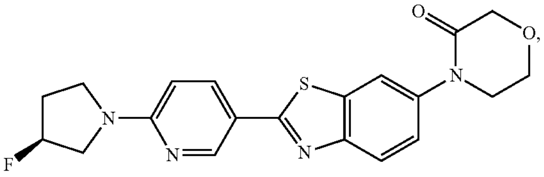

,

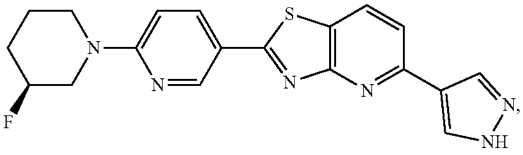

,

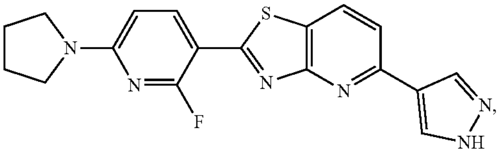

,

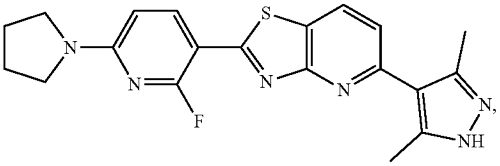

-continued
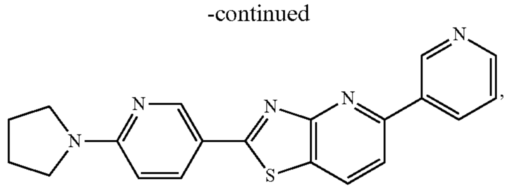,
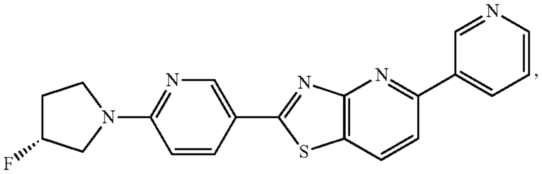,
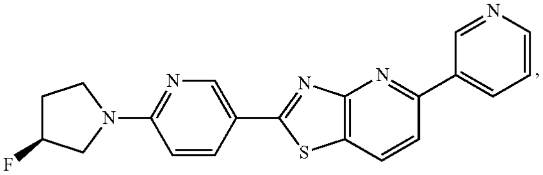,
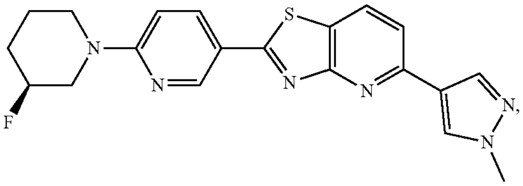,
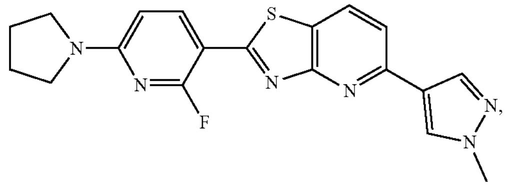,
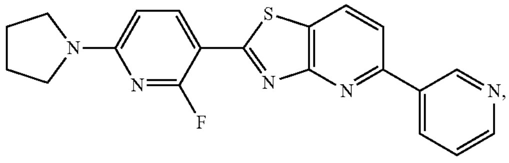,
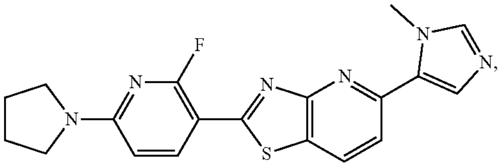,
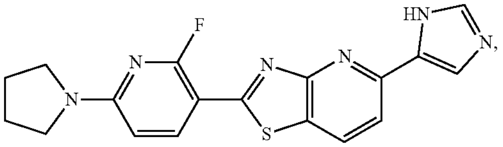,
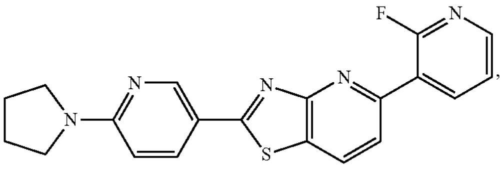,
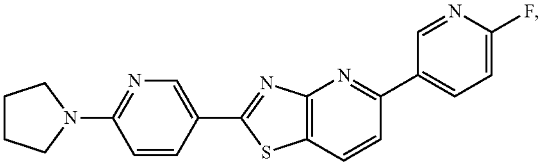,
-continued
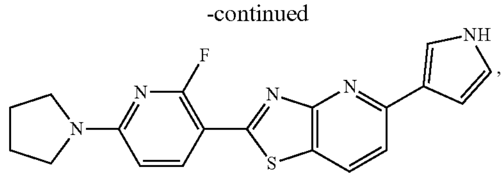,
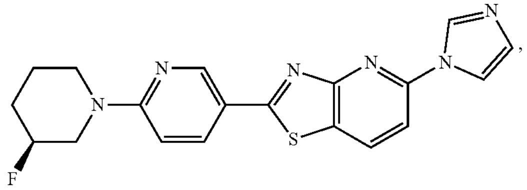,
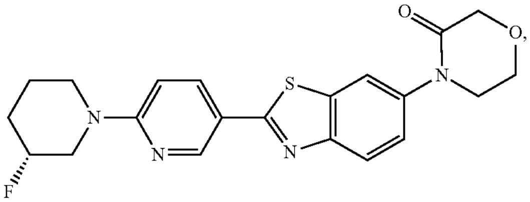,
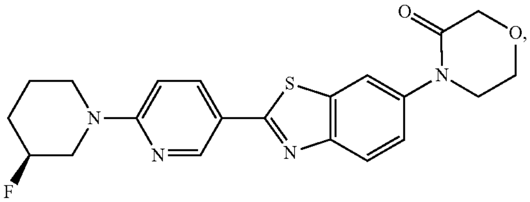,
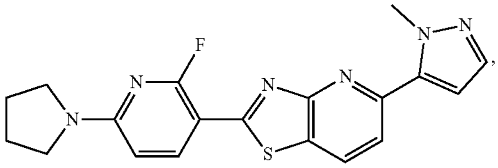,
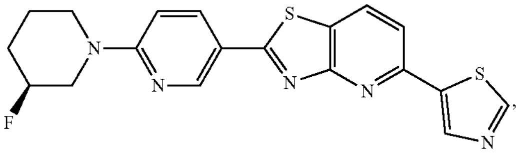,
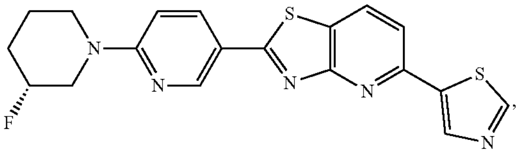,
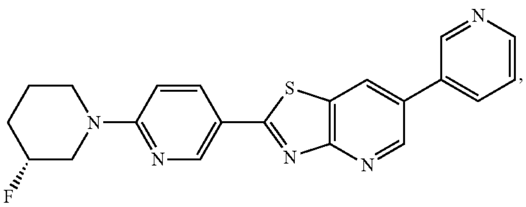,
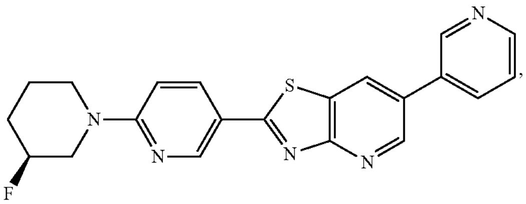, -continued
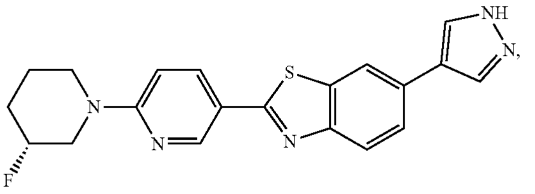
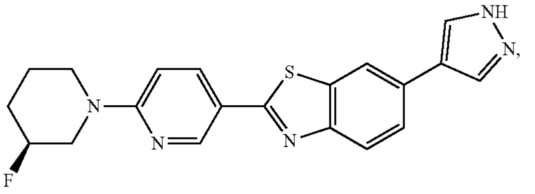
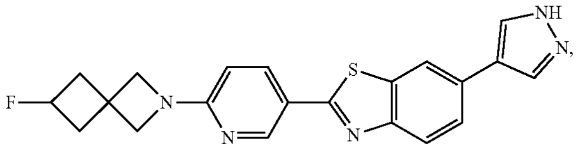
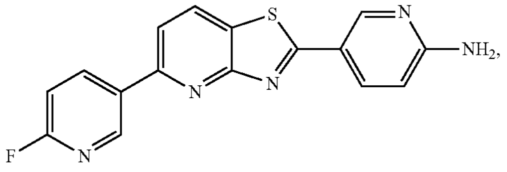
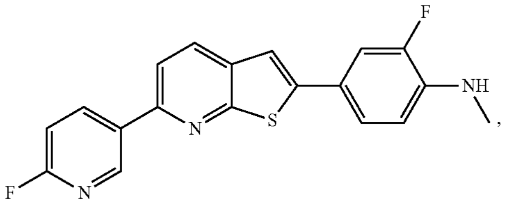
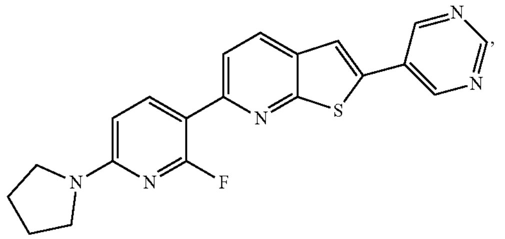
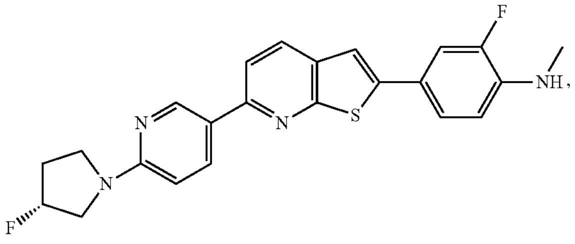
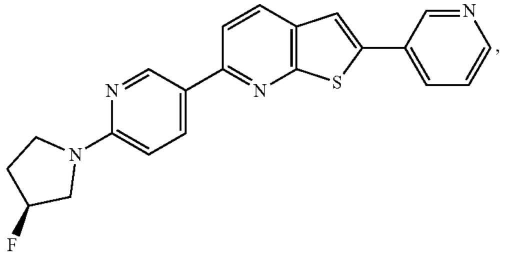
-continued
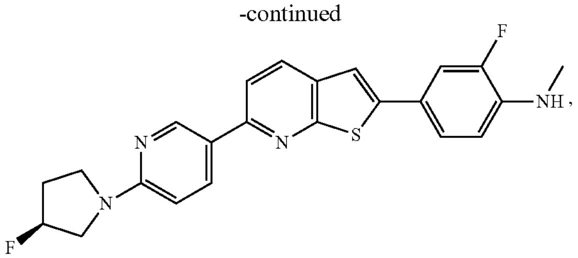
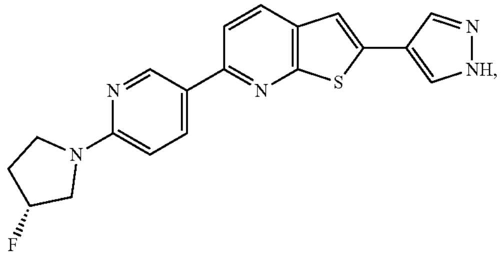
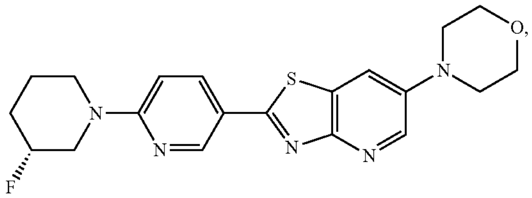
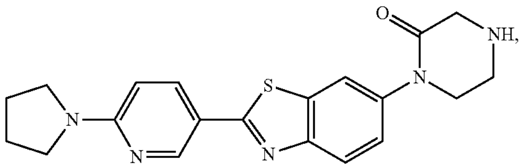
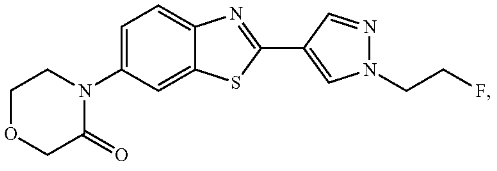
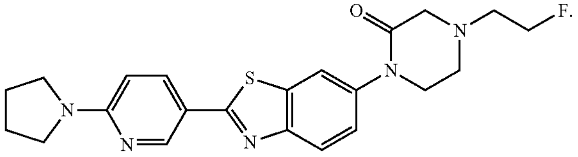
In a further embodiment, the present invention refers to a compound of formula (II):
(II)
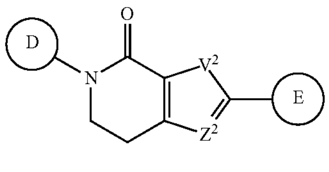
and all detectably labeled derivatives, stereoisomers, racemic mixtures, pharmaceutically acceptable salts, hydrates, solvates, prodrugs and polymorphs thereof.

Another preferred embodiment of the compound of formula (II) is selected from

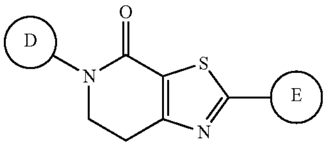

(IIa)

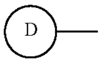

is selected from the group consisting of

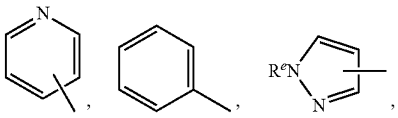

hydrogen and alkyl, wherein

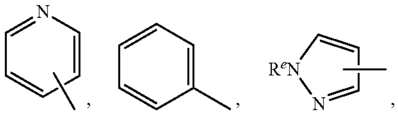

and alkyl can be attached at any available position.

In one embodiment,

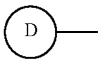

is hydrogen.

In an other embodiment,

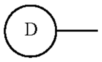

is selected from the group consisting of

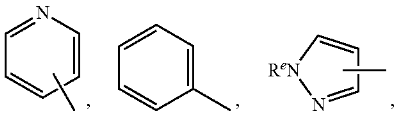

and alkyl, wherein

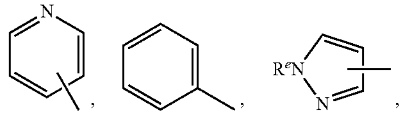

and alkyl can be attached at any available position. Preferably,

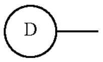

is

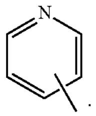

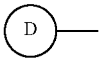

can be optionally substituted by one or more substituents $R^D$.

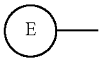

is selected from the group consisting of

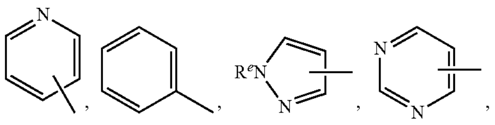

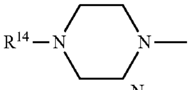 , 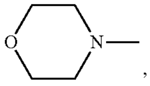 , and 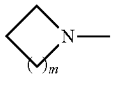 , wherein 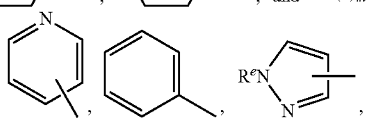 , and

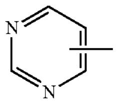

can be attached at any available position.

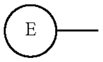

is preferably selected from the group consisting of

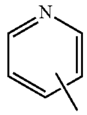, 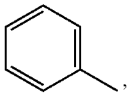, 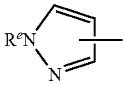,

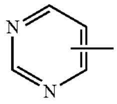, wherein 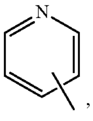, 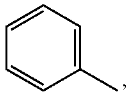,

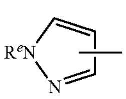, and 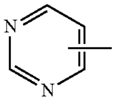

can be attached at any available position.

Examples of preferred groups include

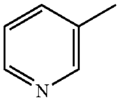, 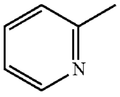, 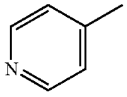, 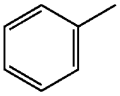,

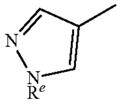, 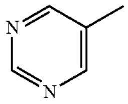, 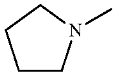, and

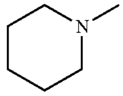.

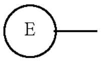

(including any of the preferred options thereof) can be optionally substituted by one or more substituents $R^E$. Examples of preferred substituted groups include an optionally substituted heterocyclyl, particularly an optionally substituted-pyrrolidine.

In one embodiment

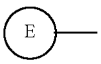

is

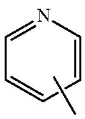, wherein

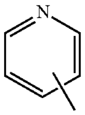, can be attached at any available position, and wherein

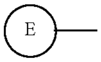

can be optionally substituted by one or more substituents $R^E$.

$V^2$ is selected from the group consisting of S, $NR^a$ and $CR^bR^b$. Preferably $V^2$ is S.

$Z^2$ is selected from the group consisting of N and $CR^c$. In one embodiment $Z^2$ is N. In another embodiment, $Z^2$ is $CR^c$.

For each occurrence, $R^a$ is independently selected from the group consisting of hydrogen, alkyl, and haloalkyl. For each occurrence, $R^a$ is preferably independently selected from the group consisting of hydrogen, and alkyl.

For each occurrence, $R^b$ is independently selected from the group consisting of hydrogen, alkyl, haloalkyl, and halogen. For each occurrence, $R^b$ is preferably independently selected from the group consisting of hydrogen, and alkyl.

For each occurrence, $R^c$ is independently selected from the group consisting of hydrogen, alkyl, haloalkyl, and halogen. For each occurrence, $R^c$ is preferably hydrogen.

For each occurrence, $R^d$ is independently selected from the group consisting of halogen, —OH, —O-alkyl and hydrogen.

For each occurrence, $R^e$ is independently selected from the group consisting of hydrogen, $—(CH_2CH_2—O)_n—R^f$, $—(CH_2CH_2—O)_n—(CH_2CH_2)—R^d$, alkyl, carbocyclyl and heterocyclyl, wherein alkyl, carbocyclyl and heterocyclyl can be optionally substituted. For each occurrence, $R^e$ is preferably independently selected from the group consisting of hydrogen, and alkyl.

For each occurrence, $R^f$ is independently selected from the group consisting of hydrogen, and alkyl, wherein alkyl can be optionally substituted. For each occurrence, $R^f$ is preferably independently selected from the group consisting of hydrogen, and alkyl.

For each occurrence, $R^D$ is independently selected from the group consisting of halogen, CN, $—O—R^{10}$, $—NR^{10}R^{11}$, $—CONR^{10}R^{11}$, $—N(R^{10})—C(O)—R^{11}$, $—N(R^{10})—C(O)—O—R^{11}$, $—(O—CH_2CH_2)_n—R^d$, =O, alkyl, carbocyclyl, carbocyclylalkyl, heterocyclyl, heterocyclylalkyl, alkenyl, and alkynyl.

If

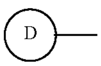

is selected from the group consisting of

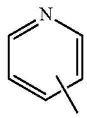, 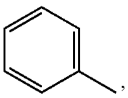, and 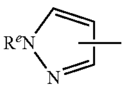, for each occurrence, $R^D$ is preferably independently selected from the group consisting of halogen, CN, —O—$R^{10}$, —$NR^{10}R^{11}$, —$CONR^{10}R^{11}$, —N($R^{10}$)—C(O)—$R^{11}$, —N($R^{10}$)—C(O)—O—$R^{11}$, —(O—$CH_2CH_2$)$_n$—$R^d$, ═O, alkyl, carbocyclyl, carbocyclylalkyl, heterocyclyl, heterocyclylalkyl, alkenyl, and alkynyl. For each occurrence, $R^D$ is more preferably independently selected from the group consisting of halogen, —CN, —O—$R^{10}$, —$NR^{10}R^{11}$, —$CONR^{10}R^{11}$, —N($R^{10}$)—C(O)—$R^{11}$, —N($R^{10}$)—C(O)—O—$R^{11}$, —(O—$CH_2CH_2$)$_n$—$R^d$, alkyl, carbocyclyl, carbocyclylalkyl, heterocyclyl, and heterocyclylalkyl. For each occurrence, $R^D$ is even more preferably independently selected from the group consisting of halogen, —CN, —O—$R^{10}$, —$NR^{10}R^{11}$, —N($R^{10}$)—C(O)—O—$R^{11}$, —(O—$CH_2CH_2$)$_n$—$R^d$, alkyl, and heterocyclyl.

If

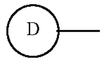

is alkyl, for each occurrence, $R^D$ is preferably independently selected from the group consisting of halogen, CN, —O—$R^{10}$, —$NR^{10}R^{11}$, —$CONR^{10}R^{11}$, —N($R^{10}$)—C(O)—$R^{11}$, —N($R^{10}$)—C(O)—O—$R^{11}$, —(O—$CH_2CH_2$)$_n$—$R^d$, ═O, carbocyclyl, carbocyclylalkyl, heterocyclyl, heterocyclylalkyl, alkenyl, and alkynyl. For each occurrence, $R^D$ is more preferably independently selected from the group consisting of halogen, —CN, —O—$R^{10}$, —$NR^{10}R^{11}$, —$CONR^{10}R^{11}$, —N($R^{10}$)—C(O)—$R^{11}$, —N($R^{10}$)—C(O)—O—$R^{11}$, —(O—$CH_2CH_2$)$_n$—$R^d$, carbocyclyl, carbocyclylalkyl, heterocyclyl, and heterocyclylalkyl. For each occurrence, $R^D$ is even more preferably independently selected from the group consisting of halogen, —CN, —O—$R^{10}$, —$NR^{10}R^{11}$, —N($R^{10}$)—C(O)—O—$R^{11}$, —(O—$CH_2CH_2$)$_n$—$R^d$, and heterocyclyl.

The alkyl, carbocyclyl, carbocyclylalkyl, heterocyclyl, heterocyclylalkyl, alkenyl, and alkynyl can be optionally substituted. Examples of possible substituents of the alkyl group include -Hal, —CN, —OH, —O-alkyl, —$CF_3$, and —$OCF_3$. Examples of possible substituents of the carbocyclyl, carbocyclylalkyl, heterocyclyl, heterocyclylalkyl, alkenyl, and alkynyl include -Hal, —CN, —OH, —O-alkyl, —$CF_3$, —$OCF_3$, and alkyl.

If more than one group $R^D$ is present and two of the groups $R^D$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted.

For each occurrence, $R^E$ is independently selected from the group consisting of halogen, CN, —O—$R^{10}$, —$NR^{10}R^{11}$, —$CONR^{10}R^{11}$, —N($R^{10}$)—C(O)—$R^{11}$, —N($R^{10}$)—C(O)—O—$R^{11}$, —(O—$CH_2CH_2$)$_n$—$R^d$, ═O, alkyl, carbocyclyl, carbocyclylalkyl, heterocyclyl, heterocyclylalkyl, alkenyl, and alkynyl. For each occurrence, $R^E$ is preferably independently selected from the group consisting of halogen, —CN, —O—$R^{10}$, —$NR^{10}R^{11}$, —$CONR^{10}R^{11}$, —N($R^{10}$)—C(O)—$R^{11}$, —N($R^{10}$)—C(O)—O—$R^{11}$, —(O—$CH_2CH_2$)$_n$—$R^d$, alkyl, carbocyclyl, carbocyclylalkyl, heterocyclyl, and heterocyclylalkyl. For each occurrence, $R^E$ is more preferably independently selected from the group consisting of halogen, —CN, —O—$R^{10}$, —$NR^{10}R^{11}$, —N($R^{10}$)—C(O)—O—$R^{11}$, —(O—$CH_2CH_2$)$_n$—$R^d$, alkyl, and heterocyclyl. Even more preferably, $R^E$ is halogen and/or F-pyrrolidine.

The alkyl, carbocyclyl, carbocyclylalkyl, heterocyclyl, heterocyclylalkyl, alkenyl, and alkynyl can be optionally substituted. Examples of possible substituents of the alkyl group include -Hal, —CN, —OH, —O-alkyl, —$OF_3$, and —$OCF_3$. Examples of possible substituents of the carbocyclyl, carbocyclylalkyl, heterocyclyl, heterocyclylalkyl, alkenyl, and alkynyl include -Hal, —CN, —OH, —O-alkyl, —$CF_3$, —$OCF_3$, and alkyl.

If more than one group $R^E$ is present and two of the groups $R^E$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted.

For each occurrence, $R^{10}$ is independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted. For each occurrence, $R^{10}$ is preferably independently selected from the group consisting of hydrogen, and alkyl. Examples of the optional substituents include —OH, —O-alkyl and Hal.

For each occurrence, $R^{11}$ is independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted. For each occurrence, $R^{11}$ is preferably independently selected from the group consisting of hydrogen, and alkyl. Examples of the optional substituents include —OH, —O-alkyl and Hal.

For each occurrence, $R^{14}$ is independently selected from the group consisting of hydrogen, —($CH_2CH_2$—O)$_n$—$R^f$, —($CH_2CH_2$—O)$_n$—($CH_2CH_2$)—$R^d$, alkyl, carbocyclyl and heterocyclyl, wherein alkyl, carbocyclyl and heterocyclyl can be optionally substituted. For each occurrence, $R^{14}$ is preferably independently selected from the group consisting of hydrogen, and alkyl. Examples of the optional substituents include —OH, —O-alkyl and Hal.

For each occurrence, n is independently 1 to 4; preferably for each occurrence n is 1 or 2.

For each occurrence, m is independently 1 to 4, preferably for each occurrence, m is 2 or 3.

Preferred compounds of formula (II) are the compounds given in the example section of the present application. Particularly preferred compounds are

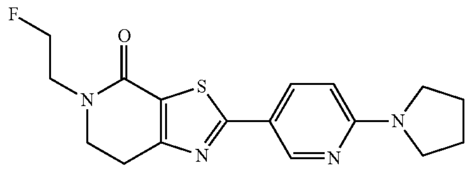

,

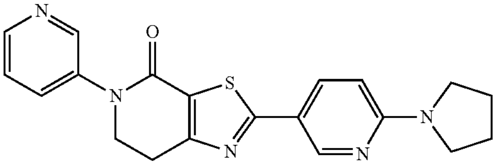

The compounds of the present invention can be detectably labeled. The type of the label is not specifically limited and will depend on the detection method chosen. Examples of possible labels include isotopes such as radionuclides, positron emitters, gamma emitters, as well as fluorescent, luminescent and chromogenic labels. With respect to the detectably labeled compounds of the present invention which include a radioisotope, a positron emitter, or a gamma emitter, it is to be understood that the radioisotope, positron emitter, or gamma emitter is to be present in an amount which is not identical to the natural amount of the respective radioisotope, positron emitter, or gamma emitter. Furthermore, the employed amount should allow detection thereof by the chosen detection method.

Examples of suitable isotopes such as radionuclides, positron emitters and gamma emitters include $^{2}H$, $^{3}H$, $^{18}F$, $^{123}I$, $^{124}I$, $^{125}I$, $^{131}I$, $^{11}C$, $^{13}N$, $^{15}O$, and $^{77}Br$, preferably $^{2}H$, $^{3}H$, $^{11}C$, $^{13}N$, $^{15}O$, and $^{18}F$, more preferably $^{2}H$, $^{3}H$ and $^{18}F$, even more preferably $^{18}F$.

$^{18}F$-labeled compounds are particularly suitable for imaging applications such as PET. The corresponding compounds which include fluorine having a natural $^{19}F$ isotope are also of particular interest as they can be used as analytical standards and references during manufacturing, quality control, release and clinical use of their $^{18}F$-analogs.

Further, substitution with isotopes such as deuterium, i.e., $^{2}H$, may afford certain diagnostic and therapeutic advantages resulting from greater metabolic stability by reducing for example defluorination, increased in vivo half-life or reduced dosage requirements, while keeping or improving the original compound efficacy.

Isotopic variations of the compounds of the invention can generally be prepared by conventional procedures such as by the illustrative methods or by the preparations described in the Examples and Preparative Examples hereafter using appropriate isotopic variations of suitable reagents, commercially available or prepared by known synthetic techniques.

Radionuclides, positron emitters and gamma emitters can be included into the compounds of the present invention by methods which are usual in the field of organic synthesis. Typically, they will be introduced by using a correspondingly labeled starting material when the desired compound of the present invention is prepared. Illustrative methods of introducing detectable labels are described, for instance, in US 2012/0302755.

The position at which the detectable label is to be attached to the compounds of the present invention is not particularly limited.

The radionuclides, positron emitters and gamma emitters, for example, can be attached at any position where the corresponding non-emitting atom can also be attached. For instance, $^{18}F$ can be attached at any position which is suitable for attaching F. The same applies to the other radionuclides, positron emitters and gamma emitters. Due to the ease of synthesis, it is preferred to attach $^{18}F$, $^{123}I$, $^{124}I$, $^{125}I$, $^{131}I$, and $^{77}Br$ as $R^A$, $R^B$, $R^D$ and $R^E$ or part of $R^A$, $R^B$, $R^D$ and $R^E$. If $^{3}H$ is employed as a detectable label it is preferably attached in the form of $—C(^{3}H)_3$ at any position at which a methyl group can be attached. Alternatively, $^{3}H$ per se can be attached at any available position. If $^{2}H$ is employed as a detectable label it is preferably attached in the form of $—C(^{2}H)_3$ at any position at which a methyl group can be attached. Easily available positions include $R^e$ and $R^{14}$. $^{11}C$, $^{13}N$, and $^{15}O$ can be incorporated into the compounds of the present invention at any position where C, N and O appear.

Diagnostic Compositions

The compounds of the present invention are particularly suitable for imaging of alpha-synuclein aggregates including, but not limited to, Lewy bodies and/or Lewy neurites. With respect to alpha-synuclein protein, compounds of the present invention are particularly suitable for binding to various types of alpha-synuclein aggregates including, but not limited to, Lewy bodies and/or Lewy neurite.

Due to their design and to the binding characteristics, the compounds of the present invention are suitable for use in the diagnosis of disorders and abnormalities associated with alpha-synuclein aggregates including, but not limited to, Lewy bodies and/or Lewy neurites. The compounds of the present invention are particularly suitable for positron emission tomography imaging of alpha-synuclein aggregates including, but not limited to, Lewy bodies and/or Lewy neurites. Diseases involving alpha-synuclein aggregates are generally listed as synucleinopathies (or α-synucleinopathies). The compounds of the present invention are suitable for use in the diagnosis of disorders including, but not limited to, Parkinson's disease (sporadic, familial with alpha-synuclein mutations, familial with mutations other than alpha-synuclein, pure autonomic failure and Lewy body dysphagia), dementia with Lewy bodies ("pure" Lewy body dementia), sporadic Alzheimer's disease, familial Alzheimer's disease with APP mutations, familial Alzheimer's disease with PS-1, PS-2 or other mutations, familial British dementia, Lewy body variant of Alzheimer's disease and normal aging (Down syndrome). Synucleinopathies with neuronal and glial aggregates of alpha synuclein include multiple system atrophy (Shy-Drager syndrome, striatonigral degeneration and olivopontocerebellar atrophy). Other diseases that may have alpha-synuclein-immunoreactive lesions include traumatic brain injury, chronic traumatic encephalopathy, tauopathies (Pick's disease, frontotemporal dementia, progressive supranuclear palsy, corticobasal degeneration and Niemann-Pick type C1 disease), motor neuron disease, amyotrophic lateral sclerosis (sporadic, familial and ALS-dementia complex of Guam), neuroaxonal dystrophy, neurodegeneration with brain iron accumulation type 1 (Hallervorden-Spatz syndrome), prion diseases, ataxia telangiectatica, Meige's syndrome, subacute sclerosing panencephalitis, Gaucher disease as well as other lysosomal storage disorders (including Kufor-Rakeb syndrome and Sanfilippo syndrome) and rapid eye movement (REM) sleep behavior disorder. (Jellinger, Mov Disord 2003, 18 Suppl. 6, S2-12; Galvin et al. JAMA Neurology 2001, 58 (2), 186-190; Kovari et al., Acta Neuropathol. 2007, 114(3), 295-8; Saito et al., J Neuropathol Exp Neurol. 2004, 63(4), 323-328; McKee et al., Brain, 2013, 136(Pt 1), 43-64; Puschmann et al., Parkinsonism Relat Disord 2012, 18S1, S24-S27; Usenovic et al., J Neurosci. 2012, 32(12), 4240-4246; Winder-Rhodes et al., Mov Disord. 2012, 27(2), 312-315; Ferman et al., J Int Neuropsychol Soc. 2002, 8(7), 907-914). Preferably, the compounds of the present invention are suitable for use in the diagnosis of Parkinson's disease (PD).

In the methods of diagnosing a disorder or abnormality associated with alpha-synuclein aggregates including, but not limited to, Lewy bodies and/or Lewy neurites, such as Parkinson's disease, or a predisposition therefor in a subject, the method comprising:

a) administering to the subject a diagnostically effective amount of a compound of the present invention;

b) allowing the compound of the present invention to distribute into the tissue of interest (such as brain tissue, or body fluids such as cerebrospinal fluid (CSF)); and c) imaging the tissue of interest, wherein an increase in binding of the compound of the present invention to the tissue of interest compared to a normal control level of binding indicates that the subject is suffering from or is at risk of developing a disorder or abnormality associated with alpha-synuclein aggregates including, but not limited to, Lewy bodies and/or Lewy neurites.

The compounds of the present invention can be used for imaging of alpha-synuclein aggregates including, but not limited to, Lewy bodies and/or Lewy neurites in any sample or a specific body part or body area of a patient which suspected to contain an alpha-synuclein aggregates including, but not limited to, Lewy bodies and/or Lewy neurites. The compounds of the present invention are able to pass the blood-brain barrier. Consequently, they are particularly suitable for imaging of alpha-synuclein aggregates including, but not limited to, Lewy bodies and/or Lewy neurites in the brain, as well as in body fluids such as cerebrospinal fluid (CSF).

In diagnostic applications, the compound of the present invention is preferably administered in a diagnostic composition comprising the compound of the invention. A "diagnostic composition" is defined in the present invention as a composition comprising one or more compounds of the present invention in a form suitable for administration to a patient, e.g., a mammal such as a human, and which is suitable for use in the diagnosis of the specific disorder or anormality at issue. Preferably a diagnostic composition further comprises a physiologically acceptable carrier, diluent, adjuvant or excipient. Administration is preferably carried out as defined below. More preferably by injection of the composition as an aqueous solution. Such a composition may optionally contain further ingredients such as buffers; pharmaceutically acceptable solubilisers (e.g., cyclodextrins or surfactants such as Pluronic, Tween or phospholipids); and pharmaceutically acceptable stabilisers or antioxidants (such as ascorbic acid, gentisic acid or para-aminobenzoic acid). The dose of the compound of the present invention will vary depending on the exact compound to be administered, the weight of the patient, and other variables as would be apparent to a physician skilled in the art.

While it is possible for the compounds of the present invention to be administered alone, it is preferable to formulate them into a diagnostic composition in accordance with standard pharmaceutical practice. Thus, the invention also provides a diagnostic composition which comprises a diagnostically effective amount of a compound of the present invention in admixture with a pharmaceutically acceptable carrier, diluent, adjuvant or excipient.

Pharmaceutically acceptable excipients are well known in the pharmaceutical art, and are described, for example, in Remington's Pharmaceutical Sciences, 15$^{th}$ Ed., Mack Publishing Co., New Jersey (1975). The pharmaceutical excipient can be selected with regard to the intended route of administration and standard pharmaceutical practice. The excipient must be acceptable in the sense of being not deleterious to the recipient thereof.

Pharmaceutically useful excipients that may be used in the formulation of the diagnostic composition of the present invention may comprise, for example, carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium stearate, talc, monosaccharides, disaccharides, starch, gelatin, cellulose, methylcellulose, sodium carboxymethyl cellulose, dextrose, hydroxypropyl-1-cyclodextrin, polyvinylpyrrolidone, low melting waxes, and ion exchange resins.

The routes for administration (delivery) of the compounds of the invention include, but are not limited to, one or more of: oral (e.g. as a tablet, capsule, or as an ingestible solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

For example, the compounds can be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Preferably, in diagnostic applications, the compounds of the present invention are administered parenterally. If the compounds of the present invention are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds; and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

As indicated, the compounds of the present invention can be administered intranasally or by inhalation and are conveniently delivered in the form of a dry powder inhaler or an aerosol spray presentation from a pressurized container, pump, spray or nebulizer with the use of a suitable propellant, e.g. dichlorodifluoromethane, trichlorofluoromethane, dichlorotetrafluoroethane, a hydrofluoroalkane such as 1,1, 1,2-tetrafluoroethane (HFA134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the compound and a suitable powder base such as lactose or starch.

Alternatively, the compounds of the present invention can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

They may also be administered by the pulmonary or rectal routes. They may also be administered by the ocular route. For ophthalmic use, the compounds can be formulated as micronized suspensions in isotonic, pH was adjusted, sterile saline, or, preferably, as solutions in isotonic, pH was adjusted, sterile saline, optionally in combination with a preservative such as a benzylalkonium chloride. Alternatively, they may be formulated in an ointment such as petrolatum.

For application topically to the skin, the compounds of the present invention can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing diagnosis.

Generally, the dose could preferably lie in the range 0.001 μg/kg to 10 μg/kg, preferably 0.01 μg/kg to 1.0 μg/kg. The dose will depend on the route of administration. It will be appreciated that it may be necessary to make routine variations to the dosage depending on the age and weight of the patient as well as the severity of the disorder or abnormality. The precise dose and route of administration will ultimately be at the discretion of the attendant physician or veterinarian.

The diagnostic compositions of the invention can be produced in a manner known per se to the skilled person as described, for example, in Remington's Pharmaceutical Sciences, $15^{th}$ Ed., Mack Publishing Co., New Jersey (1975).

The compounds of the present invention are useful as an in vitro analytical reference or an in vitro screening tool. They are also useful in in vivo diagnostic methods.

The compounds according to the present invention can also be provided in the form of a mixture comprising a compound according to the present invention and at least one compound selected from an imaging agent different from the compound according to the invention, a pharmaceutically acceptable carrier, a diluent and an excipient. The imaging agent different from the compound according to the invention is preferably present in a diagnostically effective amount. More preferably the imaging agent different from the compound according to the invention is an abeta or tau imaging agent.

Diagnosis of a disorder or abnormality associated with alpha-synuclein aggregates including, but not limited to, Lewy bodies and/or Lewy neurites or of a predisposition to a disorder or abnormality associated with alpha-synuclein aggregates including, but not limited to, Lewy bodies and/or Lewy neurites in a patient may be achieved by detecting the specific binding of a compound according to the invention to the alpha-synuclein aggregates including, but not limited to, Lewy bodies and/or Lewy neurites in a sample or in situ, which includes:

(a) bringing the sample or a specific body part or body area suspected to contain the alpha-synuclein aggregates including, but not limited to, Lewy bodies and/or Lewy neurites into contact with a compound of the invention which binds the alpha-synuclein aggregates including, but not limited to, Lewy bodies and/or Lewy neurites, (b) allowing the compound of the invention to bind to the alpha-synuclein aggregates including, but not limited to, Lewy bodies and/or Lewy neurites to form a compound/(alpha-synuclein aggregates including, but not limited to, Lewy bodies or Lewy neurites) complex (hereinafter "compound/(alpha-synuclein aggregates including, but not limited to, Lewy bodies and/or Lewy neurites) complex" will be abbreviated as "compound/protein aggregate complex"), (c) detecting the formation of the compound/protein aggregate complex, (d) optionally correlating the presence or absence of the compound/protein aggregate complex with the presence or absence of alpha-synuclein aggregates including, but not limited to, Lewy bodies and/or Lewy neurites in the sample or specific body part or area, and (e) optionally comparing the amount of the compound/protein aggregate complex to a normal control value, wherein an increase in the amount of the compound/protein aggregate complex compared to a normal control value may indicate that the patient is suffering from or is at risk of developing a disorder or abnormality associated with alpha-synuclein aggregates including, but not limited to, Lewy bodies and/or Lewy neurites.

The compound of the present invention can be brought into contact with the sample or the specific body part or body area suspected to contain the alpha-synuclein aggregates including, but not limited to, Lewy bodies and/or Lewy neurites by a suitable method. In in vitro methods the compound of the present invention and a liquid sample can be simply mixed. In in vivo tests the compound of the present invention is typically administered to the patient by any suitable means. These routes of administration include, but are not limited to, one or more of: oral (e.g. as a tablet, capsule, or as an ingestible solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual. In some instances, parenteral administration can be preferred.

After the sample or a specific body part or body area has been brought into contact with the compound of the present invention, the compound is allowed to bind to the alpha-synuclein aggregates including, but not limited to, Lewy bodies and/or Lewy neurites. The amount of time required for binding will depend on the type of test (e.g., in vitro or in vivo) and can be determined by a person skilled in the field by routine experiments.

The compound which has bound to the alpha-synuclein aggregates including, but not limited to, Lewy bodies and/or Lewy neurites, can be subsequently detected by any appropriate method. The specific method chosen will depend on the detectable label which has been chosen. Examples of possible methods include, but are not limited to, a fluorescence imaging technique or a nuclear imaging technique such as positron emission tomography (PET), single photon emission computed tomography (SPECT), magnetic resonance imaging (MRI), and contrast-enhanced magnetic resonance imaging (MRI). These have been described and enable visualization of amyloid biomarkers. The fluorescence imaging technique and/or nuclear imaging technique can be employed for monitoring and/or visualizing the distribution of the detectably labeled compound within the sample or a specific body part or body area.

The presence or absence of the compound/protein aggregate complex is then optionally correlated with the presence or absence of alpha-synuclein aggregates including, but not limited to, Lewy bodies and/or Lewy neurites in the sample or specific body part or area. Finally, the amount of the compound/protein aggregate complex can be compared to a normal control value which has been determined in a sample or a specific body part or body area of a healthy subject, wherein an increase in the amount of the compound/protein aggregate complex compared to a normal control value may indicate that the patient is suffering from or is at risk of developing a disorder or abnormality associated with alpha-synuclein aggregates including, but not limited to, Lewy bodies and/or Lewy neurites.

The present invention also relates to a method of determining the amount of alpha-synuclein aggregates including, but not limited to, Lewy bodies and/or Lewy neurites in a tissue and/or a body fluid. This method comprises the steps of:

(a) providing a sample representative of the tissue and/or body fluid under investigation;
(b) testing the sample for the presence of alpha-synuclein aggregates including, but not limited to, Lewy bodies and/or Lewy neurites with a compound of the present invention;
(c) determining the amount of compound bound to the alpha-synuclein aggregates including, but not limited to, Lewy bodies and/or Lewy neurites; and
(d) calculating the amount of alpha-synuclein aggregates including, but not limited to, Lewy bodies and/or Lewy neurites in the tissue and/or body fluid.

The sample can be tested for the presence of alpha-synuclein aggregates including, but not limited to, Lewy bodies and/or Lewy neurites with a compound of the present invention by bringing the sample into contact with a compound of the invention, allowing the compound of the invention to bind to the alpha-synuclein aggregates including, but not limited to, Lewy bodies and/or Lewy neurites to form a compound/protein aggregate complex and detecting the formation of the compound/protein aggregate complex as explained above.

Monitoring minimal residual disorder in a patient suffering from a disorder or abnormality associated with alpha-synuclein aggregates including, but not limited to, Lewy bodies and/or Lewy neurites who has been treated with a medicament with a compound according to the invention may be achieved by (a) bringing a sample or a specific body part or body area suspected to contain an alpha-synuclein aggregates including, but not limited to, Lewy bodies and/or Lewy neurites into contact with a compound of the present invention;
(b) allowing the compound to bind to the alpha-synuclein aggregates including, but not limited to, Lewy bodies and/or Lewy neurites to form a compound/protein aggregate complex;
(c) detecting the formation of the compound/protein aggregate complex;
(d) optionally correlating the presence or absence of the compound/protein aggregate complex with the presence or absence of alpha-synuclein aggregates including, but not limited to, Lewy bodies and/or Lewy neurites in the sample or specific body part or body area; and
(e) optionally comparing the amount of the compound/protein aggregate complex to a normal control value, wherein an increase in the amount of the aggregate compared to a normal control value may indicate that the patient may still suffer from a minimal residual disease.

How steps (a) to (e) can be conducted has already been explained above.

In the method for monitoring minimal residual disorder, the method can further comprises steps (i) to (vi) before step (a):

(i) bringing a sample or specific body part or body area suspected to contain alpha-synuclein aggregates including, but not limited to, Lewy bodies and/or Lewy neurites into contact with the compound as defined in any one of claims 1 to 8, which compound specifically binds to the alpha-synuclein aggregates including, but not limited to, Lewy bodies and/or Lewy neurites;
(ii) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;
(iii) detecting the formation of the compound/(alpha-synuclein aggregates including, but not limited to, Lewy bodies and/or Lewy neurites) complex;
(iv) correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area;
(v) optionally comparing the amount of the compound/(alpha-synuclein aggregates including, but not limited to, Lewy bodies and/or Lewy neurites) complex to a normal control value; and
(vi) treating the patient with the medicament.

Optionally the method can further comprise step (A) after step (d) or step (e):

(A) comparing the amount of the compound/(alpha-synuclein aggregates including, but not limited to, Lewy bodies and/or Lewy neurites) complex determined in step (iv) to the amount of the compound/(alpha-synuclein aggregates including, but not limited to, Lewy bodies and/or Lewy neurites) complex determined in step (d).

In order to monitor minimal residual disorder over time, steps (a) to (c) and optionally steps (d) and (e) of the method of monitoring minimal residual disorder can be repeated one or more times.

In the method for monitoring minimal residual disorder the amount of the compound/protein aggregate complex can be optionally compared at various points of time during the treatment, for instance, before and after onset of the treatment or at various points of time after the onset of the treatment. A change, especially a decrease, in the amount of the compound/protein aggregate complex may indicate that the residual disorder is decreasing.

Predicting responsiveness of a patient suffering from a disorder or abnormality associated with alpha-synuclein aggregates including, but not limited to, Lewy bodies and/or Lewy neurites and being treated with a medicament can be achieved by (a) bringing a sample or a specific body part or body area suspected to contain an alpha-synuclein aggregates including, but not limited to, Lewy bodies and/or Lewy neurites into contact with a compound of the present invention;

(b) allowing the compound to bind to the alpha-synuclein aggregates including, but not limited to, Lewy bodies and/or Lewy neurites to form a compound/protein aggregate complex;

(c) detecting the formation of the compound/protein aggregate complex;

(d) optionally correlating the presence or absence of the compound/protein aggregate complex with the presence or absence of alpha-synuclein aggregates including, but not limited to, Lewy bodies and/or Lewy neurites in the sample or specific body part or body area; and (e) optionally comparing the amount of the compound/protein aggregate complex to a normal control value.

How steps (a) to (e) can be conducted has already been explained above.

In the method for predicting the responsiveness, the method can further comprises steps (i) to (vi) before step (a):

(i) bringing a sample or specific body part or body area suspected to contain alpha-synuclein aggregates including, but not limited to, Lewy bodies and/or Lewy neurites into contact with the compound as defined in any one of claims 1 to 8, which compound specifically binds to the alpha-synuclein aggregates including, but not limited to, Lewy bodies and/or Lewy neurites;

(ii) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;

(iii) detecting the formation of the compound/(alpha-synuclein aggregates including, but not limited to, Lewy bodies and/or Lewy neurites) complex;

(iv) correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area;

(v) optionally comparing the amount of the compound/(alpha-synuclein aggregates including, but not limited to, Lewy bodies and/or Lewy neurites) complex to a normal control value; and (vi) treating the patient with the medicament.

Optionally the method can further comprise step (A) after step (d) or step (e):

(A) comparing the amount of the compound/(alpha-synuclein aggregates including, but not limited to, Lewy bodies and/or Lewy neurites) complex determined in step (iv) to the amount of the compound/(alpha-synuclein aggregates including, but not limited to, Lewy bodies and/or Lewy neurites) complex determined in step (d).

In order to determine the responsiveness over time, steps (a) to (c) and optionally steps (d) and (e) of the method of predicting responsiveness can be repeated one or more times.

In the method for predicting responsiveness the amount of the compound/protein aggregate complex can be optionally compared at various points of time during the treatment, for instance, before and after onset of the treatment or at various points of time after the onset of the treatment. A change, especially a decrease, in the amount of the compound/protein aggregate complex may indicate that the patient has a high potential of being responsive to the respective treatment.

Optionally, the diagnostic composition can be used before, during and after, surgical procedures (e.g. deep brain stimulation (DBS)) and non-invasive brain stimulation (such as repetitive transcranial magnetic stimulation (rTMS)), for visualizing alpha-synuclein aggregates before, during and after such procedures. Surgical techniques, including DBS, improve advanced symptoms of PD on top of the best currently used medical therapy. During the past 2 decades, rTMS has been closely examined as a possible treatment for PD (Ying-hui Chou et al. JAMA Neurol. 2015 Apr. 1; 72(4): 432-440).

In a further embodiment of the invention, the diagnostic composition can be used in a method of collecting data for monitoring residual disorder in a patient suffering from a disorder or abnormality associated with alpha-synuclein aggregates including, but not limited to, Lewy bodies and/or Lewy neurites who has been treated with a surgical procedure or non-invasive brain stimulation procedure, wherein the method comprises:

(a) bringing a sample or specific body part or body area suspected to contain alpha-synuclein aggregates including, but not limited to, Lewy bodies and/or Lewy neurites into contact with a compound of the present invention, which compound specifically binds to the alpha-synuclein aggregates including, but not limited to, Lewy bodies and/or Lewy neurites;

(b) allowing the compound to bind to the alpha-synuclein aggregates including, but not limited to, Lewy bodies and/or Lewy neurites to form a compound/(alpha-synuclein aggregates including, but not limited to, Lewy bodies and/or Lewy neurites) complex;

(c) detecting the formation of the compound/(alpha-synuclein aggregates including, but not limited to, Lewy bodies and/or Lewy neurites) complex;

(d) optionally correlating the presence or absence of the compound/(alpha-synuclein aggregates including, but not limited to, Lewy bodies and/or Lewy neurites) complex with the presence or absence of alpha-synuclein aggregates including, but not limited to, Lewy bodies and/or Lewy neurites in the sample or specific body part or body area; and (e) optionally comparing the amount of the compound/(alpha-synuclein aggregates including, but not limited to, Lewy bodies and/or Lewy neurites) complex to a normal control value.

A compound according to the present invention can also be incorporated into a test kit for detecting alpha-synuclein protein aggregates including, but not limited to, Lewy bodies and/or Lewy neurites. The test kit typically comprises a container holding one or more compounds according to the present invention and instructions for using the compound for the purpose of binding to an alpha-synuclein aggregates including, but not limited to, Lewy bodies and/or Lewy neurites to form a compound/protein aggregate complex and detecting the formation of the compound/protein aggregate complex such that presence or absence of the compound/protein aggregate complex correlates with the presence or absence of the alpha-synuclein aggregates including, but not limited to, Lewy bodies and/or Lewy neurites.

The term "test kit" refers in general to any diagnostic kit known in the art. More specifically, the latter term refers to a diagnostic kit as described in Zrein et al., Clin. Diagn. Lab. Immunol., 1998, 5, 45-49.

Radiopharmaceutical Preparations

The compounds of the present invention can also be employed in kits for the preparation of radiopharmaceutical preparations. Due to the radioactive decay, the radiopharmaceuticals are usually prepared immediately before use. The kit comprises a precursor of the compound of the present invention and an agent which reacts with the precursor to introduce a radioactive label to the compound of the present invention. The precursor of the compound of the present invention can, for example, be a compound having the formula (IIIa), (IIIb), (IVa) or (IVb). The agent can be an agent which introduces a radioactive label such as $^{18}F$.

Pharmaceutical Compositions

The compounds of the present invention can be employed in treating, preventing or alleviating a disorder or abnormality associated with alpha-synuclein aggregates.

Due to their design and to the binding characteristics, the compounds of the present invention are suitable for treating, preventing or alleviating a disorder or abnormality associated with alpha-synuclein aggregates including, but not limited to, Lewy bodies and/or Lewy neurites. Diseases involving alpha-synuclein aggregates are generally listed as synucleinopathies (or α-synucleinopathies). The compounds of the present invention are suitable for treating, preventing or alleviating disorders including, but not limited to, Parkinson's disease (sporadic, familial with alpha-synuclein mutations, familial with mutations other than alpha-synuclein, pure autonomic failure and Lewy body dysphagia), dementia with Lewy bodies ("pure" Lewy body dementia), sporadic Alzheimer's disease, familial Alzheimer's disease with APP mutations, familial Alzheimer's disease with PS-1, PS-2 or other mutations, familial British dementia, Lewy body variant of Alzheimer's disease and normal aging (Down syndrome). Synucleinopathies with neuronal and glial aggregates of alpha synuclein include multiple system atrophy (Shy-Drager syndrome, striatonigral degeneration and olivopontocerebellar atrophy). Other diseases that may have alpha-synuclein-immunoreactive lesions include traumatic brain injury, chronic traumatic encephalopathy, tauopathies (Pick's disease, frontotemporal dementia, progressive supranuclear palsy, corticobasal degeneration and Niemann-Pick type C1 disease), motor neuron disease, amyotrophic lateral sclerosis (sporadic, familial and ALS-dementia complex of Guam), neuroaxonal dystrophy, neurodegeneration with brain iron accumulation type 1 (Hallervorden-Spatz syndrome), prion diseases, ataxia telangiectatica, Meige's syndrome, subacute sclerosing panencephalitis, Gaucher disease as well as other lysosomal storage disorders (including Kufor-Rakeb syndrome and Sanfilippo syndrome) and rapid eye movement (REM) sleep behavior disorder. (Jellinger, Mov Disord 2003, 18 Suppl. 6, S2-12; Galvin et al. JAMA Neurology 2001, 58 (2), 186-190; Kovari et al., Acta Neuropathol. 2007, 114(3), 295-8; Saito et al., J Neuropathol Exp Neurol. 2004, 63(4), 323-328; McKee et al., Brain, 2013, 136(Pt 1), 43-64; Puschmann et al., Parkinsonism Relat Disord 2012, 18S1, S24-S27; Usenovic et al., J Neurosci. 2012, 32(12), 4240-4246; Winder-Rhodes et al., Mov Disord. 2012, 27(2), 312-315; Ferman et al., J Int Neuropsychol Soc. 2002, 8(7), 907-914). Preferably, the compounds of the present invention are suitable for treating, preventing or alleviating Parkinson's disease (PD).

In pharmaceutical applications, the compound of the present invention is preferably administered in a pharmaceutical composition comprising the compound of the invention. A "pharmaceutical composition" is defined in the present invention as a composition comprising one or more compounds of the present invention in a form suitable for administration to a patient, e.g., a mammal such as a human, and which is suitable for treating, alleviating or preventing the specific disorder or abnormality at issue. Preferably a pharmaceutical composition further comprises a physiologically acceptable carrier, diluent, adjuvant or excipient. The dose of the compound of the present invention will vary depending on the exact compound to be administered, the weight of the patient, and other variables as would be apparent to a physician skilled in the art.

While it is possible for the compounds of the present invention to be administered alone, it is preferable to formulate them into a pharmaceutical composition in accordance with standard pharmaceutical practice. Thus, the invention also provides a pharmaceutical composition which comprises a therapeutically effective amount of a compound of formulae (I) or (II) in admixture with a pharmaceutically acceptable carrier, diluent, adjuvant or excipient.

Pharmaceutically acceptable excipients are well known in the pharmaceutical art, and are described, for example, in Remington's Pharmaceutical Sciences, 15$^{th}$ Ed., Mack Publishing Co., New Jersey (1975). The pharmaceutical excipient can be selected with regard to the intended route of administration and standard pharmaceutical practice. The excipient must be acceptable in the sense of being not deleterious to the recipient thereof.

Pharmaceutically useful excipients that may be used in the formulation of the pharmaceutical composition of the present invention may comprise, for example, carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium stearate, talc, monosaccharides, disaccharides, starch, gelatin, cellulose, methylcellulose, sodium carboxymethyl cellulose, dextrose, hydroxypropyl-β-cyclodextrin, polyvinylpyrrolidone, low melting waxes, and ion exchange resins.

The routes for administration (delivery) of the compounds of the invention include, but are not limited to, one or more of: oral (e.g. as a tablet, capsule, or as an ingestible solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

For example, the compounds can be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

If the compounds of the present invention are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds; and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

As indicated, the compounds of the present invention can be administered intranasally or by inhalation and are conveniently delivered in the form of a dry powder inhaler or an aerosol spray presentation from a pressurized container, pump, spray or nebulizer with the use of a suitable propellant, e.g. dichlorodifluoromethane, trichlorofluoromethane, dichlorotetrafluoroethane, a hydrofluoroalkane such as 1,1,1,2-tetrafluoroethane (HFA134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the compound and a suitable powder base such as lactose or starch.

Alternatively, the compounds of the present invention can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

They may also be administered by the pulmonary or rectal routes. They may also be administered by the ocular route. For ophthalmic use, the compounds can be formulated as micronized suspensions in isotonic, pH was adjusted, sterile saline, or, preferably, as solutions in isotonic, pH was adjusted, sterile saline, optionally in combination with a preservative such as a benzylalkonium chloride. Alternatively, they may be formulated in an ointment such as petrolatum.

For application topically to the skin, the compounds of the present invention can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. A proposed dose of the compounds according to the present invention for administration to a human (of approximately 70 kg body weight) is 0.1 mg to 1 g, preferably 1 mg to 500 mg of the active ingredient per unit dose. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The precise dose and route of administration will ultimately be at the discretion of the attendant physician or veterinarian.

The compounds of the invention may also be used in combination with one or more therapeutic agents. When a compound of the invention is used in combination with a second therapeutic agent active against the same disease, the dose of each compound may differ from that when the compound is used alone.

The combinations referred to above may conveniently be presented for use in the form of a pharmaceutical formulation. The individual components of such combinations may be administered either sequentially or simultaneously in separate or combined pharmaceutical formulations by any convenient route. When administration is sequential, either the compound of the invention or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately they may be provided in any convenient formulation, conveniently in such manner as are known for such compounds in the art.

The pharmaceutical compositions of the invention can be produced in a manner known per se to the skilled person as described, for example, in Remington's Pharmaceutical Sciences, 15th Ed., Mack Publishing Co., New Jersey (1975).

The compounds according to the present invention can also be provided in the form of a mixture with at least one compound selected from a therapeutic agent different from the compound of the present invention, a pharmaceutically acceptable carrier, a diluent and an excipient. The compound and/or the therapeutic agent different from the compound of the present invention are preferably present in a therapeutically effective amount.

The nature of the therapeutic agent different from the compound of the present invention will depend on the intended use of the mixture. The therapeutic agent different from the compound of the present invention may exert its biological effect by the same or a similar mechanism as the compound according to the invention or by an unrelated mechanism of action or by a multiplicity of related and/or unrelated mechanisms of action.

Generally, the therapeutic agent different from the compound of the present invention may include neutron-transmission enhancers, psychotherapeutic drugs, acetylcholineesterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists. In particular, the therapeutic agent different from the compound of the present invention can be selected from the group consisting of a compound used in the treatment of amyloidosis, compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), α-secretase activators, β- and γ-secretase inhibitors, tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists, other drugs including any amyloid or tau modifying drug and nutritive supplements, an antibody, including any functionally equivalent antibody or functional parts thereof.

In a further embodiment, the mixtures according to the invention may comprise niacin or memantine together with a compound according to the present invention and, optionally, a pharmaceutically acceptable carrier and/or a diluent and/or an excipient.

In still another embodiment of the invention mixtures are provided that comprise as a therapeutic agent different from the compound of the present invention "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with a compound according to the invention and, optionally, a pharmaceutically acceptable carrier and/or a diluent and/or an excipient.

Preferred compounds are illustrated in the examples.

The compounds of the present invention can be synthesized by one of the general methods shown in the following schemes. These methods are only given for illustrative purposes and should not to be construed as limiting.

General Synthetic Schemes for the Preparation of Building Blocks of this Invention Scheme 1

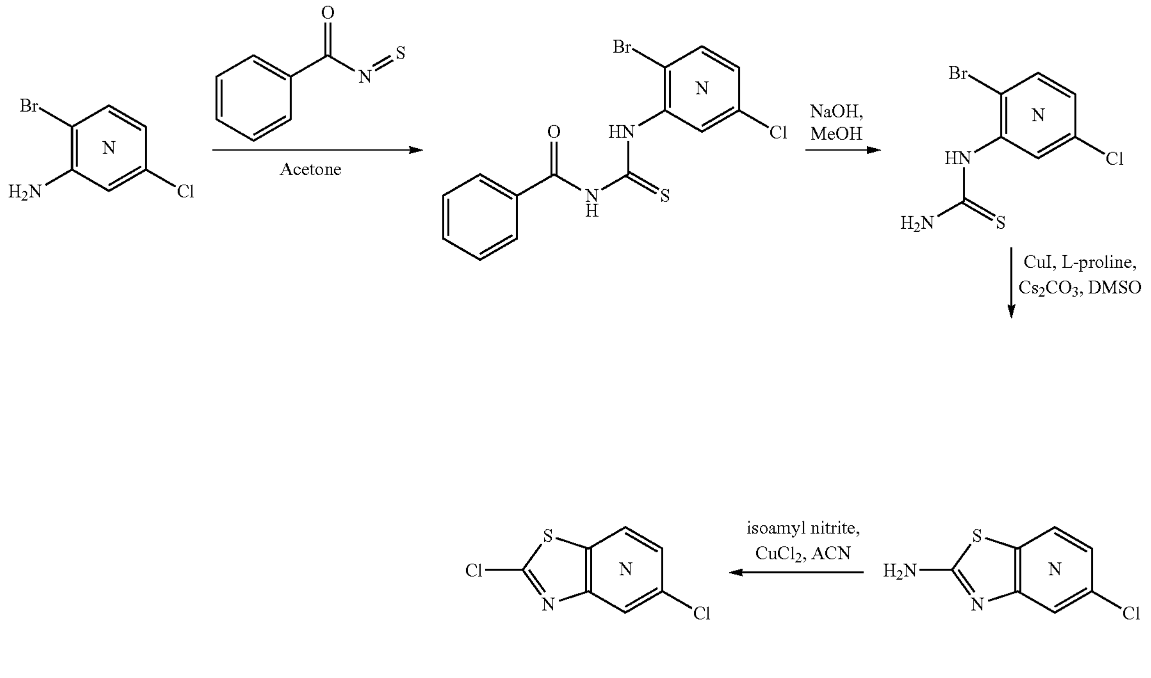

-continued

Scheme 1a

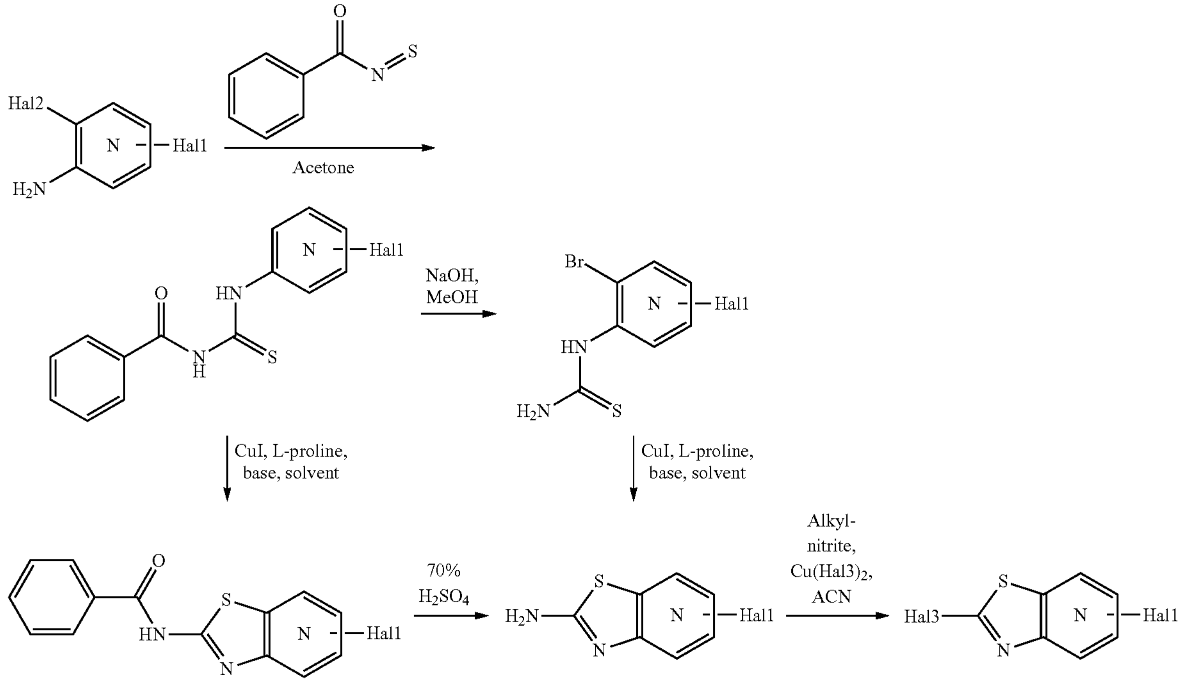

Commercially available halogenated aminopyridines are reacted with benzoyl isothiocyanate in a solvent such as acetone to afford the desired benzoyl thiourea pyridine derivatives after purification. Deprotection of benzoyl groups was achieved using basic conditions. Then, the thioureas were cyclized using a copper catalyst. An alternative route could be employed by cyclizing first the benzoyl thiourea pyridine derivatives followed by deprotection of the amide using acidic conditions. Finally, the amino groups were transformed into halogen using standard conditions.

Scheme 2

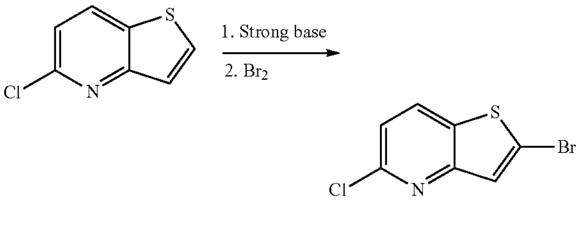

5-Chlorothieno[3,2-b]pyridine was treated with a strong base in a suitable solvent followed by addition of bromine to deliver the desired building block after purification.

Scheme 3

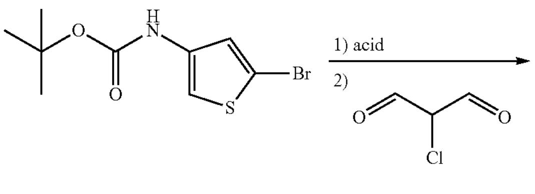

-continued

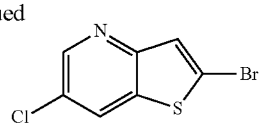

Tert-butyl (5-bromothiophen-3-yl)carbamate was treated under acidic conditions and the resulting product was cyclized using 2-halomalonaldehyde in a solvent to afford the desired building blocks after purification.

General Synthetic Scheme for the Preparation of Compounds of this Invention

Scheme 4

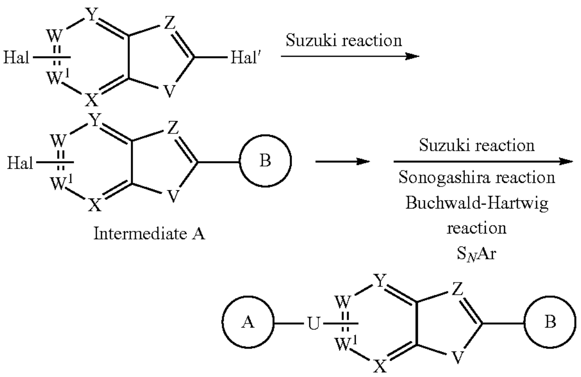

Bicyclic building blocks (Hal, Hal'=Br, Cl) were treated with boronic acids or esters in a solvent via palladium-catalyzed cross-coupling (Suzuki reaction) conditions to afford the desired intermediate A after purification. The intermediate A can be further functionalized using palladium-catalyzed cross-coupling conditions such as Suzuki reaction, Buchwald-Hartwig reaction or Sonogashira reaction to afford the desired compounds after purification. In the case of the Suzuki reactions, the final compounds could be also obtained via a one pot procedure by sequential additions of boronic acids or ester. Finally, the intermediate A or even a final compound bearing a leaving group such as a fluorine atom could be subjected to $S_NAr$ conditions to afford the desired final compounds after purification.

Scheme 5

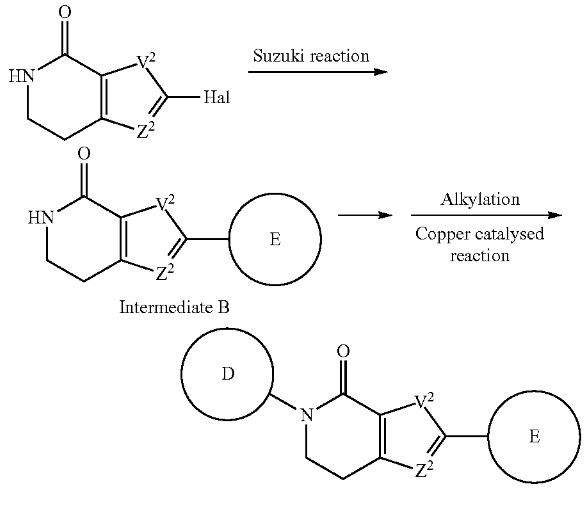

Bicyclic building blocks (Hal=Br, Cl) were treated with a boronic acid or ester in a solvent via palladium-catalyzed cross-coupling (Suzuki reaction) conditions to afford the desired intermediate B after purification. The intermediate B was subjected either to alkylation using a base and an electrophile or copper-catalyzed cross-coupling reaction with a haloaryl to afford the desired final compounds after purification.

General Synthesis of $^{18}F$-Labeled Compounds of the Present Invention

Compounds having the formula (I) or (II) which are labeled by $^{18}F$ can be prepared by reacting a precursor compound, as described below, with an $^{18}F$-fluorinating agent, so that the LG comprised in the precursor compound is replaced by $^{18}F$.

Any suitable $^{18}F$-fluorinating agent can be employed. Typical examples include $H^{18}F$, alkali or alkaline earth $^{18}F$-fluorides (e.g., $K^{18}F$, $Rb^{18}F$, $Cs^{18}F$, and $Na^{18}F$). Optionally, the $^{18}F$-fluorination agent can be used in combination with a chelating agent such as a cryptand (e.g.: 4,7,13,16,21,24-hexaoxa-1,10-diazabicyclo[8.8.8]-hexacosane—Kryptofix®) or a crown ether (e.g.: 18-crown-6). Alternatively, the $^{18}F$-fluorinating agent can be a tetraalkylammonium salt of $^{18}F$ or a tetraalkylphosphonium salt of $^{18}F$; e.g., tetra($C_{1-6}$ alkyl)ammonium salt of $^{18}F$ or a tetra($C_{1-6}$ alkyl)phosphonium salt of $^{18}F$. Preferably, the $^{18}F$-fluorination agent is $K^{18}F$, $H^{18}F$, $Cs^{18}F$, $Na^{18}F$ or tetrabutylammonium [$^{18}F$]fluoride.

General Synthetic Scheme for the Preparation of Precursor Compounds

Scheme 6

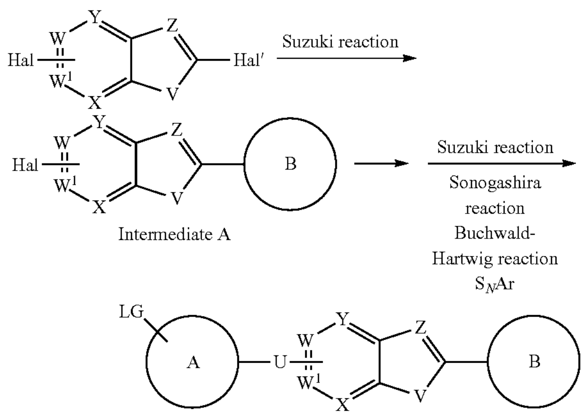

Bicyclic building blocks (Hal, Hal'=Br, Cl) were treated with boronic acids or esters in a solvent via palladium-catalyzed cross-coupling conditions (Suzuki reaction) to afford the desired intermediate A after purification. The intermediate A can be further functionalized using palladium-catalyzed cross-coupling conditions such as Suzuki reaction, Buchwald-Hartwig reaction or Sonogashira reaction to afford the desired precursor compounds containing a leaving group (LG) after purification. In the case of the Suzuki reactions, the final compounds could be also obtained via a one pot procedure by sequential additions of boronic acids or esters. Finally, the intermediate A or even a final compound bearing a leaving group (different from the LG group of the final precursor compounds) such as a fluorine atom could, be subjected to $S_NAr$ conditions to afford the desired precursor compounds containing a further LG after purification. The derivatives containing a LG are precursor compounds to allow the introduction of the $^{18}F$-label in the following step. Preferred LG for the introduction of $^{18}F$ are: $C_{1-4}$ alkyl sulfonate $C_{6-10}$ aryl sulfonate, nitro, trimethylammonium and halogens. In place of a LG can be also employed a boronic ester. Rings B, D, and E carrying a LG can be prepared following a procedure similar to the one given for Ring A above.

General Synthetic Scheme for the Preparation of $^{18}F$-Labeled Compounds

Scheme 7

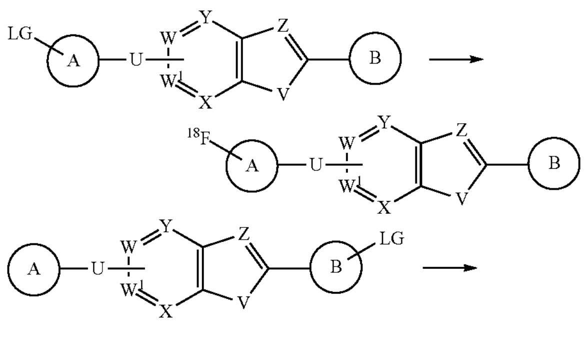

-continued

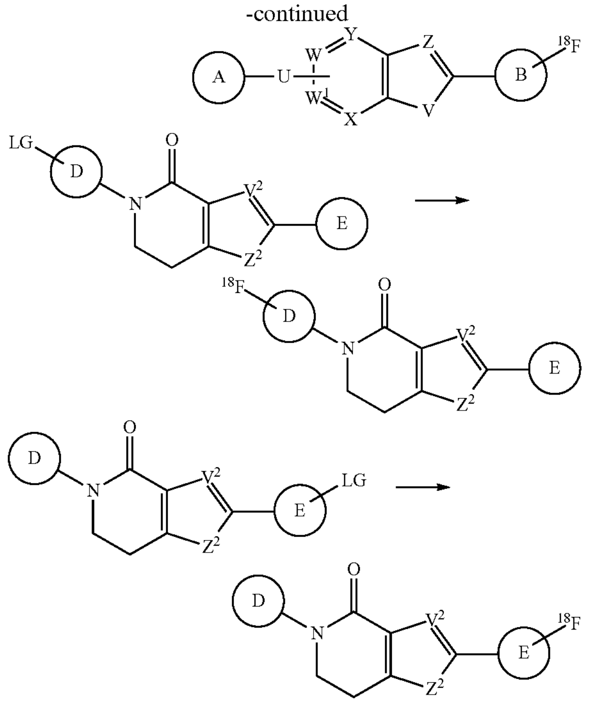

The reactions take place in the presence of a fluorinating agent and typically a solvent.

$^{18}F$ labeled compounds can be prepared by reacting the precursor compounds containing a LG with an $^{18}F$-fluorinating agent, so that the LG is replaced by $^{18}F$. The reagents, solvents and conditions which can be used for the $^{18}F$-fluorination are well-known to a skilled person in the field (L. Cai, S. Lu, V. Pike, Eur. J. Org. Chem 2008, 2853-2873; J. Fluorine Chem., 27 (1985):177-191; Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50). Preferably, the solvents used in the $^{18}F$-fluorination are DMF, DMSO, acetonitrile, DMA, or mixtures thereof, preferably the solvent is acetonitrile, DMSO.

Although the reaction is shown above with respect to $^{18}F$ as a radioactive label, other radioactive labels can be introduced following similar procedures.

The invention is illustrated by the following examples which, however, should not be construed as limiting.

EXAMPLES

All reagents and solvents were obtained from commercial sources and used without further purification. Proton ($^1H$) spectra were recorded on a Bruker DRX-400 MHz NMR spectrometer or on a Bruker AV-400 MHz NMR spectrometer in deuterated solvents. Mass spectra (MS) were recorded on an Advion CMS mass spectrometer. Chromatography was performed using silica gel (Fluka: Silica gel 60, 0.063-0.2 mm) and suitable solvents as indicated in the specific examples. Flash purification was conducted with a Biotage Isolera One flash purification system using HP-Sil or KP-NH SNAP cartridges (Biotage) and the solvent gradient indicated in the specific examples. Thin layer chromatography (TLC) was carried out on silica gel plates with UV detection. Although some of the present examples do not indicate that the respective compounds were detectably labeled, it is understood that corresponding detectably labeled compounds are intended and can be easily prepared, e.g., by using detectably labeled starting materials, such as starting materials containing $C(^3H)_3$, $(^{11}C)H_3$ or $^{18}F$.

Preparative Example 1

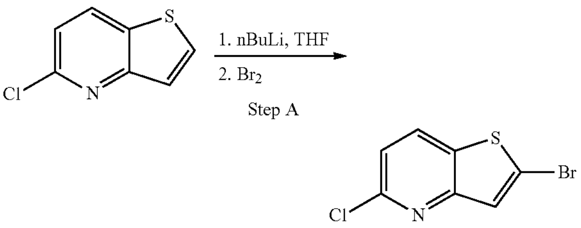

Step A:

A solution of commercially available 5-chlorothieno[3,2-b]pyridine (0.600 g, 3.537 mmol) in tetrahydrofuran (15 mL) was cooled to −78° C. Then a 2.5 M solution of n-butyl-lithium in hexane (3.3 mL, 5.305 mmol) was added at −78° C. The temperature was allowed to raise to −40° C. and the mixture was stirred for 30 minutes. The mixture was cooled to −78° C. and bromine (0.362 mL, 7.07 mmol) was added dropwise. The mixture was stirred at −78° C. for 1 hour and the reaction mixture was quenched with 50 mL of water. The aqueous mixture was extracted with ethyl acetate (3×50 mL), the combined organic layers were dried over $Na_2SO_4$ and concentrated. The residue was purified by chromatography on HP-Sil SNAP cartridges using a Biotage Isolera One purification system employing an ethyl acetate/n-heptane gradient (0/100→10/90) to afford the title compound (0.774 g, 88%).

$^1H$-NMR (400 MHz, DMSO-$d_6$) δ 8.52 (d, 1H), 7.80 (s, 1H), 7.50 (d, 1H).

MS (ESI); m/z=249.91 $[M+H]^+$

Preparative Example 2

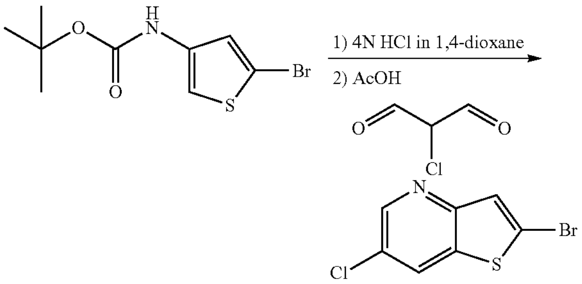

To a solution of tert-butyl (5-bromothiophen-3-yl)carbamate (1 g, 3.59 mmol) in methanol (5 mL) was added at room temperature 4N HCl (2 mL, 65.8 mmol). After 4 hours at room temperature, the reaction mixture was concentrated under reduced pressure to dryness. Then, glacial acetic acid (10 mL) was added followed by 2-chloromalonaldehyde (0.421 g, 3.95 mmol) and the reaction mixture was refluxed for 2 hours. The reaction mixture was concentrated under reduced pressure and 1N NaOH (100 mL) was added. The aqueous phase was extracted several times with dichloromethane (DCM). The combined organics were dried over $Na_2SO_4$, filtered and dried under reduced pressure. The residue was purified on HP-Sil SNAP cartridges using a Biotage Isolera One purification system employing ethyl acetate/n-heptane eluent (10/90) to afford the title compound (320 mg, 36%).

$^1$H-NMR (400 MHz, DMSO-$d_6$) δ 8.65 (s, 2H), 7.82 (s, 1H)

MS (ESI); m/z=249.94 $[M+H]^+$

Preparative Example 3

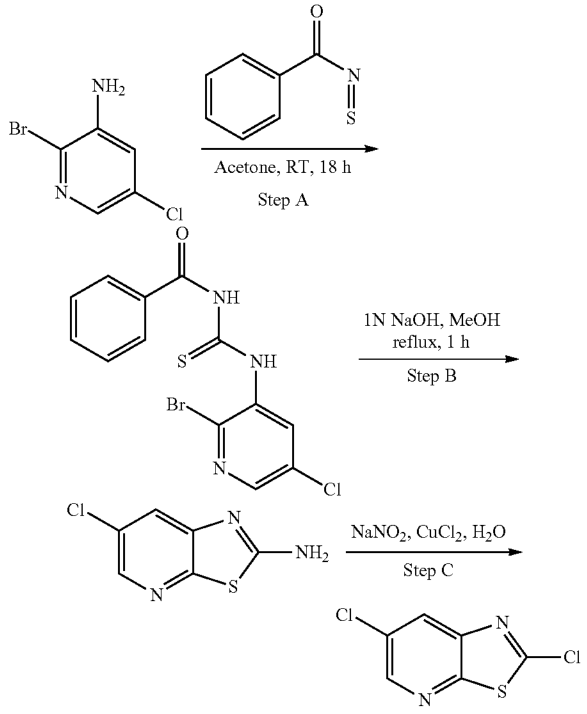

mmol) in acetone (20 mL) was stirred at room temperature for 18 hours. The solid was filtered, washed with n-heptane and dried to give the desired product (15.9 g, 89%).

$^1$H-NMR (400 MHz, DMSO-$d_6$) δ 12.67 (s, 1H), 12.04 (s, 1H), 8.60-8.49 (m, 1H), 8.45 (d, 1H), 8.01 (d, 2H), 7.69 (t, 1H), 7.56 (t, 2H)

MS (ESI); m/z=NA

Step B:

A suspension of N-((2-bromo-5-chloropyridin-3-yl)carbamothioyl)benzamide (15.89 g, 42.9 mmol) in 6N NaOH (214 ml) and methanol (150 mL) was refluxed for 1 hour. Then, the reaction mixture was cooled to 00° C. After stirring at 00° C. for 30 min, the solid was filtered, washed with water and dried to give the desired product (4.4 g, 55%).

$^1$H-NMR (400 MHz, DMSO-$d_6$) δ 8.24-7.89 (m, 3H), 7.72 (s, 1H)

Step C:

To a solution of 3M $H_2SO_4$ (20 mL) at 0° C. was added 6-chlorothiazolo[5,4-b]pyridin-2-amine (200 mg, 1.077 mmol). Then, sodium nitrite (104 mg, 1.508 mmol) in water (2 mL) was added very slowly. After 1 hour at 0° C., copper(II) chloride (203 mg, 1.508 mmol) was added, followed by the addition of 2 mL of concentrated HCl. Then, the reaction mixture was allowed to warm to room temperature and stirred for 4 hours. Water was added and the aqueous phase was extracted several times with ethyl acetate. The combined organics were washed with saturated aqueous solution of $NH_4Cl$, dried over $Na_2SO_4$, filtered and dried under reduced pressure. The aqueous phase was extracted several times with DCM. The combined organics were dried over $Na_2SO_4$, filtered and dried under reduced pressure. The residue was purified on HP-Sil SNAP cartridges using a Biotage Isolera One purification system employing methanol/dichloromethane eluent (2/98) to afford the title compound (128 mg, 58%).

$^1$H-NMR (400 MHz, DMSO-$d_6$) δ 8.75 (d, 1H), 8.67 (d, 1H)

Preparative Example 4

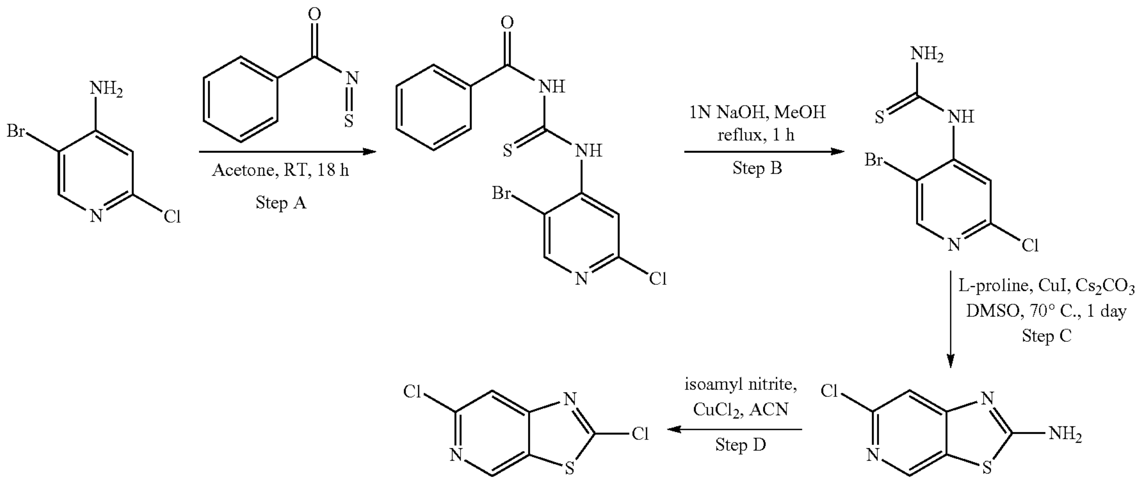

Step A:

A solution of 2-bromo-5-chloropyridin-3-amine (10 g, 48.2 mmol) and benzoyl isothiocyanate (8.87 ml, 67.5

Step A:

A solution of 5-bromo-2-chloropyridin-4-amine (5 g, 24.10 mmol) and benzoyl isothiocyanate (9.51 ml, 72.3 mmol) in acetone (25 mL) was stirred at room temperature for 18 hours. The solid was concentrated to ~10 mL, filtered, washed with n-heptane and dried to give the desired product (6 g, 68%).

$^1$H-NMR (400 MHz, DMSO-$d_6$) δ 13.21 (s, 1H), 12.14 (s, 1H), 8.76 (s, 1H), 8.71 (s, 1H), 7.99 (d, 2H), 7.69 (t, 1H), 7.56 (t, 2H)

MS (ESI); m/z=NA

Step B:

A suspension of N-((2-bromo-5-chloropyridin-3-yl)carbamothioyl)benzamide (15.89 g, 42.9 mmol) in 6N NaOH (15 mL) and methanol (50 mL) was refluxed for 4 hours. The reaction mixture was cooled to room temperature and saturated aqueous solution of $NH_4Cl$ was added until a precipitate was formed. After 1 hour at room temperature, the solid was filtered, washed with water (2×30 mL), dried, washed with DCM and further dried to give the desired product (2.7 g, 92%).

Step C:

A suspension of 1-(5-bromo-2-chloropyridin-4-yl)thiourea (1.39 g, 5.21 mmol), L-proline (0.120 g, 1.043 mmol), copper(I) iodide (0.099 g, 0.521 mmol) and $Cs_2CO_3$ (3.40 g, 10.43 mmol) in DMSO (3 mL) was heated at 70° C. for 1 day. The reaction mixture was poured into water (50 mL). The solid was filtered, washed with more water and dried to give the desired product (435 mg, 45%).

$^1$H-NMR (400 MHz, DMSO-$d_6$) δ 8.56 (s, 1H), 8.32 (s, 2H), 7.31 (s, 1H).

MS (ESI); m/z=185.98 $[M+H]^+$

Step D:

To a suspension of 6-chlorothiazolo[5,4-c]pyridin-2-amine (500 mg, 2.69 mmol) and copper(II) chloride (471 mg, 3.50 mmol) in acetonitrile (50 mL) at 00° C. was added isoamyl nitrite (0.544 ml, 4.04 mmol). Then, the reaction mixture was stirred at room temperature for 2 hours. Then, copper(II) chloride (471 mg, 3.50 mmol) and isoamyl nitrite (0.544 ml, 4.04 mmol) were added again and heated at 65° C. for 18 hours. The reaction mixture was cooled to room temperature and the reaction mixture was filtered. Water (50 mL) was added and the aqueous phase was extracted several time with dichloromethane. The combined organics were dried over $Na_2SO_4$, filtered and dried under reduced pressure. The residue was purified on HP-Sil SNAP cartridges using a Biotage Isolera One purification system employing methanol/dichloromethane eluent (2/98) to afford the title compound (430 mg, 78%).

1H NMR (400 MHz, DMSO-d6) δ 9.18 (s, 1H), 8.17 (s, 1H).

Preparative Example 4a

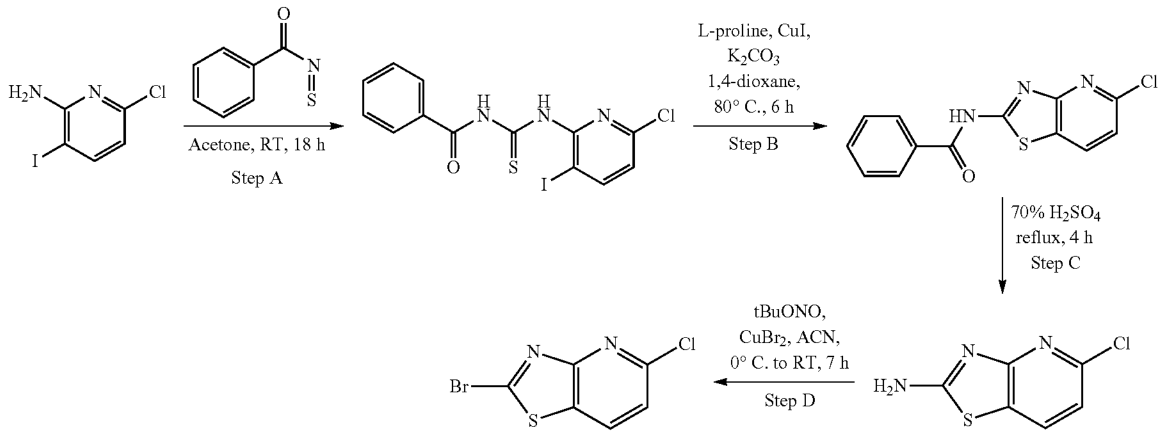

Step A:

A solution of 6-chloro-3-iodopyridin-2-amine (13.87 g, 54.5 mmol) and benzoyl isothiocyanate (9.32 ml, 70.9 mmol) in acetone (150 mL) was stirred at room temperature for 18 hours. The solid was filtered, washed with n-heptane and dried to give the desired product (22.8 g, 91%).

$^1$H-NMR (400 MHz, DMSO-$d_6$) δ 12.39 (s, 1H), 11.88 (s, 1H), 8.38 (d, 1H), 8.12-7.90 (m, 2H), 7.68 (t, 1H), 7.56 (t, 2H), 7.31 (d, 1H).

MS (ESI); m/z=417.82 $[M+H]^+$

Step B:

To a solution of N-((6-chloro-3-iodopyridin-2-yl)carbamothioyl)benzamide (20.76 g, 49.7 mmol) in 1,4-dioxane (250 mL) was added potassium carbonate (13.74 g, 99 mmol), L-proline (1.145 g, 9.94 mmol) and copper(I) iodide (0.947 g, 4.97 mmol). Then, the reaction mixture was stirred at 80° C. for 6 hours. The reaction mixture was poured into 500 mL of water and 500 mL of aqueous saturated solution of $NH_4Cl$. The suspension was stirred at room temperature for 1 hour. The solid was filtered, washed with aqueous saturated solution of $NH_4Cl$ (2×250 mL), water (3×250 mL) and dried to give the desired product (14.8 g, 100%).

$^1$H-NMR (400 MHz, DMSO-$d_6$) δ 13.32 (s, 1H), 8.55 (d, 1H), 8.17 (d, 2H), 7.70 (t, 1H), 7.59 (t, 2H), 7.45 (d, 1H).

MS (ESI); m/z=290.03 $[M+H]^+$

Step C:

A suspension of N-(5-chlorothiazolo[4,5-b]pyridin-2-yl)benzamide (14.80 g, 51.1 mmol) in 70% $H_2SO_4$ (50 mL) was heated at 120° C. for 4 hours. The reaction mixture was cooled to room temperature and the reaction mixture was slowly poured into 500 mL of cold water (00° C.). Then, the reaction mixture was adjusted to basic pH by addition of solid NaOH. Then, the solid was filtered, washed with 1 NaOH (2×250 mL), aqueous saturated solution of $NH_4Cl$ (250 mL), water (2×250 mL) and dried to dryness. The solid was dissolved in DCM/MeOH and filtered through a plug of silica. The plug was then washed with 40% MeOH in DCM and the mother liquor was concentrated to dryness to give the desired product (6.0 g, 64%).

$^1$H-NMR (400 MHz, DMSO-$d_6$) δ 8.19 (s, 2H), 8.08 (d, 1H), 7.05 (d, 1H).

MS (ESI); m/z=186.01 $[M+H]^+$

Step D:

To a suspension of 5-chlorothiazolo[4,5-b]pyridin-2-amine (7.90 g, 42.6 mmol) in acetonitrile (100 mL) at 00° C. was added tert-butyl nitrite (8.44 ml, 63.8 mmol) over 30 min with a syringe pump. Then, copper(II) bromide (11.41 g, 51.1 mmol) was added portionwise. After 30 minutes at 0° C., the reaction mixture was allowed to warm to room temperature and stirred for 6 hours. Water and EtOAc were added and the mixture was filtered. Then, the solid was washed with DCM/MeOH. The mother liquors were separated and the aqueous phase was washed several times with DCM/MeOH. The combined organics were washed with water (2×200 mL), brine, dried over $Na_2SO_4$, filtered and concentrated under reduced pressure. The solid was dissolved in DCM/MeOH and filtered through a plug of silica. The plug was then washed with 5% MeOH in DCM and the mother liquor was concentrated to dryness. The solid was triturated in hot EtOAc. After cooling, the solid was filtered and the mother liquor was concentrated under reduced pressure. The residue was purified on HP-Sil SNAP cartridges using a Biotage Isolera One purification system employing methanol/dichloromethane eluent (2/98→5/95) to afford the title compound (10.6 g, 70%).

$^1H$ NMR (400 MHz, DMSO-d6) δ 8.76-8.59 (m, 1H), 7.65 (d, J=4.7 Hz, 1H).

MS (ESI); m/z=250.86 $[M+H]^+$

Preparative Example 4b

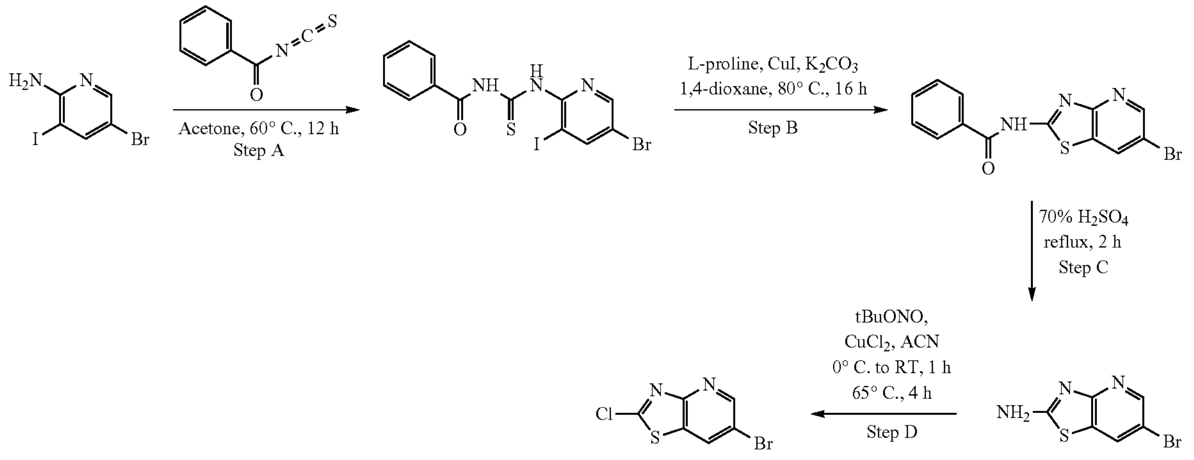

Step A:

A solution of 5-bromo-3-iodopyridin-2-amine (30.0 g, 100.36 mmol) and benzoyl isothiocyanate (16.1 ml, 120.44 mmol, 1.2 eq) in acetone (600 mL, 20 vol) was stirred at 60° C. for 12 hours, the reaction was monitored by TLC. The solvent was evaporated and the solid was filtered, washed with n-hexane (500 mL) and dried to give the desired product as an off white solid (42.0 g, 91%).

$^1H$-NMR (500 MHz, CDCl3) δ 12.55 (br.s, 1H), 9.31 (br.s, 1H), 8.58 (s, 1H), 8.37 (d, 1H), 7.93-7.92 (m, 2H), 7.68 (t, 1H), 7.57-7.52 (m, 2H).

MS (ESI); m/z=461.5 $[M-H]^+$

Step B:

To a solution of N-((5-bromo-3-iodopyridin-2-yl)carbamothioyl)benzamide (42.0 g, 90.91 mmol) in 1,4-dioxane (630 mL, 15 vol) was added potassium carbonate (18.81 g, 136.36 mmol, 1.5 eq), L-proline (2.09 g, 18.18 mmol, 0.2 eq) and copper(I) iodide (3.45 g, 18.18 mmol, 0.2 eq). Then, the reaction mixture was stirred at 80° C. for 16 hours, the reaction was monitored by TLC. The reaction mixture was poured into 1.0 L of water and 1.0 L of aqueous saturated solution of $NH_4Cl$. The suspension was stirred at room temperature for 1 hour. The solid was filtered, washed with aqueous saturated solution of $NH_4Cl$ (2×500 mL), water (2×500 mL) and dried to give the desired product as an off white solid (28.6 g, 94%).

$^1H$-NMR (500 MHz, DMSO-$d_6$) δ 8.76 (d, 1H), 8.63 (d, 1H), 8.16 (d, 2H), 7.68 (t, 1H), 7.58 (t, 2H), 7.25 (brs, 1H).

MS (ESI); m/z=334.51 $[M]^+$

Step C:

A suspension of N-(6-bromothiazolo[4,5-b]pyridin-2-yl) benzamide (7.5 g, 22.45 mmol) in 70% $H_2SO_4$ (22.5 mL, 3.0 vol) was heated at 120° C. for 2 hours. The reaction mixture was cooled to room temperature and the reaction mixture was slowly poured into 500 mL of cold water (00° C.). Then, the reaction mixture was adjusted to basic pH by addition of solid 50% aq. NaOH. Then, the compound was extracted with EtOAc (6×250 mL). The combined organic layers were dried over with $Na_2SO_4$ and filtered, then the solvent was concentrated, and gave the desired product as a light yellow solid (2.75 g, 53%).

$^1H$-NMR (500 MHz, DMSO-$d_6$) δ 8.31 (d, 1H), 8.27 (br.s, 2H), 8.08 (d, 1H).

MS (ESI); m/z=230.4 $[M]^+$

Step D:

To a suspension of 6-bromothiazolo[4,5-b]pyridin-2-amine (13.0 g, 56.52 mmol) in acetonitrile (163 mL, 12.5 vol) at 00° C. was added tert-butyl nitrite (10.1 ml, 84.78 mmol, 1.5 eq) over a period of 10 min with a syringe. Then, copper(II) chloride (9.1 g, 67.82 mmol, 1.2 eq) was added portionwise. After 30 minutes at 00° C., the reaction mixture was allowed to warm to room temperature for 1 hour and heated to 65° C., then stirred for 4 hours. The progress of the reaction was monitored by TLC. After completion of the reaction, the solvent was evaporated. The reaction mixture was diluted with water (100 mL) and 5% MeOH/DCM (3×200 mL). The combined organics were washed with brine (100 mL), dried over $Na_2SO_4$, filtered and concentrated under reduced pressure. The residue was purified on HP-Sil SNAP cartridges using a Biotage Isolera One purification system employing methanol/dichloromethane eluent (1/99) to afford the title compound (10.6 g, 50%).

$^1$H NMR (500 MHz, DMSO-$d_6$) δ 8.90 (d, 1H), 8.81 (d, 1H).

MS (ESI); m/z=249.3 $[M]^+$

Preparative Example 5

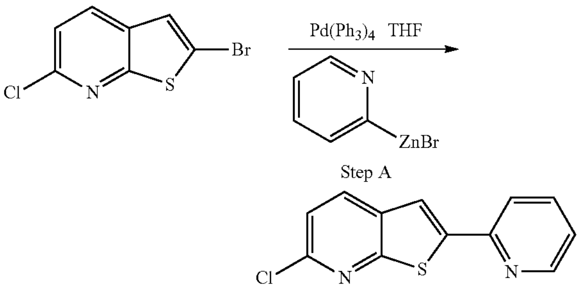

Step A:

A mixture of commercially available 2-bromo-6-chloro-thieno[2,3-b]pyridine (0.15 g, 0.6 mmol), 2-pyridylzinc bromide solution 0.5 M in tetrahydrofuran (1.8 ml, 0.9 mmol) was stirred at room temperature and tetrakis(triphenylphosphine)palladium(0) was added. The reaction mixture was degassed with a stream of argon for 10 minutes and stirred at room temperature overnight. Then the mixture was taken up in ethyl acetate (20 mL), washed with ammonium chloride saturated solution (2×20 ml), dried over $Na_2SO_4$, and concentrated under reduced pressure. The residue was purified on HP-Sil SNAP cartridges using a Biotage Isolera One purification system employing ethyl acetate/n-heptane gradient (100/0→50/50) to afford the title compound (110 mg, 74%).

$^1$H NMR (400 MHz, Chloroform-d) δ 8.67 (dt, 1H), 7.99 (d, 1H), 7.83-7.76 (m, 2H), 7.74 (s, 1H), 7.31 (d, 1H), 7.29-7.24 (m, 1H).

Preparative Example 6

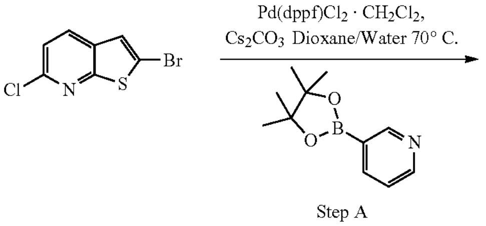

-continued

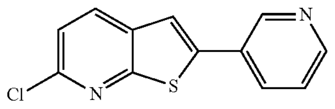

Step A:

A mixture of commercially available 2-bromo-6-chloro-thieno[2,3-b]pyridine (0.30 g, 1.207 mmol), 3-(4,4,5,5-tetramethyl-1,3,2-dioxaborolan-2-yl)pyridine (0.295 g, 1.44 mmol), cesium carbonate (0.780 g, 2.414 mmol) and [1,1'-bis(diphenylphosphino)ferrocene]dichloropalladium(II) complex with dichloromethane (0.05 g, 0.06 mmol) were added into a dry pressure tube, followed by degassed dioxane (8 ml) and degassed water (2 ml). The reaction mixture was degassed with a stream of argon for 10 minutes and heated at 70° C. for 2 h. Then the mixture was cooled at room temperature, taken up in ethyl acetate (20 mL), washed with water (2×20 ml) and brine (10 ml), dried over $Na_2SO_4$, and concentrated under reduced pressure. The residue was purified on HP-Sil SNAP cartridges using a Biotage Isolera One purification system employing ethyl acetate/n-heptane gradient (20/80→50/50) to afford the title compound (220 mg, 74%).

$^1$H-NMR (400 MHz, Chloroform-d) δ 8.99 (d, 1H), 8.64 (dd, 1H), 8.02 (d, 1H), 7.97 (dt, 1H), 7.53 (s, 1H), 7.41 (dd, 1H), 7.36 (d, 1H).

MS (ESI); m/z=246.74 $[M+H]^+$

Preparative Examples 7 to 28

Following the Pd-coupling procedure as described in Preparative Example 6, using the bromo-chloro starting material and the appropriate boronic acid or ester indicated in the table below, the following compounds were prepared. The palladium source [1,1'-bis(diphenylphosphino)ferrocene]dichloropalladium(II) complex with dichloromethane can be replaced by tetrakis(triphenylphosphine)palladium (0). Cesium carbonate can be replaced by potassium carbonate.

TABLE 1

| Bromo chloro Starting Material | Boronic acid/ester | Product Example | 1. Yield<br>2. $^1$H-NMR<br>3. $MH^+$(ESI) |
|---|---|---|---|
| 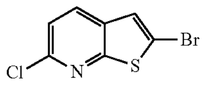 | 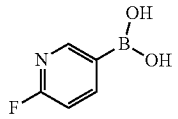 | 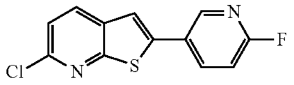<br>7 | 1. 8%<br>2. $^1$H-NMR (400 MHz, DMSO-$d_6$) δ 8.72 (d, 1H), 8.43 (ddd, 1H), 8.33 (d, 1H), 8.00 (s, 1H), 7.57 (d, 1H), 7.37 (dd, 1H).<br>3. 264.74 |

TABLE 1-continued

| Bromo chloro<br>Starting Material | Boronic acid/ester | Product<br>Example | 1. Yield<br>2. $^1$H-NMR<br>3. MH$^+$(ESI) |
|---|---|---|---|
| 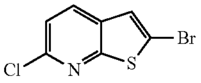 | 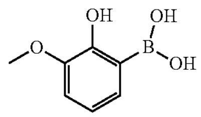 | 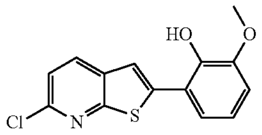<br>8 | 1. 24%<br>2. $^1$H-NMR (400 MHz, DMSO-d$_6$) δ 9.82 (s, 1H), 8.28 (d, 1H), 7.94 (s, 1H), 7.49 (d, 1H), 7.35 (dd, 1H), 7.03 (dd, 1H), 6.91 (t, 1H), 3.87 (s, 3H). |
| 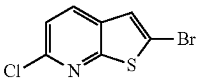 [SMILES: Clc1ccc2cc(Br)sc2n1] | 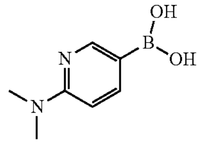 | 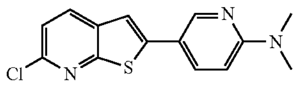<br>9 | 1. 37%<br>2. $^1$H-NMR (400 MHz, DMSO-d$_6$) δ 8.54 (d, 1H), 8.20 (d, 1H), 7.92 (dd, 1H), 7.69 (s, 1H), 7.50 (d, 1H), 6.78 (d, 1H), 3.11 (s, 6H).<br>3. 290.0 |
| 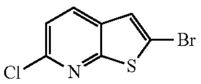 | 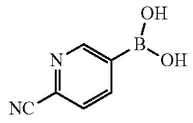 [SMILES: N#Cc1ccc(B(O)O)cn1] | 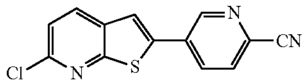<br>10 | 1. 58%<br>2. $^1$H-NMR (400 MHz, DMSO-d$_6$) δ 9.26 (s, 1H), 8.43 (dd, 2H), 8.34-8.12 (m, 2H), 7.63 (d, 1H). |
| 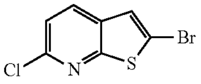 | 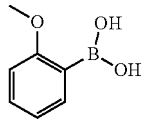 | 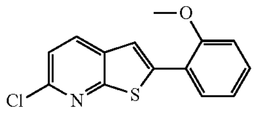<br>11 | 1. 65%<br>2. $^1$H-NMR (400 MHz, DMSO-d$_6$) δ 8.28 (d, 1H), 7.94 (s, 1H), 7.83 (dd, 1H), 7.51 (d, 1H), 7.48-7.39 (m, 1H), 7.23 (d, 1H), 7.10 (t, 1H), 3.96 (s, 3H).<br>3. 276.06 |
| 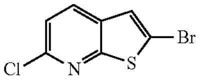 [SMILES: Clc1ccc2cc(Br)sc2n1] | 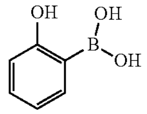 | 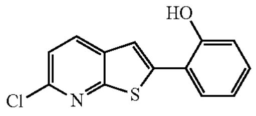<br>12 | 1. 68%<br>2. $^1$H-NMR (400 MHz, DMSO-d$_6$) δ 10.60 (s, 1H), 8.28 (d, 1H), 7.96 (s, 1H), 7.74 (dd, 1H), 7.50 (d, 1H), 7.26 (ddd, 1H), 7.03 (dd, 1H), 7.00-6.91 (m, 1H).<br>3. 262.28 |
| 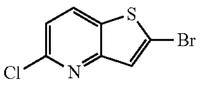 | 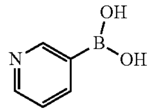 | 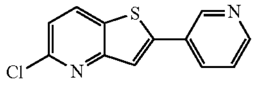<br>13 | 1. 52%<br>2. $^1$H-NMR (400 MHz, DMSO-d$_6$) δ 9.12 (d, 1H), 8.66 (dd, 1H), 8.59 (d, 1H), 8.28 (dt, 1H), 8.16 (s, 1H), 7.57 (dd, 1H), 7.50 (d, 1H).<br>3. 274.02 |
| 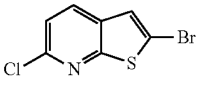 [SMILES: Clc1ccc2cc(Br)sc2n1] | 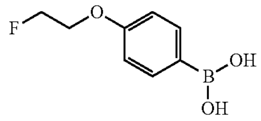 [SMILES: OB(O)c1ccc(OCCF)cc1] | 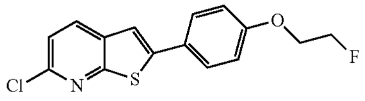<br>14 | 1. 56%<br>2. $^1$H-NMR (400 MHz, DMSO-d$_6$) δ 8.23 (d, 1H), 7.84-7.69 (m, 3H), 7.51 (d, 1H), 7.11 (d, 2H), 4.83 (t, 1H), 4.77-4.66 (m, 1H), 4.35 (t, 1H), 4.28 (t, 1H).<br>3. 308.08 |

TABLE 1-continued

| Bromo chloro Starting Material | Boronic acid/ester | Product Example | 1. Yield 2. $^1$H-NMR 3. MH$^+$(ESI) |
|---|---|---|---|
| 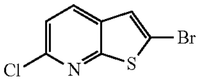 [SMILES: Clc1ccc2cc(Br)sc2n1] | 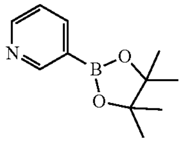 | 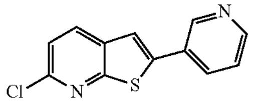 15 | 1. 74% 2. $^1$H-NMR (400 MHz, DMSO-d$_6$) δ 9.04 (d, 1H), 8.71-8.57 (m, 1H), 8.32 (d, 1H), 8.26-8.14 (m, 1H), 8.03 (s, 1H), 7.64-7.43 (m, 2H). 3. 247.06 |
| 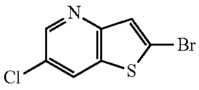 | 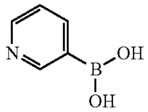 | 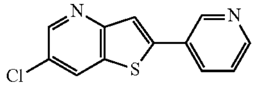 16 | 1. 72% 2. $^1$H-NMR (400 MHz, DMSO-d$_6$) δ 9.11 (d, 1H), 8.75 (d, 1H), 8.69 (d, 1H), 8.64 (d, 1H), 8.27 (d, 1H), 8.20 (s, 1H), 7.55 (dd, 1H). 3. 247.00 |
| 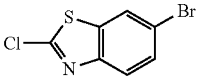 | 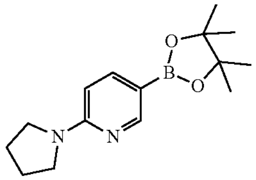 [SMILES: CC1(C)OB(c2ccc(N3CCCC3)nc2)OC1(C)C] | 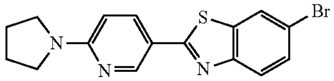 17 | 1. 64% 2. $^1$H-NMR (400 MHz, DMSO-d$_6$) δ 8.76 (s, 1H), 8.35 (s, 1H), 8.16-8.05 (m, 1H), 7.86 (d, 1H), 7.62 (d, 1H), 6.68-6.52 (m, 1H), 3.48 (s, 4H), 1.97 (s, 4H). 3. 360.01 |
| 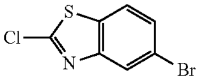 | 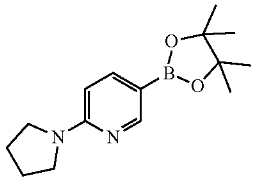 [SMILES: CC1(C)OB(c2ccc(N3CCCC3)nc2)OC1(C)C] | 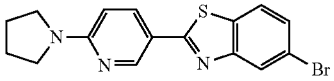 18 | 1. 47% 2. $^1$H-NMR (400 MHz, DMSO-d$_6$) δ 8.77 (s, 1H), 8.25-7.95 (m, 3H), 7.54 (d, 1H), 6.61 (d, 1H), 3.49 (s, 4H), 1.98 (s, 4H). 3. NA |
| 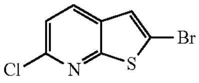 [SMILES: Clc1ccc2cc(Br)sc2n1] | 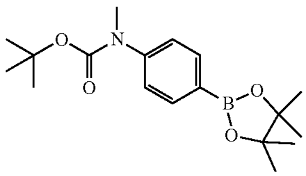 [SMILES: CN(C(=O)OC(C)(C)C)c1ccc(B2OC(C)(C)C(C)(C)O2)cc1] | 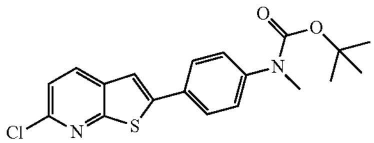 19 | 1. 45% 2. $^1$H-NMR (400 MHz, DMSO-d$_6$) δ 8.27 (d, 1H), 7.87 (s, 1H), 7.77 (d, 2H), 7.53 (d, 1H), 7.43 (d, 2H), 3.23 (s, 3H), 1.42 (s, 9H). 3. 374.90 |
| 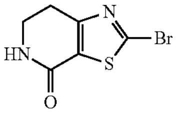 [SMILES: O=C1NCCc2nc(Br)sc21] | 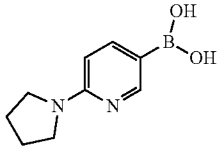 [SMILES: OB(O)c1ccc(N2CCCC2)nc1] | 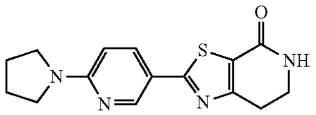 20 | 1. 91% 2. $^1$H-NMR (400 MHz, DMSO-d$_6$) δ 8.80-8.60 (m, 1H), 7.99 (dd, 1H), 7.77 (s, 1H), 6.55 (d, 1H), 3.55-3.38 (m, 6H), 2.97 (t, 2H), 2.07-1.86 (m, 4H) 3. 301.27 |
| 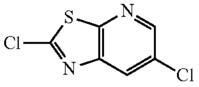 [SMILES: Clc1cnc2sc(Cl)nc2c1] | 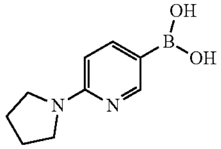 [SMILES: OB(O)c1ccc(N2CCCC2)nc1] | 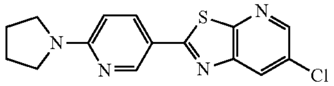 21 | 1. 47% 2. $^1$H-NMR (400 MHz, DMSO-d$_6$) δ 8.90-8.71 (m, 1H), 8.56 (s, 1H), 8.53-8.40 (m, 1H), 8.20-8.04 (m, 1H), 6.63 (d, 1H), 3.50 (s, 4H), 1.98 (s, 4H). 3. 316.76 |

TABLE 1-continued

| Bromo chloro<br>Starting Material | Boronic acid/ester | Product<br>Example | 1. Yield<br>2. $^1$H-NMR<br>3. $MH^+$(ESI) |
|---|---|---|---|
| 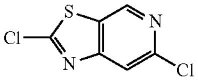 [SMILES: Clc1cc2nc(Cl)sc2cn1] | 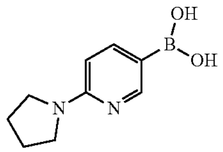 [SMILES: OB(O)c1ccc(N2CCCC2)nc1] | 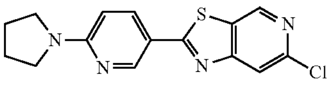<br>22 | 1. 17%<br>2. $^1$H-NMR (400 MHz, DMSO-$d_6$) δ 9.10 (s, 1H), 8.86 (d, 1H), 8.15 (dd, 1H), 8.00 (s, 1H), 6.63 (d, 1H), 3.51 (s, 4H), 1.98 (s, 4H)<br>3. 317.22 |
| 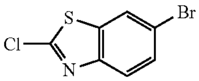 | 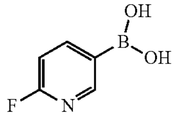 | 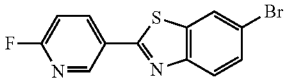<br>23 | 1. 58%<br>2. $^1$H NMR (400 MHz, DMSO-$d_6$) δ 9.02-8.88 (m, 1H), 8.64 (q, 1H), 8.31 (s, 1H), 8.19 (d, 1H), 7.67 (d, 1H), 7.43 (d, 1H)<br>3. N/A |
| 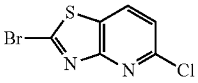 | 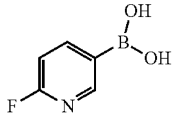 | 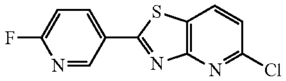<br>24 | 1. 71%<br>2. $^1$H NMR (400 MHz, DMSO-$d_6$) δ 9.04 (d, 1H), 8.78 (d, 1H), 8.72 (td, 1H), 7.65 (d, 1H), 7.47 (dd, 1H)<br>3. N/A |
| 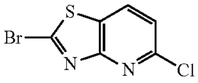 | 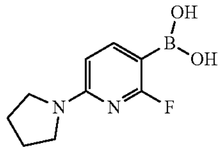 [SMILES: OB(O)c1ccc(N2CCCC2)nc1F] | 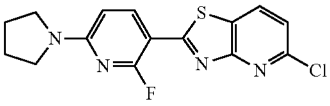<br>25 | 1. 55%<br>2. N/A<br>3. 334.96 |
| 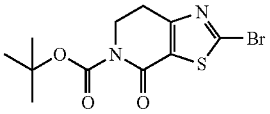 [SMILES: CC(C)(C)OC(=O)N1CCc2nc(Br)sc2C1=O] | 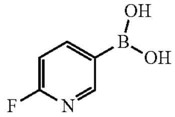 | 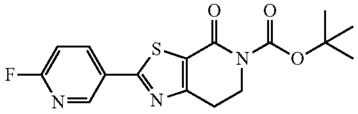<br>26 | 1. 63%<br>2. $^1$H NMR (400 MHz, Chloroform-d) δ 8.84 (d, 1H), 8.36 (ddd, 1H), 7.06 (dd, 1H), 4.18 (t, 2H), 3.17 (t, 2H), 1.58 (s, 9H)<br>3. 350.80 |
| 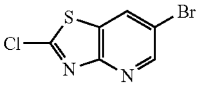 | 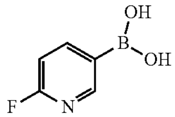 | 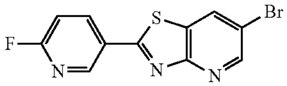<br>27 | 1. 50%<br>2. $^1$H NMR (500 MHz, DMSO-$d_6$) δ 9.10-9.01 (m, 2H), 8.84 (d, 1H), 8.74 (td, 1H), 7.46 (dd, 1H).<br>3. 310.1 |
| 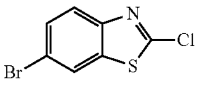 | 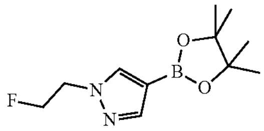 [SMILES: CC1(C)OB(c2cnn(CCF)c2)OC1(C)C] | 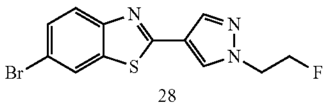 [SMILES: FCCn1cc(-c2nc3ccc(Br)cc3s2)cn1]<br>28 | 1. 45%<br>2. $^1$H NMR (400 MHz, DMSO-$d_6$) δ 8.61 (s, 1H), 8.38 (s, 1H), 8.15 (s, 1H), 7.87 (d, 1H), 7.64 (d, 1H), 4.94-4.75 (m, 2H), 4.61-4.47 (m, 2H)<br>3. 326.10 |

Example 1

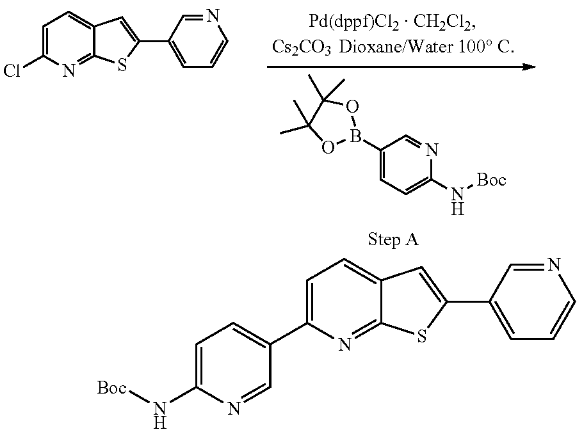

Step A:

The title compound from Preparative Example 6 above (0.05 g, 0.203 mmol), tert-butyl (5-(4,4,5,5-tetramethyl-1,3,2-dioxaborolan-2-yl)pyridin-2-yl)carbamate (0.078 g, 0.243 mmol), cesium carbonate (0.13 g, 0.406 mmol) and [1,1'-bis(diphenylphosphino)ferrocene]dichloropalladium(II) complex with dichloromethane (0.08 g, 0.01 mmol) were added into a dry pressure tube, followed by degassed dioxane (4 ml) and degassed water (1 ml). The reaction mixture was degassed with a stream of argon for 10 minutes and heated at 100° C. for 4 h. The mixture then was cooled to room temperature, taken up in ethyl acetate (20 mL), washed with water (2×20 ml) and brine (10 ml), dried over $Na_2SO_4$, and concentrated under reduced pressure. The residue was purified on HP-Sil SNAP cartridges using a Biotage Isolera One purification system employing ethyl acetate/n-heptane gradient (50/50→90/10) to afford the title compound (42 mg, 52%).

$^1$H-NMR (400 MHz, Chloroform-d) δ 9.02 (dd, 2H), 8.63 (dd, 1H), 8.42 (dd, 1H), 8.11 (dd, 2H), 8.01 (dt, 1H), 7.78-7.65 (m, 2H), 7.56 (s, 1H), 7.41 (dd, 1H), 1.57 (d, 9H).

MS (ESI); m/z=348.89 $[M+H]^+$

Examples 2 to 25, 81 to 87 and 94 to 104

Following the Pd-coupling procedure as described in Example 1, using the chloro starting material and the appropriate boronic acid or ester indicated in the table below, the following compounds were prepared. The palladium source [1,1'-bis(diphenylphosphino)ferrocene]dichloropalladium (II) complex with dichloromethane can be replaced by tetrakis(triphenylphosphine)palladium(0). Cesium carbonate can be replaced by potassium carbonate.

TABLE 2

| Chloro Starting Material | Boronic acid/ester | Product Example | 1. Yield<br>2. $^1$H-NMR<br>3. MH$^+$ (ESI) |
|---|---|---|---|
| 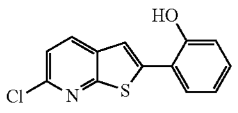 [SMILES: Oc1ccccc1-c1cc2ccc(Cl)nc2s1] | 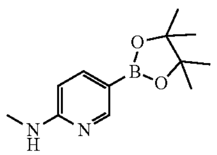 | 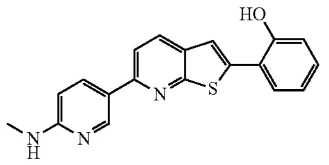<br>2 | 1. 12%<br>2. $^1$H-NMR (400 MHz, DMSO-d$_6$) δ 10.49 (s, 1H), 8.96-8.76 (m, 1H), 8.20 (d, 2H), 8.08-7.80 (m, 2H), 7.71 (d, 1H), 7.24 (t, 1H), 7.18-6.83 (m, 3H), 6.58 (d, 1H), 2.86 (d, 3H).<br>3. 334.14 |
| 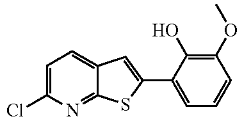 | 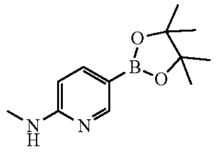 | 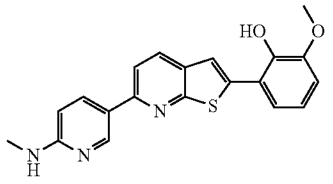<br>3 | 1. 9%<br>2. $^1$H-NMR (400 MHz, Chloroform-d) δ 8.78 (d, 1H), 8.33 (dd, 1H), 8.03 (d, 1H), 7.83 (s, 1H), 7.64 (d, 1H), 7.33-7.25 (m, 1H), 6.98-6.81 (m, 2H), 6.55 (d, 1H), 3.98 (s, 3H), 3.02 (d, 3H).<br>3. 363.8 |
| 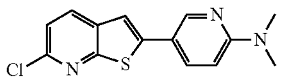 [SMILES: CN(C)c1ccc(-c2cc3ccc(Cl)nc3s2)cn1] | 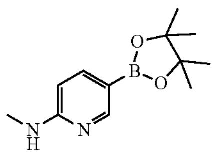 | 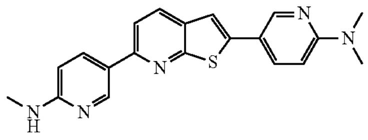<br>4 | 1. 32%<br>2. $^1$H-NMR (400 MHz, DMSO-d$_6$) δ 8.80 (d, 1H), 8.52 (d, 1H), 8.16 (dd, 1H), 8.10 (d, 1H), 7.91 (dd, 1H), 7.85 (d, 1H), 7.61 (s, 1H), 6.90 (d, 1H), 6.76 (d, 1H), 6.56 (d, 1H), 3.10 (s, 6H), 2.84 (d, 3H).<br>3. 362.46 |

TABLE 2-continued

| Chloro Starting Material | Boronic acid/ester | Product Example | 1. Yield 2. $^1$H-NMR 3. $MH^+$ (ESI) |
|---|---|---|---|
| 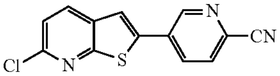 | 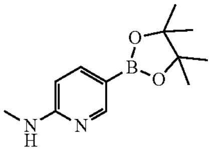 | 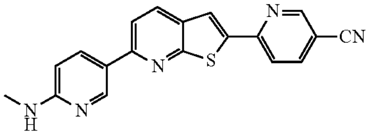 5 | 1. 24% 2. $^1$H-NMR (400 MHz, DMSO-$d_6$) δ 9.23 (d, 1H), 8.85 (d, 1H), 8.41 (dd, 1H), 8.27 (d, 1H), 8.24-8.17 (m, 2H), 8.15 (d, 1H), 7.96 (d, 1H), 7.00 (d, 1H), 6.57 (d, 1H), 2.85 (d, 3H). 3. 344.45 |
| 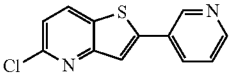 [SMILES: Clc1ccc2sc(-c3cccnc3)cc2n1] | 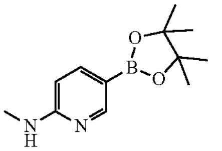 | 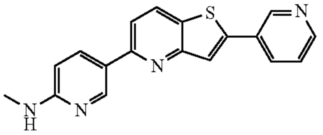 6 | 1. 10% 2. $^1$H-NMR (400 MHz, DMSO-$d_6$) δ 9.11 (d, 1H), 8.82 (d, 1H), 8.69-8.57 (m, 1H), 8.47 (d, 1H), 8.27 (dt, 1H), 8.18 (d, 1H), 7.85 (d, 1H), 7.55 (dd, 1H), 6.88 (d, 1H), 6.57 (d, 1H), 2.85 (d, 3H). 3. 319.16 |
| 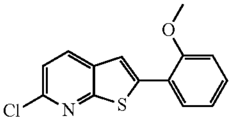 [SMILES: COc1ccccc1-c1cc2ccc(Cl)nc2s1] | 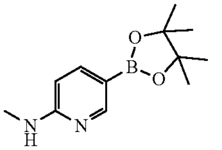 | 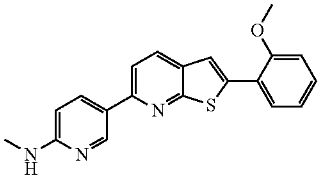 7 | 1. 22% 2. $^1$H-NMR (400 MHz, DMSO-$d_6$) δ 8.84 (d, 1H), 8.20 (dd, 2H), 7.89 (d, 2H), 7.81 (dd, 1H), 7.49-7.35 (m, 1H), 7.23 (d, 1H), 7.11 (t, 1H), 6.92 (d, 1H), 6.58 (d, 1H), 3.98 (s, 3H), 2.87 (d, 3H). 3. 348.15 |
| 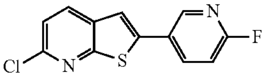 [SMILES: Fc1ccc(-c2cc3ccc(Cl)nc3s2)cn1] | 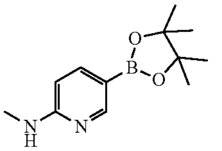 | 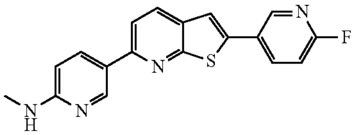 8 | 1. 41% 2. $^1$H.NMR (400 MHz, DMSO-$d_6$) δ 8.85 (d, 1H), 8.72 (d, 1H), 8.43 (td, 1H), 8.33-8.17 (m, 2H), 8.03-7.84 (m, 2H), 7.37 (dd, 1H), 6.96 (q, 1H), 6.59 (d, 1H), 2.87 (d, 3H). 3. 337.1 |
| 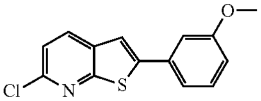 [SMILES: COc1cccc(-c2cc3ccc(Cl)nc3s2)c1] | 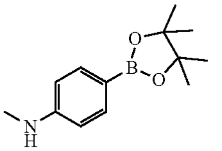 | 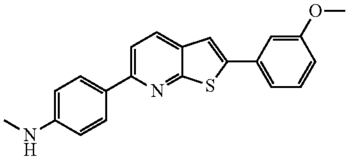 9 | 1. 5% 2. $^1$H-NMR (400 MHz, DMSO-$d_6$) δ 8.15 (d, 1H), 8.03-7.94 (m, 2H), 7.91-7.81 (m, 2H), 7.44-7.33 (m, 3H), 7.05-6.95 (m, 1H), 6.71-6.57 (m, 2H), 6.12 (d, 1H), 3.86 (s, 3H), 2.84-2.67 (m, 3H). 3. 346.76 |
| 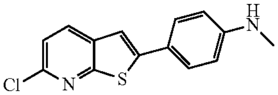 [SMILES: CNc1ccc(-c2cc3ccc(Cl)nc3s2)cc1] | 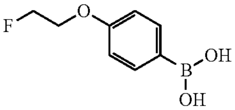 [SMILES: OB(O)c1ccc(OCCF)cc1] | 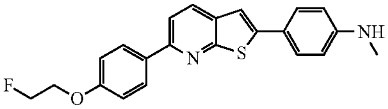 10 | 1. 30% 2. $^1$H-NMR (400 MHz, DMSO-$d_6$) δ 8.11 (d, 3H), 7.90 (d, 1H), 7.55 (d, 2H), 7.51 (s, 1H), 7.10 (d, 2H), 6.63 (d, 2H), 6.15 (q, 1H), 4.85-4.83 (m, 1H), 4.73-4.71 (m, 1H), 4.37-4.35 (m, 1H), 4.29-4.27 (m, 1H), 2.74 (d, 3H). 3. 379.08 |

TABLE 2-continued
| Chloro Starting Material | Boronic acid/ester | Product Example | 1. Yield 2. $^{1}$H-NMR 3. MH$^{+}$ (ESI) |
|---|---|---|---|
| 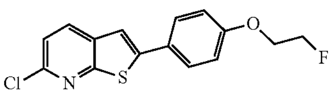 [SMILES: FCCOc1ccc(-c2cc3ccc(Cl)nc3s2)cc1] | 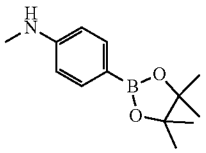 | 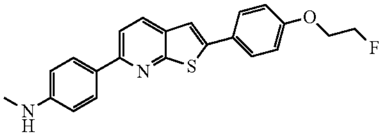 11 | 1. 34% 2. $^{1}$H-NMR (400 MHz, DMSO-$d_6$) δ 8.10 (d, 1H), 7.95 (d, 2H), 7.82 (d, 1H), 7.73 (d, 2H), 7.67 (s, 1H), 7.10 (d, 2H), 6.64 (d, 2H), 6.09 (q, 1H), 4.89-4.79 (m, 1H), 4.76-4.68 (m, 1H), 4.40-4.31 (m, 1H), 4.31-4.22 (m, 1H), 2.75 (d, 3H). 3. 378.96 |
| 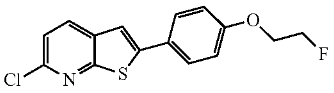 [SMILES: FCCOc1ccc(-c2cc3ccc(Cl)nc3s2)cc1] | 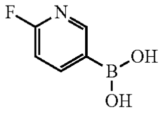 | 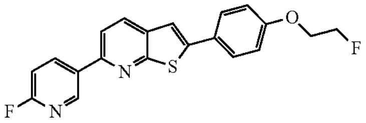 12 | 1. 22% 2. $^{1}$H-NMR (400 MHz, DMSO-$d_6$) δ 9.01 (s, 1H), 8.72 (dt, 1H), 8.30 (d, 1H), 8.10 (d, 1H), 7.85-7.69 (m, 3H), 7.34 (dd, 1H), 7.12 (d, 2H), 4.84 (t, 1H), 4.72 (t, 1H), 4.36 (t, 1H), 4.29 (t, 1H). 3. 368.91 |
| 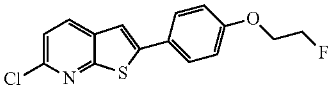 [SMILES: FCCOc1ccc(-c2cc3ccc(Cl)nc3s2)cc1] | 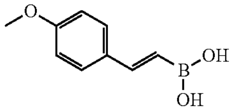 | 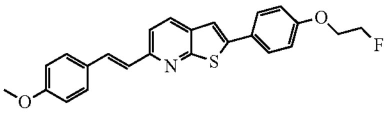 13 | 1. 18% 2. $^{1}$H-NMR (400 MHz, DMSO-$d_6$) δ 8.12 (d, 1H), 7.75 (d, 2H), 7.72-7.62 (m, 4H), 7.57 (d, 1H), 7.27 (d, 1H), 7.11 (d, 2H), 6.99 (d, 2H), 4.87-4.80 (m, 1H), 4.75-4.67 (m, 1H), 4.39-4.32 (m, 1H), 4.32-4.25 (m, 1H), 3.80 (s, 3H). 3. 406.02 |
| 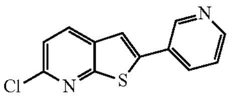 [SMILES: Clc1ccc2cc(-c3cccnc3)sc2n1] | 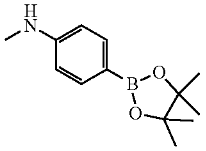 | 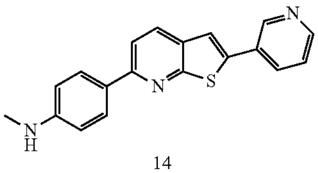 [SMILES: CNc1ccc(-c2ccc3cc(-c4cccnc4)sc3n2)cc1] 14 | 1. 66% 2. $^{1}$H-NMR (400 MHz, DMSO-$d_6$) δ 9.03 (s, 1H), 8.59 (d, 1H), 8.18 (d, 2H), 8.06-7.92 (m, 3H), 7.88 (d, 1H), 7.53 (dd, 1H), 6.65 (d, 2H), 6.15 (d, 1H), 2.75 (d, 3H). 3. 317.86 |
| 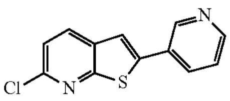 [SMILES: Clc1ccc2cc(-c3cccnc3)sc2n1] | 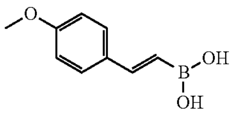 | 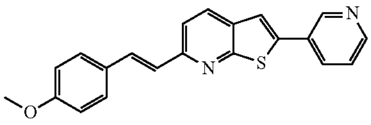 15 | 1. 67% 2. 3. 344.9 |

TABLE 2-continued

| Chloro Starting Material | Boronic acid/ester | Product Example | 1. Yield<br>2. $^1$H-NMR<br>3. MH$^+$ (ESI) |
|---|---|---|---|
| 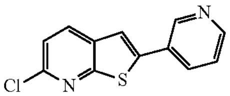 [SMILES: Clc1ccc2cc(-c3cccnc3)sc2n1] | 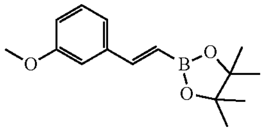 | 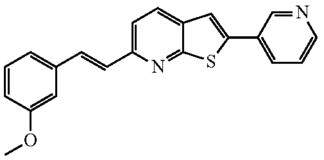<br>16 | 1. 78%<br>2. $^1$H-NMR (400 MHz, DMSO-$d_6$) δ 9.06 (d, 1H), 8.67-8.56 (m, 1H), 8.23 (dd, 2H), 8.00 (s, 1H), 7.76 (d, 1H), 7.67 (d, 1H), 7.54 (dd, 1H), 7.47 (d, 1H), 7.38-7.27 (m, 3H), 6.92 (d, 1H), 3.82 (s, 3H).<br>3. 344.83 |
| 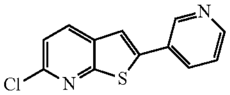 [SMILES: Clc1ccc2cc(-c3cccnc3)sc2n1] | 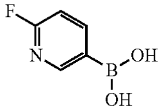 | 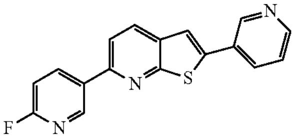<br>17 | 1. 66%<br>2. $^1$H-NMR (400 MHz, DMSO-$d_6$) δ 9.05 (d, 2H), 8.74 (t, 1H), 8.63 (d, 1H), 8.39 (d, 1H), 8.23 (d, 1H), 8.15 (d, 1H), 8.05 (s, 1H), 7.64-7.49 (m, 1H), 7.36 (d, 1H).<br>3. 307.81 |
| 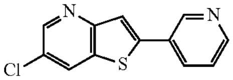 [SMILES: Clc1cnc2cc(-c3cccnc3)sc2c1] | 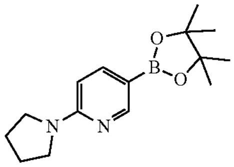 [SMILES: CC1(C)OB(c2ccc(N3CCCC3)nc2)OC1(C)C] | 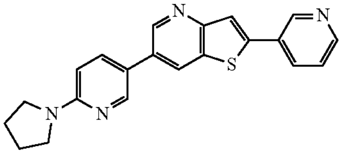<br>18 | 1. 54%<br>2. $^1$H-NMR (400 MHz, DMSO-$d_6$) δ 9.12 (s, 1H), 8.97 (s, 1H), 8.71 (s, 1H), 8.62 (d, 1H), 8.58 (s, 1H), 8.27 (d, 1H), 8.18 (s, 1H), 7.99 (d, 1H), 7.55 (dd, 1H), 6.59 (d, 9H), 3.45 (s, 4H), 1.97 (s, 4H).<br>3. 359.0 |
| 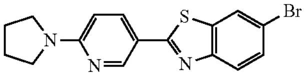 [SMILES: Brc1ccc2nc(-c3ccc(N4CCCC4)nc3)sc2c1] | 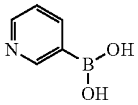 | 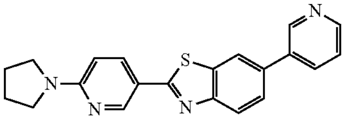<br>19 | 1. 70%<br>2. $^1$H-NMR (400 MHz, DMSO-$d_6$) δ 8.99 (d, 1H), 8.80 (d, 1H), 8.59 (dd, 1H), 8.48 (d, 1H), 8.17 (dt, 1H), 8.13 (dd, 1H), 8.04 (d, 1H), 7.85 (dd, 1H), 7.52 (dd, 1H), 6.61 (d, 1H), 3.49 (s, 4H), 1.98 (s, 4H).<br>3. 359.11 |
| 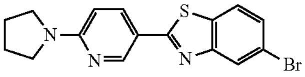 [SMILES: Brc1ccc2sc(-c3ccc(N4CCCC4)nc3)nc2c1] | 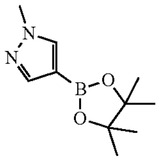 | 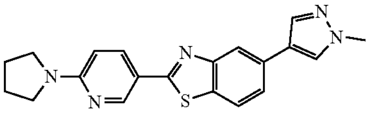<br>20 | 1. 70%<br>2. $^1$H-NMR (400 MHz, DMSO-$d_6$) δ 8.99 (d, 1H), 8.80 (d, 1H), 8.59 (dd, 1H), 8.48 (d, 1H), 8.17 (dt, 1H), 8.13 (dd, 1H), 8.04 (d, 1H), 7.85 (dd, 1H), 7.52 (dd, 1H), 6.61 (d, 1H), 3.49 (s, 4H), 1.98 (s, 4H).<br>3. 359.11 |

TABLE 2-continued

| Chloro Starting Material | Boronic acid/ester | Product Example | 1. Yield 2. $^1$H-NMR 3. MH$^+$ (ESI) |
|---|---|---|---|
| 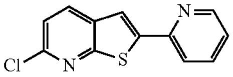 [SMILES: Clc1ccc2cc(-c3ccccn3)sc2n1] | 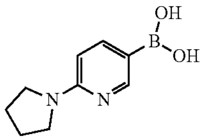 [SMILES: OB(O)c1ccc(N2CCCC2)nc1] | 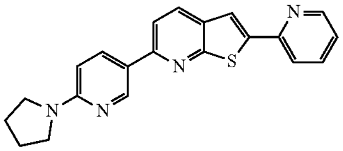 21 | 1. 6% 2. $^1$H NMR (400 MHz, Chloroform-d) δ 8.87 (d, 1H), 8.78-8.61 (m, 1H), 8.35 (dd, 1H), 8.04 (d, 1H), 7.86-7.72 (m, 3H), 7.67 (d, 1H), 7.25 (td, 1H), 6.51 (d, 1H), 3.58 (d, 4H), 2.16-1.99 (m, 4H). 3. 359.17 |
| 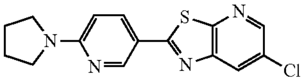 [SMILES: Clc1cnc2sc(-c3ccc(N4CCCC4)nc3)nc2c1] | 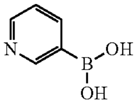 | 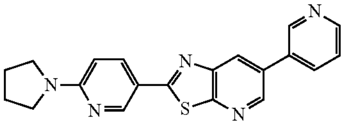 23 | 1. 28% 2. $^1$H-NMR (400 MHz, DMSO-$d_6$) δ 9.11-9.03 (m, 1H), 8.90 (d, 1H), 8.82 (d, 1H), 8.66 (dd, 2H), 8.28 (d, 1H), 8.14 (dd, 1H), 7.56 (dd, 1H), 6.63 (d, 1H), 3.59-3.43 (m, 4H), 2.08-1.87(m, 4H). 3. 360.62 |
| 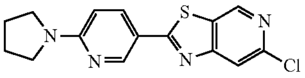 [SMILES: Clc1cc2nc(-c3ccc(N4CCCC4)nc3)sc2cn1] | 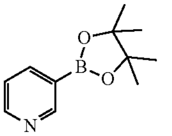 | 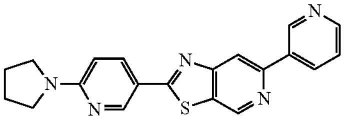 24 | 1. 50% 2. $^1$H-NMR (400 MHz, DMSO-$d_6$) δ 9.39 (s, 2H), 8.98-8.84 (m, 1H), 8.70-8.50 (m, 3H), 8.28-8.11 (m, 1H), 7.54 (dd, 1H), 6.65 (d, 1H), 3.52 (s, 4H), 1.99 (s, 4H). 3. 360.41 |
| 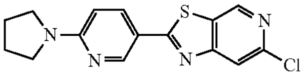 [SMILES: Clc1cc2nc(-c3ccc(N4CCCC4)nc3)sc2cn1] | 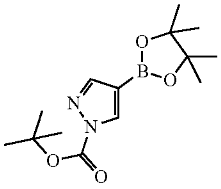 [SMILES: CC(C)(C)OC(=O)n1cc(B2OC(C)(C)C(C)(C)O2)cn1] | 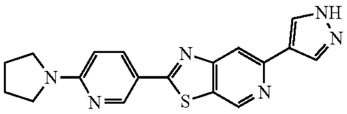 25 | 1. 26% 2. $^1$NMR (400 MHz, DMSO-$d_6$) δ 13.03 (s, 1H), 9.18 (s, 1H), 8.86 (s, 1H), 8.48-8.09 (m, 3H), 7.55 (s, 1H), 6.63 (d, 1H), 3.51 (s, 4H), 1.99 (s, 4H) 3. 349.02 |
| 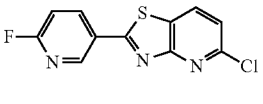 [SMILES: Fc1ccc(-c2nc3nc(Cl)ccc3s2)cn1] | 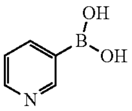 | 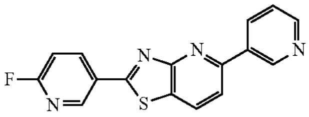 81 | 1. 26% 2. $^1$H NMR (400 MHz, DMSO-$d_6$) δ 9.40 (s, 1H), 9.08 (d, 1H), 8.84 (d, 1H), 8.76 (td, 1H), 8.69 (d, 1H), 8.58 (d, 1H), 8.22 (d, 1H), 7.59 (dd, 1H), 7.47 (dd, 1H) 3. 309.13 |
| 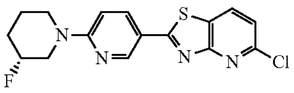 [SMILES: F[C@@H]1CCCN(c2ccc(-c3nc4nc(Cl)ccc4s3)cn2)C1] | 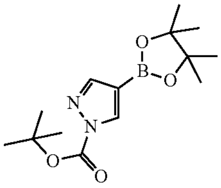 [SMILES: CC(C)(C)OC(=O)n1cc(B2OC(C)(C)C(C)(C)O2)cn1] | 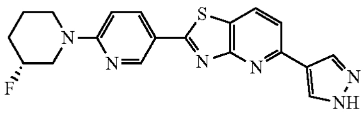 82 | 1. 45% 2. $^1$H NMR (400 MHz, DMSO-$d_6$) δ 13.12 (s, 1H), 8.84 (d, 1H), 8.49 (d, 1H), 8.44 (s, 1H), 8.26-8.12 (m, 2H), 7.74 (d, 1H), 7.05 (d, 1H), 4.82 (d, 1H), 4.24-4.07 (m, 1H), 4.07-3.90 (m, 1H), 3.75 (dd, 1H), 3.53-3.41 (m, 1H), 2.07-1.70 (m, 3H), 1.69-1.51 (m, 1H) 3. 381.04 |

TABLE 2-continued
| Chloro Starting Material | Boronic acid/ester | Product Example | 1. Yield 2. $^1$H-NMR 3. $MH^+$ (ESI) |
|---|---|---|---|
| 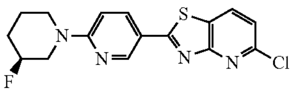 | 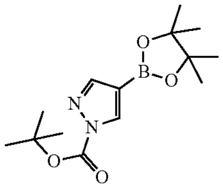 [SMILES: CC(C)(C)OC(=O)n1cc(B2OC(C)(C)C(C)(C)O2)cn1] | 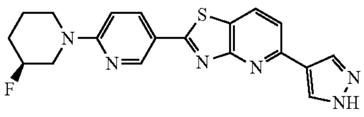 83 | 1. 64% 2. $^1$H NMR (400 MHz, DMSO-$d_6$) δ 13.12 (s, 1H), 8.85 (d, 1H), 8.50 (d, 1H), 8.45 (s, 1H), 8.17 (dd, 2H), 7.74 (d, 1H), 7.06 (d, 1H), 4.83 (d, 1H), 4.15 (ddd, 1H), 3.99 (dt, 1H), 3.86-3.68 (m, 1H), 3.46 (t, 1H), 2.07-1.85 (m, 2H), 1.85-1.70 (m, 1H), 1.66-1.52 (m, 1H) 3. 381.03 |
| 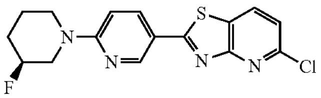 [SMILES: F[C@H]1CCCN(c2ccc(-c3nc4nc(Cl)ccc4s3)cn2)C1] | 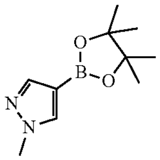 | 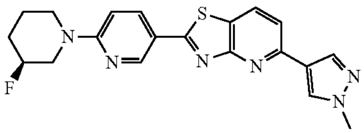 84 | 1. 78% 2. $^1$H NMR (400 MHz, DMSO-$d_6$) δ 8.84 (d, 1H), 8.49 (d, 1H), 8.39 (s, 1H), 8.16 (dd, 1H), 8.09 (s, 1H), 7.68 (d, 1H), 7.05 (d, 1H), 4.82 (d, 1H), 4.25-4.07 (m, 1H), 3.98 (dd, 1H), 3.92 (s, 3H), 3.83-3.67 (m, 1H), 3.45 (t, 1H), 2.09-1.85 (m, 2H), 1.85-1.71 (m, 1H), 1.66-1.48 (m, 1H) 3. 395.08 |
| 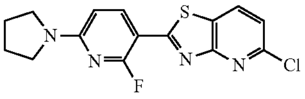 [SMILES: Fc1nc(N2CCCC2)ccc1-c1nc2nc(Cl)ccc2s1] | 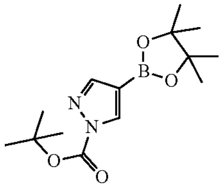 [SMILES: CC(C)(C)OC(=O)n1cc(B2OC(C)(C)C(C)(C)O2)cn1] | 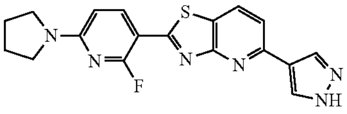 85 | 1. 48% 2. $^1$H NMR (400 MHz, DMSO-$d_6$) δ 13.13 (s, 1H), 8.62-8.30 (m, 3H), 8.17 (s, 1H), 7.74 (d, 1H), 6.72-6.54 (m, 1H), 3.50 (s, 4H), 1.99 (s, 4H) 3. 367.11 |
| 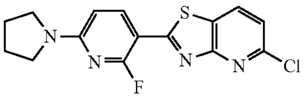 [SMILES: Fc1nc(N2CCCC2)ccc1-c1nc2nc(Cl)ccc2s1] | 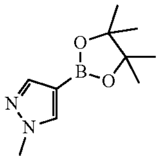 | 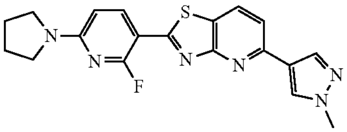 86 | 1. 61% 2. $^1$H NMR (400 MHz, DMSO-$d_6$) δ 8.54-8.46 (m, 2H), 8.39 (s, 1H), 8.09 (s, 1H), 7.68 (d, 1H), 6.61 (dd, 1H), 3.92 (s, 3H), 3.48 (s, 4H), 1.98 (s, 4H) 3. 381.08 |
| 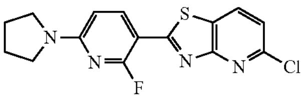 [SMILES: Fc1nc(N2CCCC2)ccc1-c1nc2nc(Cl)ccc2s1] | 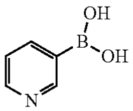 | 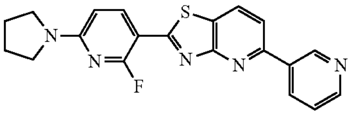 87 | 1. 48% 2. $^1$H NMR (400 MHz, DMSO-$d_6$) δ 9.37 (s, 1H), 8.68 (d, 2H), 8.54 (t, 2H), 8.09 (d, 1H), 7.62-7.50 (m, 1H), 6.71-6.59 (m, 1H), 3.50 (s, 4H), 1.98 (s, 4H) 3. 378.03 |

TABLE 2-continued

| Chloro Starting Material | Boronic acid/ester | Product Example | 1. Yield 2. $^1$H-NMR 3. $MH^+$ (ESI) |
|---|---|---|---|
| 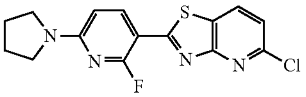 [SMILES: Fc1nc(N2CCCC2)ccc1-c1nc2nc(Cl)ccc2s1] | 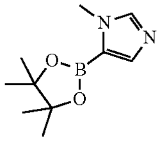 | 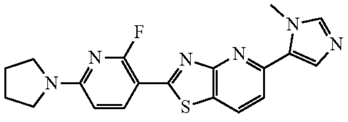 94 | 1. 55% 2. $^1$H NMR (400 MHz, DMSO-$d_6$) δ 8.60-8.44 (m, 2H), 7.86-7.71 (m, 2H), 7.63 (s, 1H), 6.59 (d, 1H), 4.07 (s, 3H), 3.49 (s, 4H), 1.98 (s, 4H) 3. 381.15 |
| 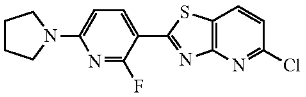 [SMILES: Fc1nc(N2CCCC2)ccc1-c1nc2nc(Cl)ccc2s1] | 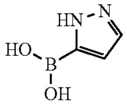 | 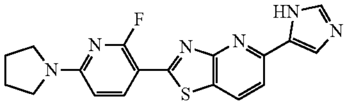 95 | 1. 51% 2. tautomers (~75/25), for the major: $^1$H NMR (400 MHz, DMSO-$d_6$) δ 13.11 (s, 1H), 8.59-8.42 (m, 2H), 8.01 (d, 1H), 7.87 (s, 1H), 6.95 (s, 1H), 6.74-6.50 (m, 1H), 3.48 (s, 4H), 1.98 (s, 4H)) 3. 367.05 |
| 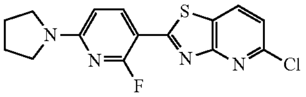 [SMILES: Fc1nc(N2CCCC2)ccc1-c1nc2nc(Cl)ccc2s1] | 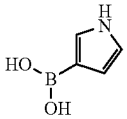 | 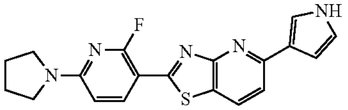 96 | 1. 47% 2. $^1$H NMR (400 MHz, DMSO-$d_6$) δ 11.13 (s, 1H), 8.62-8.44 (m, 1H), 8.39 (d, 1H), 7.65 (d, 1H), 7.56 (s, 1H), 6.94-6.79 (m, 1H), 6.79-6.68 (m, 1H), 6.61 (dd, 1H), 3.49 (s, 4H), 1.98 (s, 4H) 3. 366.11 |
| 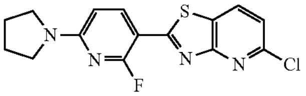 [SMILES: Fc1nc(N2CCCC2)ccc1-c1nc2nc(Cl)ccc2s1] | 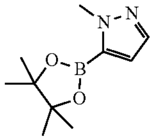 | 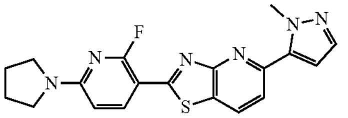 97 | 1. 70% 2. $^1$H NMR (400 MHz, DMSO-$d_6$) δ 8.63 (d, 1H), 8.52 (t, 1H), 7.81 (d, 1H), 7.53 (s, 1H), 6.91 (s, 1H), 6.60 (d, 1H), 4.27 (s, 3H), 3.49 (s, 4H), 1.98 (s, 4H) 3. 380.59 |
| 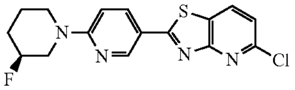 [SMILES: F[C@H]1CCCN(c2ccc(-c3nc4nc(Cl)ccc4s3)cn2)C1] | 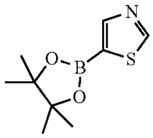 | 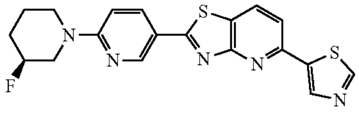 98 | 1. 17% 2. $^1$H NMR (400 MHz, Chloroform-d) δ 8.92 (d, J = 2.5 Hz, 1H), 8.89 (s, 1H), 8.49 (s, 1H), 8.35 (d, J = 8.8 Hz, 1H), 8.25 (d, J = 8.3 Hz, 1H), 7.72 (d, J = 8.3 Hz, 1H), 6.80 (d, J = 9.1 Hz, 1H), 4.80 (d, J = 47.5 Hz, 1H), 4.05 (d, J = 7.6 Hz, 1H), 3.95-3.80 (m, 1H), 3.62 (s, 1H), 2.02 (d, J = 16.8 Hz, 4H), 1.69 (s, 1H). 3. 398.07 |

TABLE 2-continued

| Chloro Starting Material | Boronic acid/ester | Product Example | 1. Yield 2. $^1$H-NMR 3. $MH^+$ (ESI) |
|---|---|---|---|
| 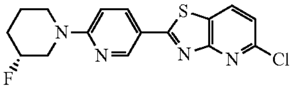 [SMILES: F[C@@H]1CCCN(c2ccc(-c3nc4nc(Cl)ccc4s3)cn2)C1] | 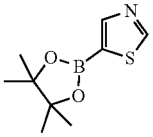 | 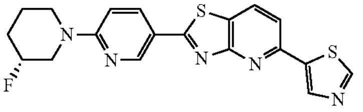 99 | 1. 9% 2. $^1$H NMR (400 MHz, Chloroform-d) δ 8.92 (s, 1H), 8.89 (s, 1H), 8.49 (s, 1H), 8.37-8.29 (m, 1H), 8.24 (d, J = 8.2 Hz, 1H), 7.71 (d, J = 8.2 Hz, 1H), 6.79 (d, J = 9.1 Hz, 1H), 4.79 (d, J = 47.4 Hz, 1H), 4.05 (dt, J = 14.4, 7.4 Hz, 1H), 3.96-3.80 (m, 2H), 3.62 (s, 1H), 1.64 (d, J = 36.1 Hz, 4H). 3. 397.56 |
| 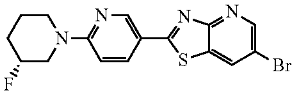 [SMILES: F[C@@H]1CCCN(c2ccc(-c3nc4ncc(Br)cc4s3)cn2)C1] | 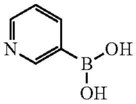 | 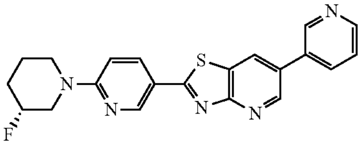 100 | 1. 30% 2. $^1$H NMR (500 MHz, DMSO-$d_6$) δ 9.05 (d, 1H), 9.02 (d, 1H), 8.97 (d, 1H), 8.88 (d, 1H), 8.65 (dd, 1H), 8.29-8.23 (m, 1H), 8.21 (dd, 1H), 7.56 (ddd, 1H), 7.07 (d, 1H), 4.98-4.71 (m, 1H), 4.24-4.09 (m, 1H), 4.09-3.96 (m, 1H), 3.82-3.69 (m, 1H), 3.50-3.45 (m, 1H), 2.03-1.84 (m, 2H), 1.84-1.70 (m, 1H), 1.64-1.51 (m, 1H) 3. 391.8 |
| 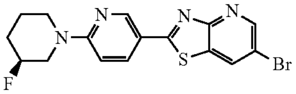 [SMILES: F[C@H]1CCCN(c2ccc(-c3nc4ncc(Br)cc4s3)cn2)C1] | 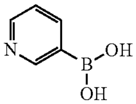 | 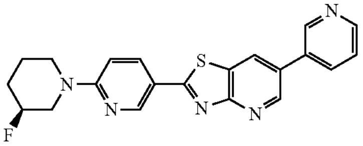 101 | 1. 30% 2. $^1$H NMR (500 MHz, DMSO-$d_6$) δ 9.06-9.03 (m, 1H), 9.02 (d, 1H), 8.97 (d, 1H), 8.88 (d, 1H), 8.65 (dd, 1H), 8.25 (ddd, 1H), 8.21 (dd, 1H), 7.56 (ddd, 1H), 7.07 (d, 1H), 4.92-4.74 (m, 1H), 4.25-4.12 (m, 1H), 4.06-3.95 (m, 1H), 3.76 (dd, 1H), 3.53-3.44 (m, 1H), 2.02-1.85 (m, 2H), 1.78 (s, 1H), 1.65-1.54 (m, 1H) 3. 391.9 |
| 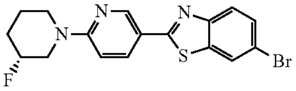 [SMILES: F[C@@H]1CCCN(c2ccc(-c3nc4ccc(Br)cc4s3)cn2)C1] | 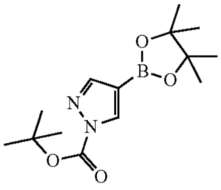 [SMILES: CC(C)(C)OC(=O)n1cc(B2OC(C)(C)C(C)(C)O2)cn1] | 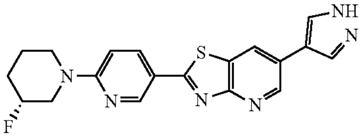 102 | 1. 26% 2. $^1$H NMR (400 MHz, DMSO-$d_6$) δ 12.99 (s, 1H), 8.76 (d, 1H), 8.41-8.18 (m, 2H), 8.17-7.97 (m, 2H), 7.93 (d, 1H), 7.76 (d, 1H), 7.02 (d, 1H), 4.81 (d, 1H), 4.17-4.01 (m, 1H), 4.00-3.87 (m, 1H), 3.83-3.67 (m, 1H), 3.50-3.40 (m, 1H), 2.07-1.67 (m, 3H), 1.58 (s, 1H) 3. 380.27 |

TABLE 2-continued

| Chloro Starting Material | Boronic acid/ester | Product Example | 1. Yield 2. $^1$H-NMR 3. MH$^+$ (ESI) |
|---|---|---|---|
| 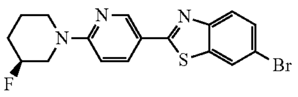 [SMILES: F[C@H]1CCCN(c2ccc(-c3nc4ccc(Br)cc4s3)cn2)C1] | 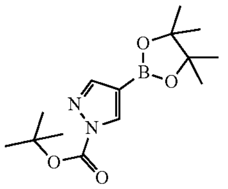 [SMILES: CC(C)(C)OC(=O)n1cc(B2OC(C)(C)C(C)(C)O2)cn1] | 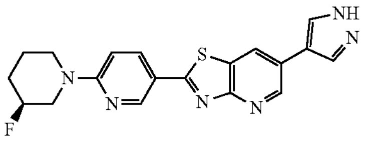 103 | 1. 10% 2. $^1$H NMR (400 MHz, DMSO-d$_6$) δ 13.01 (s, 1H), 8.89-8.71 (m, 1H), 8.42-8.22 (m, 2H), 8.20-8.08 (m, 1H), 8.04 (s, 1H), 7.94 (d, 1H), 7.77 (d, 1H), 7.04 (d, 1H), 4.83 (d, 1H), 4.19-4.03 (m, 1H), 3.95 (dd, 1H), 3.76 (dd, 1H), 3.51-3.43 (m, 1H), 2.08-1.86 (m, 2H), 1.86-1.70 (m, 1H), 1.68-1.51 (m, 1H) 3. 380.27 |
| 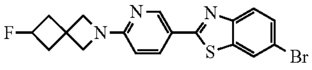 | 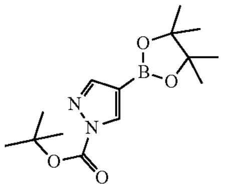 [SMILES: CC(C)(C)OC(=O)n1cc(B2OC(C)(C)C(C)(C)O2)cn1] | 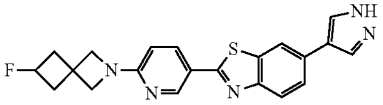 104 | 1. 35% 2. $^1$H NMR (400 MHz, DMSO-d$_6$) δ 12.99 (s, 1H), 8.92-8.66 (m, 1H), 8.29 (d, 2H), 8.11 (dd, 1H), 8.02 (s, 1H), 7.92 (d, 1H), 7.75 (d, 1H), 6.47 (d, 1H), 5.04 (dp, 1H), 4.07 (d, 4H), 2.76-2.60 (m, 2H), 2.41 (dtd, 2H) 3. 395.25 |

Example 26

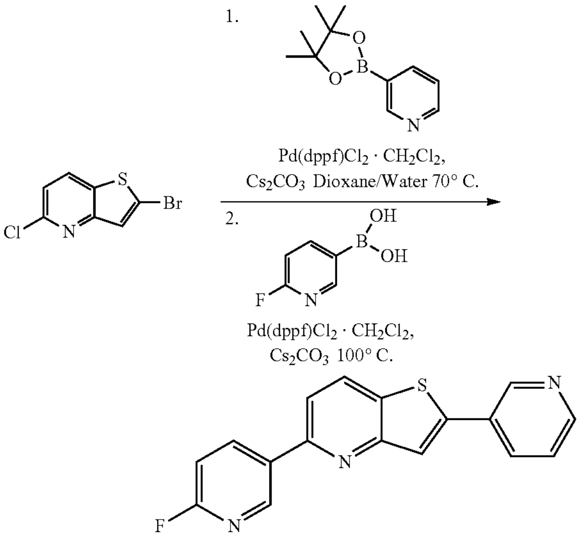

A mixture of 2-bromo-6-chlorothieno[2,3-b]pyridine from Preparative Example 1 (0.08 g, 0.32 mmol) 3-(4,4,5,5-tetramethyl-1,3,2-dioxaborolan-2-yl)pyridine (72.61 mg, 0.352 mmol), cesium carbonate (0.209 g, 0.64 mmol) and [1,1'-bis(diphenylphosphino)ferrocene]dichloropalladium (II) complex with dichloromethane (0.013 g, 0.016 mmol) were added into a dry pressure tube, followed by degassed dioxane (4 mL) and degassed water (1 mL). The reaction mixture was degassed with a stream of argon for 10 minutes and heated at 70° C. for 2 hours and cooled at room temperature. Cesium carbonate (0.209 g, 0.64 mmol), [1,1'-bis(diphenylphosphino)ferrocene]-dichloropalladium(II) complex with dichloromethane (0.013 g, 0.016 mmol) and (6-fluoropyridin-3-yl)boronic acid (0.059 g, 0.41 mmol) were added, followed by additional nitrogen purges. The reaction mixture was heated at 100° C. for 3 to 4 hours. Then the mixture was cooled at room temperature, taken up in ethyl acetate (20 mL), washed with water (2×20 mL) and brine (10 mL), dried over $Na_2SO_4$, and concentrated under reduced pressure. The residue was purified on HP-Sil SNAP cartridges using a Biotage Isolera One purification system employing ethyl acetate/n-heptane gradient (50/50→90/10) to afford the title compound (0.09 g, 91%).

$^1$H-NMR (400 MHz, Chloroform-d) δ 9.06 (s, 1H), 8.94-8.84 (m, 1H), 8.67 (d, 1H), 8.57 (td, 1H), 8.28 (d, 1H), 8.06 (d, 1H), 7.90 (s, 1H), 7.71 (d, 1H), 7.45 (dd, 1H), 7.10 (dd, 1H).

MS (ESI); m/z=308.37 [M+H]$^+$

Examples 27 to 43, 88 and 105 to 110

Following the one-pot Suzuki coupling reaction described in Example 26, using the bromo-chloro starting material, the $R^1$ boronic acid or ester and the $R^2$ boronic acid or ester indicated in the table below, the following compounds were prepared. The palladium source [1,1'-bis(diphenylphosphino)ferrocene]dichloropalladium(II) complex with dichloromethane can be replaced by tetrakis(triphenylphosphine)palladium(0). Cesium carbonate can be replaced by potassium carbonate.

TABLE 3

| Bromo chloro Starting Material | Boronic acid/ester $R^1$ | Boronic acid/ester $R^2$ | Product Example | 1. Yield 2. $^1$H-NMR 3. $MH^+$ (ESI) |
|---|---|---|---|---|
| 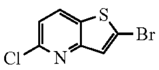 | 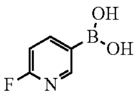 | 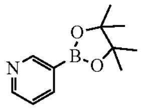 | 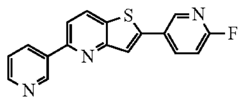 27 | 1. 20% 2 $^1$H-NMR (400 MHz, DMSO-$d_6$) δ 9.35 (d, 1H), 8.81 (d, 1H), 8.70-8.62 (m, 2H), 8.52 (ddd, 2H), 8.25 (s, 1H), 8.07 (d, 1H), 7.56 (dd, 1H), 7.38 (dd, 1H). 3. 308.37 |
| 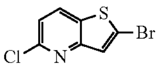 | 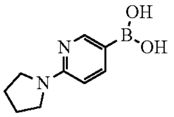 [SMILES: OB(O)c1ccc(N2CCCC2)nc1] | 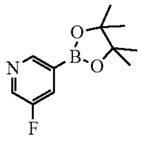 [SMILES: CC1(C)OB(c2cncc(F)c2)OC1(C)C] | 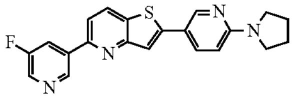 28 | 1. 5% 2 $^1$H-NMR (400 MHz, DMSO-$d_6$) δ 9.26 (t, 1H), 8.65 (dd, 2H), 8.55 (d, 1H), 8.41 (dt, 1H), 8.09-7.97 (m, 2H), 7.92 (s, 1H), 6.60 (d, 1H), 3.47 (m, 4H), 1.99 (m, 4H). 3. 377.63 |
| 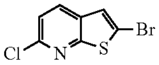 | 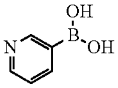 | 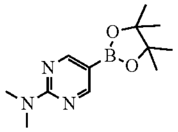 | 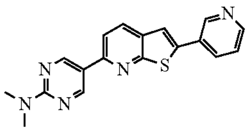 29 | 1. 32% 2. $^1$H-NMR (400 MHz, DMSO-$d_6$) δ 9.27 (s, 1H), 9.14 (s, 2H), 8.78 (d, 1H), 8.62 (d, 1H), 8.34 (d, 1H), 8.16 (s, 1H), 8.02 (d, 1H), 7.94-7.86 (m, 1H), 3.23 (s, 6H). 3. 334.12 |
| 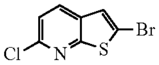 | 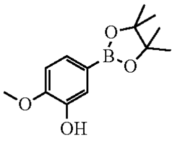 | 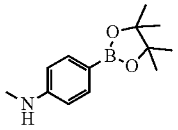 | 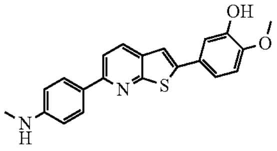 30 | 1. 32% 2. $^1$H-NMR (400 MHz, DMSO-$d_6$) δ 9.33 (s, 1H), 8.09 (d, 1H), 7.94 (d, 2H), 7.82 (d, 1H), 7.57 (s, 1H), 7.24-7.16 (m, 2H), 7.03 (d, 1H), 6.64 (d, 2H), 6.09 (q, 1H), 3.82 (s, 3H), 2.74 (d, 3H). 3. 362.90 |
| 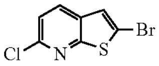 | 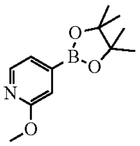 [SMILES: COc1cc(B2OC(C)(C)C(C)(C)O2)ccn1] | 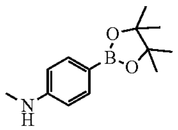 | 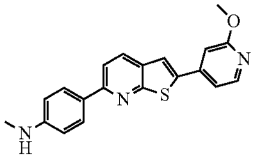 31 | 1. 18% 2. $^1$H-NMR (400 MHz, DMSO-$d_6$) δ 8.26 (d, 1H), 8.20 (d, 1H), 8.09 (s, 1H), 7.98 (d, 2H), 7.90 (d, 1H), 7.39 (dd, 1H), 7.16 (s, 1H), 6.65 (d, 2H), 6.18 (q, 1H), 3.91 (s, 3H), 2.75 (d, 3H). 3. 347.85 |

TABLE 3-continued

| Bromo chloro Starting Material | Boronic acid/ester $R^1$ | Boronic acid/ester $R^2$ | Product Example | 1. Yield 2. $^1$H-NMR 3. $MH^+$ (ESI) |
|---|---|---|---|---|
| 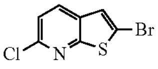 | 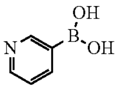 | 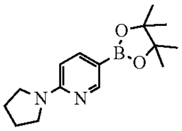 [SMILES: CC1(C)OB(c2ccc(N3CCCC3)nc2)OC1(C)C] | 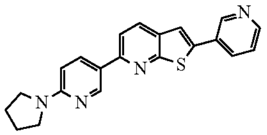 32 | 1. 48% 2. $^1$H-NMR (400 MHz, DMSO-$d_6$) δ 9.04 (s, 1H), 8.90 (s, 1H), 8.60 (d, 1H), 8.36-8.15 (m, 3H), 8.03-7.87 (m, 2H), 7.54 (dd, 1H), 6.58 (d, 1H), 3.47 (t, 4H), 2.09-1.88 (m, 4H). 3. 358.78 |
| 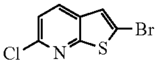 | 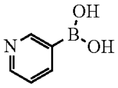 | 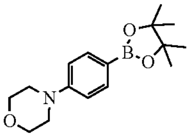 [SMILES: CC1(C)OB(c2ccc(N3CCOCC3)cc2)OC1(C)C] | 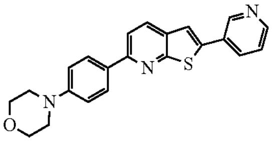 33 | 1. 47% 2. $^1$H-NMR (400 MHz, DMSO-$d_6$) δ 9.05 (s, 1H), 8.95 (s, 1H), 8.61 (d, 1H), 8.35 (d, 1H), 8.27 (d, 1H), 8.20 (d, 1H), 8.05-7.94 (m, 2H), 7.61-7.49 (m, 1H), 6.97 (d, J = 9.8 Hz, 1H), 3.80-3.65 (m, 4H), 3.65-3.51 (m, 4H). 3. 374.82 |
| 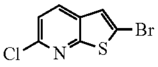 | 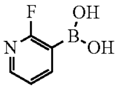 | 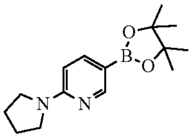 [SMILES: CC1(C)OB(c2ccc(N3CCCC3)nc2)OC1(C)C] | 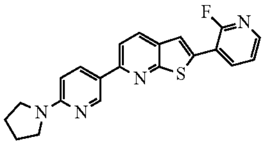 34 | 1. 21% 2. $^1$H-NMR (400 MHz, DMSO-$d_6$) δ 8.91 (d, 1H), 8.48-8.38 (m, 1H), 8.34-8.24 (m, 3H), 7.97 (t, 2H), 7.53 (ddd, 1H), 6.57 (d, 1H), 3.47 (t, 4H), 1.97 (t, 4H). 3. 377.0 |
| 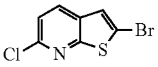 | 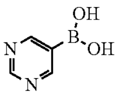 | 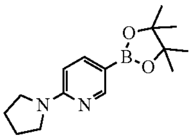 [SMILES: CC1(C)OB(c2ccc(N3CCCC3)nc2)OC1(C)C] | 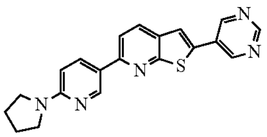 35 | 1. 74% 2. $^1$H-NMR (400 MHz, DMSO-$d_6$) δ 9.25 (s, 2H), 9.20 (s, 1H), 8.92 (s, 1H), 8.28 (t, J = 8.9 Hz, 2H), 8.08 (s, 1H), 7.97 (d, 1H), 6.57 (d, 1H), 3.57-3.42 (m, 4H), 2.05-1.89 (m, 4H). 3. 360.08 |
| 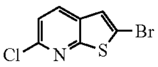 | 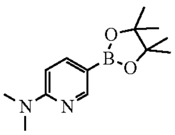 | 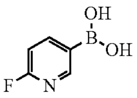 | 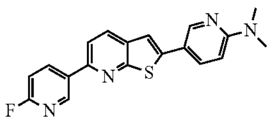 36 | 1. 44% 2. $^1$H-NMR (400 MHz, DMSO-$d_6$) δ 8.99 (s, 1H), 8.70 (t, 1H), 8.55 (s, 1H), 8.23 (d, 1H), 8.06 (d, 1H), 7.92 (d, 1H), 7.67 (s, 1H), 7.33 (d, 1H), 6.76 (d, 1H), 3.10 (s, 6H). 3. 351.08 |

TABLE 3-continued

| Bromo chloro Starting Material | Boronic acid/ester $R^1$ | Boronic acid/ester $R^2$ | Product Example | 1. Yield 2. $^1$H-NMR 3. $MH^+$ (ESI) |
|---|---|---|---|---|
| | | | 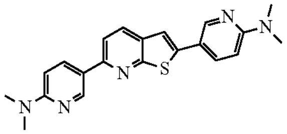 37 | 1. 28% 2. $^1$H-NMR (400 MHz, DMSO-$d_6$) δ 8.88 (s, 1H), 8.53 (s, 1H), 8.26 (dd, 1H), 8.11 (d, 1H), 7.95-7.83 (m, 2H), 7.61 (s, 1H), 6.76 (d, 2H), 3.11 (s, 6H), 3.10 (s, 6H). 3. 376.13 |
| 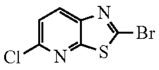 | 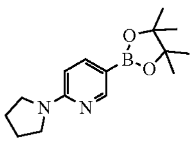 [SMILES: CC1(C)OB(c2ccc(N3CCCC3)nc2)OC1(C)C] | 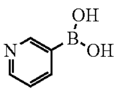 | 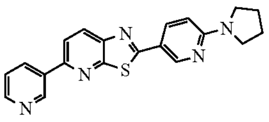 38 | 1. 13% 2. $^1$H-NMR (400 MHz, DMSO-$d_6$) δ 9.33 (s, 1H), 8.80 (s, 1H), 8.71-8.61 (m, 1H), 8.50 (d, 1H), 8.38 (d, 1H), 8.16 (dd, 2H), 7.62-7.47 (m, 1H), 6.62 (d, 1H), 3.49 (s, 4H), 1.98 (s, 4H). 3. 360.12 |
| 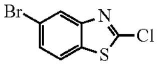 | 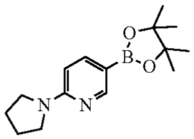 [SMILES: CC1(C)OB(c2ccc(N3CCCC3)nc2)OC1(C)C] | 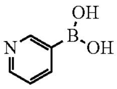 | 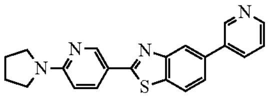 39 | 1. 30% 2. $^1$H-NMR (400 MHz, DMSO-$d_6$) δ 9.02 (d, 1H), 8.80 (d, 1H), 8.68-8.55 (m, 1H), 8.31 (d, 1H), 8.24-8.15 (m, 2H), 8.13 (dd, 1H), 7.75 (dd, 1H), 7.52 (dd, 1H), 6.61 (d, 1H), 3.58-3.42 (m, 4H), 2.06-1.91 (m, 4H). 3. 359.06 |
| 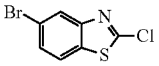 | 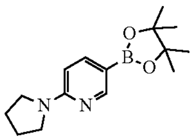 [SMILES: CC1(C)OB(c2ccc(N3CCCC3)nc2)OC1(C)C] | 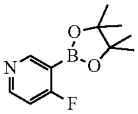 [SMILES: CC1(C)OB(c2cnccc2F)OC1(C)C] | 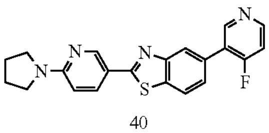 [SMILES: Fc1ccncc1-c1ccc2sc(-c3ccc(N4CCCC4)nc3)nc2c1] 40 | 1. 18% 2. $^1$H-NMR (400 MHz, DMSO-$d_6$) δ 8.86 (d, 1H), 8.80 (d, 1H), 8.72-8.56 (m, 1H), 8.21 (d, 1H), 8.18 (s, 1H), 8.17-8.09 (m, 1H), 7.61 (d, 1H), 7.50 (dd, 1H), 6.62 (d, 1H), 3.50 (s, 4H), 1.98 (s, 4H). 3. 377.29 |
| 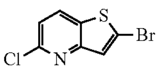 | 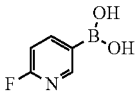 | 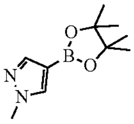 | 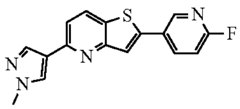 41 | 1. 77% 2. $^1$H NMR (400 MHz, Chloroform-d) δ 8.62 (dt, 1H), 8.16-8.11 (m, 2H), 8.06-8.02 (m, 2H), 7.75 (s, 1H), 7.48 (d, 1H), 7.08 (ddd, 1H), 4.01 (s, 3H). 3. 310.11 |

TABLE 3-continued

| Bromo chloro Starting Material | Boronic acid/ester $R^1$ | Boronic acid/ester $R^2$ | Product Example | 1. Yield 2. $^1$H-NMR 3. $MH^+$ (ESI) |
|---|---|---|---|---|
| 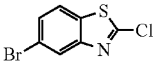 [SMILES: Clc1nc2cc(Br)ccc2s1] | 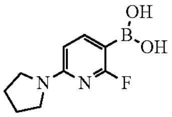 [SMILES: OB(O)c1ccc(N2CCCC2)nc1F] | 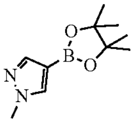 | 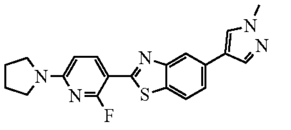 42 | 1. 58% 2. $^1$H NMR (400 MHz, DMSO-$d_6$) δ 8.51-8.36 (m, 1H), 8.26 (s, 1H), 8.18 (s, 1H), 8.03 (d, 1H), 7.99 (s, 1H), 7.61 (dd, 1H), 6.57 (dd, 1H), 3.89 (s, 3H), 3.47 (s, 4H), 1.97 (s, 4H). 3. 380.00 |
| 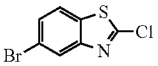 | 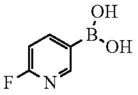 | 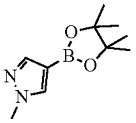 | 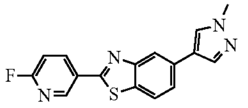 43 | 1. 50% 2. $^1$H NMR (400 MHz, DMSO-$d_6$) δ 9.07-8.85 (m, 1H), 8.66 (d, 1H), 8.30 (d, 2H), 8.16 (d, 1H), 8.03 (s, 1H), 7.73 (d, 1H), 7.55-7.31 (m, 1H), 3.89 (s, 3H). 3. 311.05 |
| 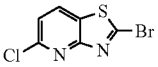 | 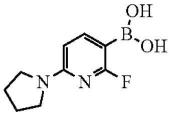 [SMILES: OB(O)c1ccc(N2CCCC2)nc1F] | 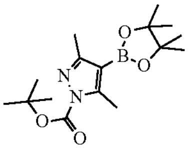 [SMILES: Cc1nn(C(=O)OC(C)(C)C)c(C)c1B1OC(C)(C)C(C)(C)O1] | 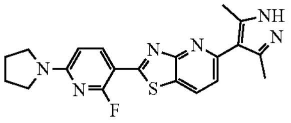 88 | 1. 23% 2. $^1$H NMR (400 MHz, DMSO-$d_6$) δ 12.45 (s, 1H), 8.64-8.43 (m, 2H), 7.43 (d, 1H), 6.60 (dd, 1H), 3.49 (s, 4H), 2.45 (s, 3H), 2.39 (s, 3H), 1.99 (s, 4H) 3. 395.20 |
| 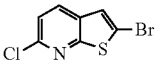 | 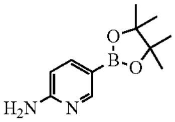 [SMILES: CC1(C)OB(c2ccc(N)nc2)OC1(C)C] | 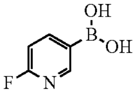 | 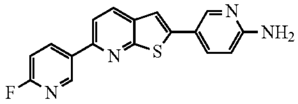 105 | 1. 24% 2. $^1$H NMR (400 MHz, DMSO-$d_6$) δ 9.01 (d, 1H), 8.72 (td, 1H), 8.40 (d, 1H), 8.25 (d, 1H), 8.08 (d, 1H), 7.84 (dd, 1H), 7.65 (s, 1H), 7.35 (dd, 1H), 6.58 (d, 1H), 6.47 (s, 2H). 3. 322.82 |
| 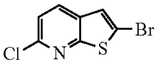 | 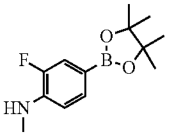 [SMILES: CNc1ccc(B2OC(C)(C)C(C)(C)O2)cc1F] | 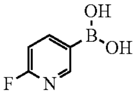 | 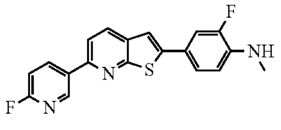 106 | 1. 64% 2. $^1$H NMR (400 MHz, DMSO-$d_6$) 9.00 (d, 1H), 8.72 (td, 1H), 8.24 (d, 1H), 8.08 (d, 1H), 7.68 (s, 1H), 7.57 (dd, 1H), 7.47 (dd, 1H), 7.35 (dd, 1H), 6.76 (t, 1H), 6.09 (dd, 1H), 2.80 (d, 3H). 3. 353.80 |

TABLE 3-continued

| Bromo chloro Starting Material | Boronic acid/ester $R^1$ | Boronic acid/ester $R^2$ | Product Example | 1. Yield 2. $^1$H-NMR 3. $MH^+$ (ESI) |
|---|---|---|---|---|
| 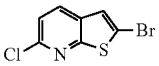 | 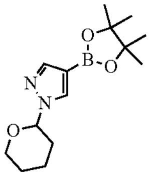 [SMILES: CC1(C)OB(c2cnn(C3CCCCO3)c2)OC1(C)C] | 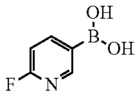 | 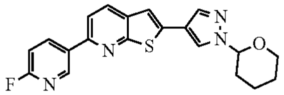 107 | 1. 61% 2. $^1$H NMR (400 MHz, Chloroform-d) δ 8.85 (dt, 1H), 8.52 (ddd, 1H), 7.99 (d, 1H), 7.93 (d, 1H), 7.87 (d, 1H), 7.66 (d, 1H), 7.21 (s, 1H), 7.03 (ddd, 1H), 5.47-5.35 (m, 1H), 4.18-4.06 (m, 1H), 3.74 (ddt, 1H), 2.22-1.96 (m, 3H), 1.78-1.57 (m, 3H). 3. 380.81 |
| 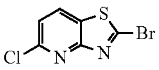 | 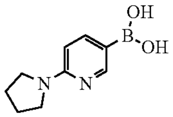 [SMILES: OB(O)c1ccc(N2CCCC2)nc1] | 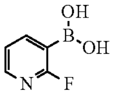 | 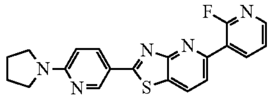 108 | 1. 5% 2. $^1$H NMR (400 MHz, Chloroform-d) δ 8.91 (d, 1H), 8.82 (ddd, 1H), 8.33-8.23 (m, 3H), 7.92 (dd, 1H), 7.37 (ddd, 1H), 6.49 (d, 1H), 3.59 (s, 4H), 2.07 (t, 4H). 3. 378.13 |
| 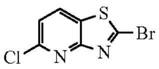 | 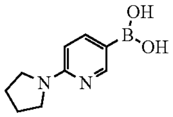 | 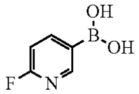 | 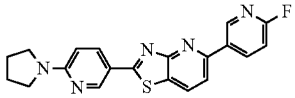 109 | 1. 43% 2. $^1$H NMR (400 MHz, DMSO-$d_6$) δ 9.02 (s, 1H), 8.87 (s, 1H), 8.74 (s, 1H), 8.70-8.60 (m, 1H), 8.18 (d, 1H), 8.05 (d, 1H), 7.42-7.28 (m, 1H), 6.72-6.60 (m, 1H), 3.51 (s, 4H), 1.99 (s, 4H). 3. 378.10 |
| 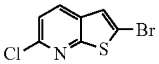 | 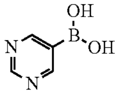 | 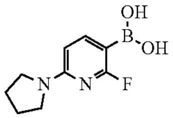 [SMILES: OB(O)c1ccc(N2CCCC2)nc1F] | 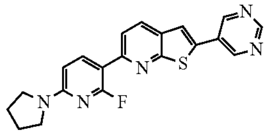 110 | 1. 39% 2. $^1$H NMR (400 MHz, DMSO-$d_6$) δ 9.26 (s, 2H), 9.21 (s, 1H), 8.38 (dd, 1H), 8.30 (d, 1H), 8.11 (s, 1H), 7.83 (d, 1H), 6.57-6.50 (m, 1H), 3.54-3.42 (m, 4H), 2.04-1.93 (m, 4H) 3. 378.21 |

-continued

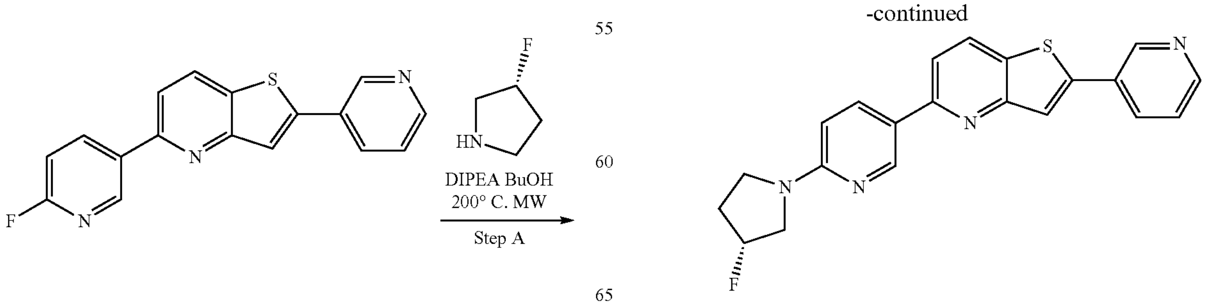

Example 44

Step A:

To a microwave tube were added the title compound from Example 26 (0.03 g, 0.0976 mmol), (R)-3-fluoropyrrolidine (0.061 g, 0.488 mmol), n-butanol (3 mL), followed by N,N'-diisopropylethylamine (0.118 mL, 0.683 mmol). The tube was sealed and heated at 200° C. for 1 hour using a Biotage Initiator microwave. The solvent was removed under reduced pressure and the residue was taken up in dichlorometane (20 mL), washed with ammonium chloride saturated solution (20 ml) and water (20 ml), dried over $Na_2SO_4$, and concentrated under reduced pressure.

The residue was purified on HP-Sil SNAP cartridges using a Biotage Isolera One purification system employing a methanol/dichloromethane gradient (0/100→10/90) to afford the title compound (0.013 g, 35%).

$^1$H-NMR (400 MHz, Chloroform-d) δ 9.05 (d, 1H), 8.87 (d, 1H), 8.64 (dd, 1H), 8.32 (dd, 1H), 8.17 (d, 1H), 8.03 (dt, 1H), 7.86 (s, 1H), 7.65 (d, 1H), 7.42 (dd, 1H), 6.55 (d, 1H), 5.43 (d, 1H), 3.96 (dd, 1H), 3.87-3.60 (m, 3H), 2.57-2.36 (m, 1H), 2.35-1.99 (m, 1H).

MS (ESI); m/z=377.48 $[M+H]^+$

Examples 45 to 55, 89 to 93 and 111 to 122

Following the procedure described in Example 44, except using the fluoro derivatives and amines indicated in the table below, the following compounds were prepared.

TABLE 4
| Fluoro Derivative | Amine | Product Example | 1. Yield<br>2. $^1$H-NMR<br>3. $MH^+$ ESI) |
|---|---|---|---|
| 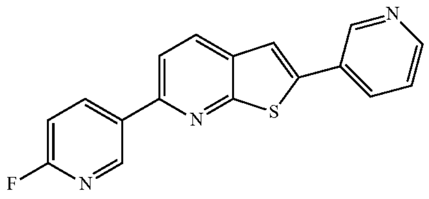 [SMILES: Fc1ccc(-c2ccc3cc(-c4cccnc4)sc3n2)cn1] | 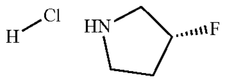 | 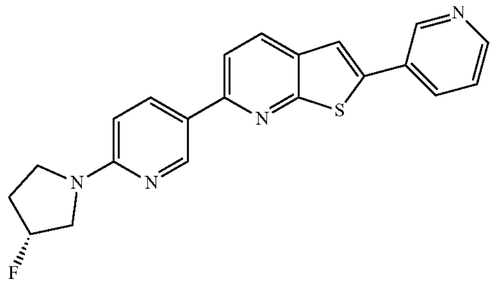<br>45 | 1. 44%<br>2. $^1$H-NMR (400 MHz, DMSO-$d_6$) δ 9.04 (s, 1H), 8.99-8.88 (m, 1H), 8.60 (d, 1H), 8.37-8.29 (m, 1H), 8.24 (d, 1H), 8.19 (d, 1H), 7.97 (t, 2H), 7.54 (dd, 1H), 6.65 (d, 1H), 5.48 (d, 1H), 3.90-3.60 (m, 3H), 3.51 (p, 1H), 2.39-2.09 (m, 2H).<br>3. 377.0 |
| 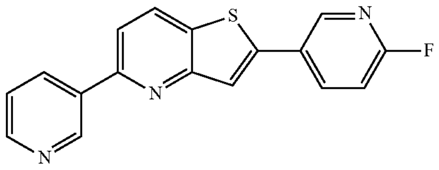 [SMILES: Fc1ccc(-c2cc3nc(-c4cccnc4)ccc3s2)cn1] | 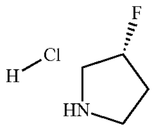 | 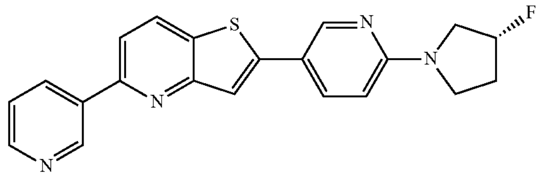<br>46 | 1. 57%<br>2. $^1$H-NMR (400 MHz, DMSO-$d_6$) δ 9.33 (d, 1H), 8.65 (dd, 2H), 8.57-8.42 (m, 2H), 8.03 (dd, 1H), 7.99-7.90 (m, 2H), 7.55 (dd, 1H), 6.65 (d, 1H), 5.61-5.32 (m, 1H), 3.90-3.56 (m, 3H), 3.49 (td, 1H), 2.38-2.05 (m, 2H).<br>3. 377.47 |
| 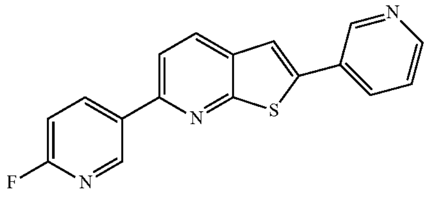 [SMILES: Fc1ccc(-c2ccc3cc(-c4cccnc4)sc3n2)cn1] | $CH_3NH_2$ | 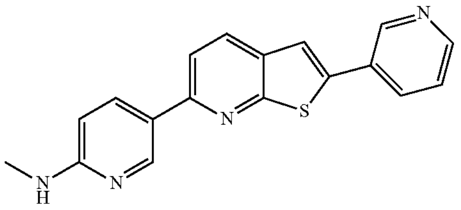<br>47 | 1. 94%<br>2. $^1$H-NMR (400 MHz, DMSO-$d_6$) δ 9.04 (d, 1H), 8.83 (d, 1H), 8.60 (d, 1H), 8.26-8.15 (m, 3H), 7.97 (s, 1H), 7.93 (d, 1H), 7.53 (dd, 1H), 6.94 (q, 1H), 6.57 (d, 1H), 2.85 (d3H).<br>3. 318.79 |

TABLE 4-continued
| Fluoro Derivative | Amine | Product Example | 1. Yield<br>2. $^1$H-NMR<br>3. $MH^+$ ESI) |
|---|---|---|---|
| 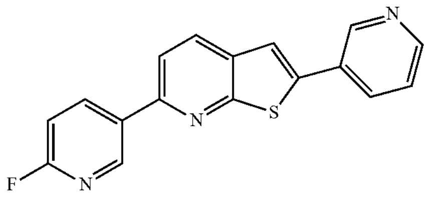 [SMILES: Fc1ccc(-c2ccc3cc(-c4cccnc4)sc3n2)cn1] | 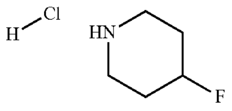 | 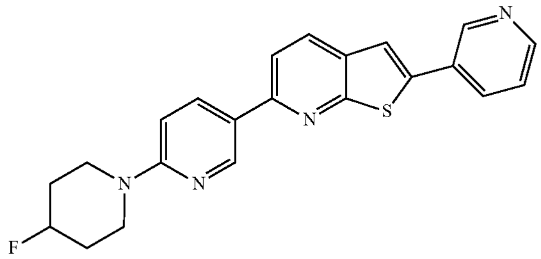<br>48 | 1. 53%<br>2. $^1$H-NMR (400 MHz, DMSO-$d_6$) δ 9.05 (d, 1H), 8.93 (d, 1H), 8.60 (dd, 1H), 8.32 (dd, 1H), 8.26 (d, 1H), 8.23-8.17 (m, 1H), 7.98 (t, 2H), 7.54 (dd, 1H), 7.02 (d, 1H), 4.93 (ddt, 1H), 3.84 (dd, 2H), 3.61 (ddd, 2H), 1.95 (dddd, 2H), 1.73 (ddt, 2H).<br>3. 391.2 |
| 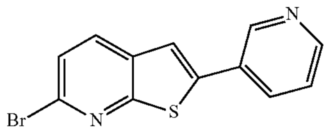 | 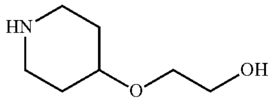 | 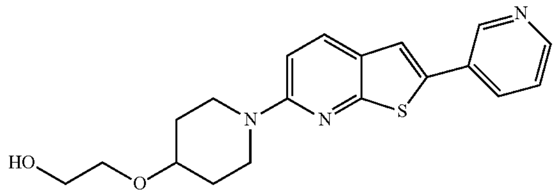<br>49 | 1. 15%<br>2. $^1$H-NMR (400 MHz, DMSO-$d_6$) δ 8.95-8.88 (m, 1H), 8.55-8.47 (m, 1H), 8.05 (dt, 1H), 7.93 (d, 1H), 7.74 (s, 1H), 7.46 (dd, 1H), 7.01 (d, 1H), 4.57 (t, 1H), 4.16-3.95 (m, 2H), 3.58 (dq, 1H), 3.53-3.47 (m, 4H), 3.29-3.20 (m, 2H), 1.98-1.85 (m, 2H), 1.53-1.38 (m, 2H).<br>3. 356.04 |
| 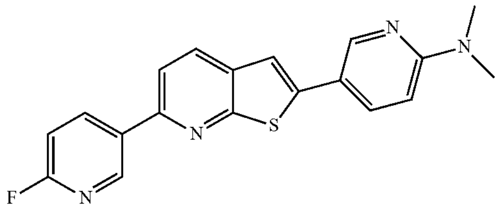 [SMILES: CN(C)c1ccc(-c2cc3ccc(-c4ccc(F)nc4)nc3s2)cn1] | 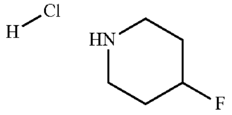 | 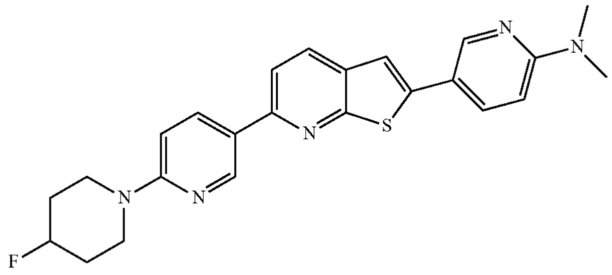<br>50 | 1. 74%<br>2. $^1$H-NMR (400 MHz, DMSO-$d_6$) δ 8.95-8.82 (m, 1H), 8.58-8.48 (m, 1H), 8.33-8.21 (m, 1H), 8.13 (d, 1H), 7.91 (dd, 2H), 7.62 (s, 1H), 7.01 (d, 1H), 6.76 (d, 1H), 5.06-4.75 (m, 1H), 3.92-3.76 (m, 2H), 3.69-3.49 (m, 2H), 3.10 (s, 6H), 2.08-1.84 (m, 2H), 1.83-1.61 (m, 2H).<br>3. 434.12 |

TABLE 4-continued
| Fluoro Derivative | Amine | Product Example | 1. Yield<br>2. $^1$H-NMR<br>3. MH$^+$ ESI) |
|---|---|---|---|
| 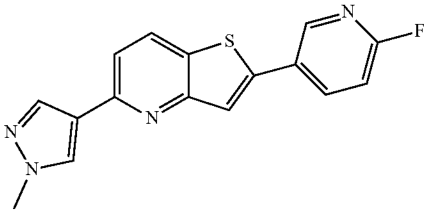 [SMILES: Cn1cc(-c2ccc3sc(-c4ccc(F)nc4)cc3n2)cn1] | 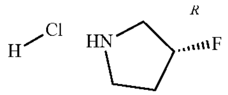 | 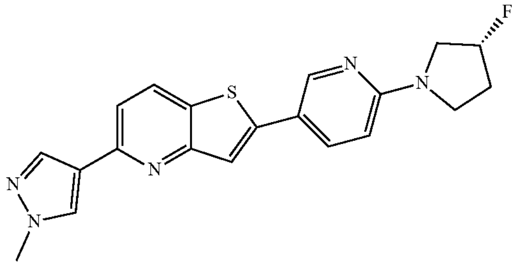<br>51 | 1. 75%<br>2. $^1$H NMR (400 MHz, Chloroform-d) δ 8.59 (dd, 1H), 8.09-7.94 (m, 3H), 7.78 (dd, 1H), 7.56 (d, 1H), 7.36 (d, 1H), 6.45 (dd, 1H), 5.56-5.31 (m, 1H), 3.98 (s, 3H), 3.95-3.84 (m, 1H), 3.81-3.56 (m, 3H), 2.50- 2.35 (m, 1H), 2.29-2.00 (m, 1H).<br>3. 380.05 |
| 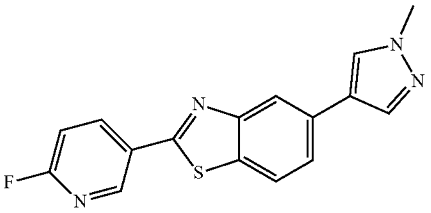 [SMILES: Cn1cc(-c2ccc3sc(-c4ccc(F)nc4)nc3c2)cn1] | 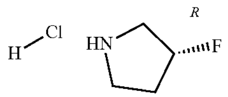 | 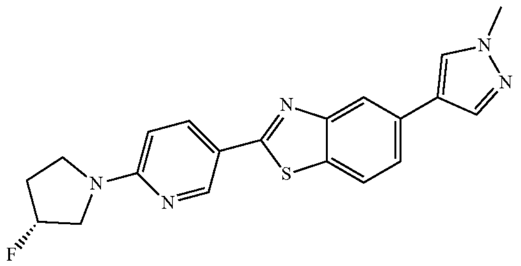<br>52 | 1. 98%<br>2. $^1$H NMR (400 MHz, DMSO-$d_6$) δ 8.79 (d, 1H), 8.26 (s, 1H), 8.22-8.08 (m, 2H), 8.08-7.95 (m, 2H), 7.61 (dd, 1H), 6.67 (d, 1H), 5.62-5.33 (m, 1H), 3.95-3.59 (m, 6H), 3.52 (td, 1H), 2.38-2.10 (m, 2H)<br>3. 380.03 |
| 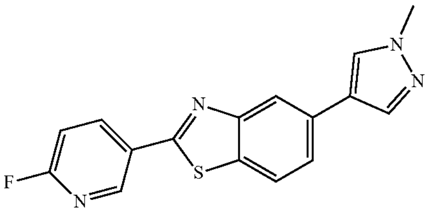 [SMILES: Cn1cc(-c2ccc3sc(-c4ccc(F)nc4)nc3c2)cn1] | 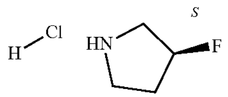 | 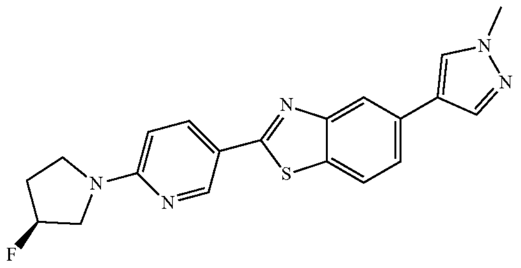<br>53 | 1. 64%<br>2. $^1$H NMR (400 MHz, DMSO-$d_6$) δ 8.80 (d, 1H), 8.27 (s, 1H), 8.22-8.11 (m, 2H), 8.10-7.93 (m, 2H), 7.62 (dd, 1H), 6.68 (d, 1H), 5.49 (d, 1H), 4.00-3.60 (m, 6H), 3.53 (td, 1H), 2.42-2.11 (m, 2H).<br>3. 380.02 |

TABLE 4-continued
| Fluoro Derivative | Amine | Product Example | 1. Yield 2. $^1$H-NMR 3. MH$^+$ ESI) |
|---|---|---|---|
| 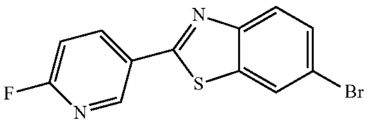 [SMILES: Fc1ccc(-c2nc3ccc(Br)cc3s2)cn1] | 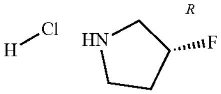 | 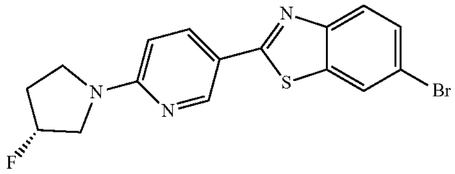 54 | 1. 94% $^1$H NMR (400 MHz, DMSO-$d_6$) δ 8.79 (s, 1H), 8.37 (s, 1H), 8.15 (d, 1H), 7.89 (d, 1H), 7.63 (d, 1H), 6.67 (d, 1H), 5.48 (d, 1H), 3.95-3.44 (m, 4H), 2.37-2.10 (m, 2H) 3. N/A |
| 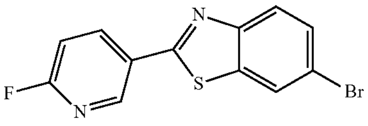 | 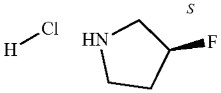 | 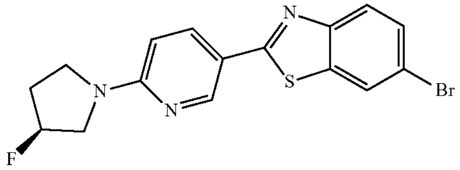 55 | 1. 95% $^1$H NMR (400 MHz, DMSO-$d_6$) δ 8.80 (d, 1H), 8.38 (s, 1H), 8.15 (dd, 1H), 7.89 (d, 1H), 7.64 (d, 1H), 6.68 (d, 1H), 5.48 (d, 1H), 3.94-3.46 (m, 4H), 2.38-2.11 (m, 2H) 3. N/A |
| 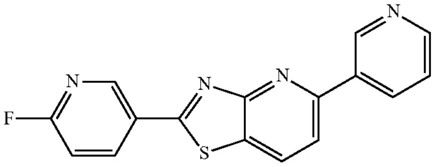 [SMILES: Fc1ccc(-c2nc3nc(-c4cccnc4)ccc3s2)cn1] | 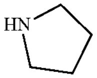 | 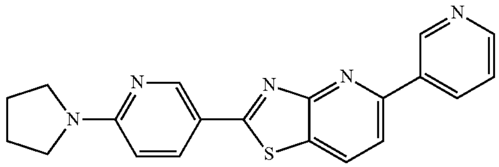 89 | 1. 78% $^1$H NMR (400 MHz, DMSO-$d_6$) δ 9.37 (s, 1H), 8.89 (s, 1H), 8.71-8.63 (m, 2H), 8.55 (d, 1H), 8.20 (d, 1H), 8.08 (d, 1H), 7.57 (dd, 1H), 6.66 (d, 1H), 3.52 (s, 4H), 1.99 (s, 5H) 3. 360.04 |
| 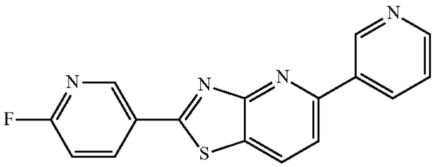 [SMILES: Fc1ccc(-c2nc3nc(-c4cccnc4)ccc3s2)cn1] | 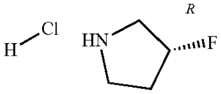 | 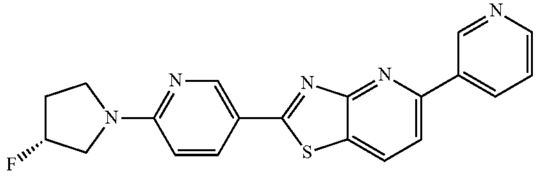 90 | 1. 61% $^1$H NMR (400 MHz, DMSO-$d_6$) δ 9.37 (s, 1H), 8.91 (d, 1H), 8.77-8.63 (m, 2H), 8.55 (d, 1H), 8.24 (dd, 1H), 8.09 (d, 1H), 7.57 (dd, 1H), 6.72 (d, 1H), 5.50 (d, 1H), 3.97-3.62 (m, 3H), 3.55 (q, 1H), 2.40-2.12 (m, 2H) 3. 378.06 |

TABLE 4-continued
| Fluoro Derivative | Amine | Product Example | 1. Yield<br>2. $^1$H-NMR<br>3. MH$^+$ ESI) |
|---|---|---|---|
| 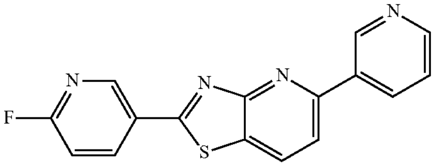 [SMILES: Fc1ccc(-c2nc3nc(-c4cccnc4)ccc3s2)cn1] | 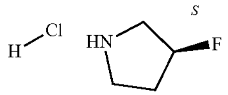 | 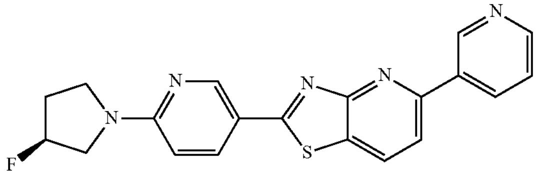<br>91 | 1. 75%<br>$^1$H NMR (400 MHz, DMSO-$d_6$) δ 9.37 (s, 1H), 8.91 (s, 1H), 8.68 (d, 2H), 8.55 (d, 1H), 8.24 (d, 1H), 8.09 (d, 1H), 7.57 (dd, 1H), 6.82-6.62 (m, 1H), 5.50 (d, 1H), 4.02-3.63 (m, 3H), 3.54 (q, 1H), 2.40-2.11 (m, 2H)<br>3. 378.05 |
| 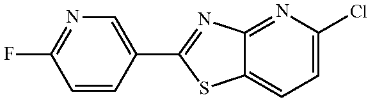 | 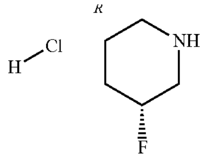 | 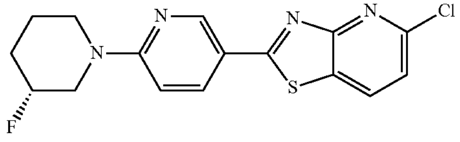<br>92 | 1. 57%<br>$^1$H NMR (400 MHz, DMSO-$d_6$) δ 8.86 (d, 1H), 8.63 (d, 1H), 8.17 (dd, 1H), 7.52 (d, 1H), 7.07 (d, 1H), 5.00-4.70 (m, 1H), 4.19 (ddd, 1H), 4.03 (dt, 1H), 3.76 (ddd, 1H), 3.51-3.42 (m, 1H), 2.07-1.87 (m, 2H), 1.87-1.70 (m, 1H), 1.70-1.50 (m, 1H)<br>3. 349.05 |
| 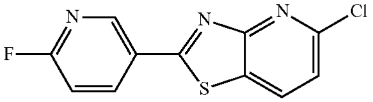 [SMILES: Fc1ccc(-c2nc3nc(Cl)ccc3s2)cn1] | 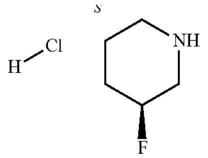 | 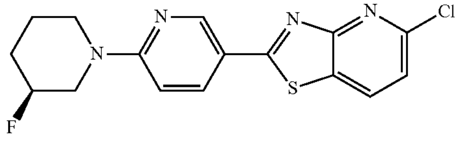<br>93 | 1. 66%<br>$^1$H NMR (400 MHz, DMSO-$d_6$) δ 8.84 (d, 1H), 8.62 (d, 1H), 8.16 (dd, 1H), 7.51 (d, 1H), 7.06 (d, 1H), 4.93-4.71 (m, 1H), 4.17 (ddd, 1H), 4.01 (dt, 1H), 3.74 (ddd, 1H), 3.45 (t, 1H), 2.04-1.85 (m, 2H), 1.85-1.70 (m, 1H), 1.65-1.53 (m, 1H)<br>3. 349.23 |

TABLE 4-continued
| Fluoro Derivative | Amine | Product Example | 1. Yield<br>2. $^{1}$H-NMR<br>3. $MH^+$ ESI) |
|---|---|---|---|
| 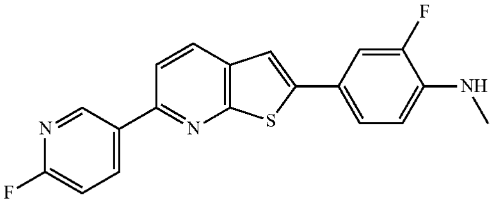 | 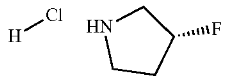 | 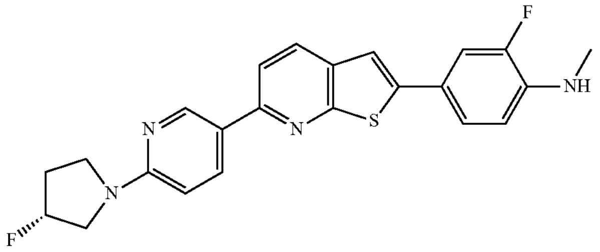<br>111 | 1. 2.5%<br>2. $^{1}$H NMR (400 MHz, DMSO-$d_6$) δ 8.91 (d, 1H), 8.31 (dd, 1H), 8.11 (d, 1H), 7.90 (d, 1H), 7.61 (s, 1H), 7.54 (dd, 1H), 7.44 (dd, 1H), 6.76 (t, 1H), 6.65 (d, 1H), 6.02 (d, 1H), 5.49 (d, 1H), 3.91-3.59 (m, 3H), 3.56-3.43 (m, 1H), 2.80 (d, 3H), 2.36-2.25 (m, 2H).<br>3. 422.73 |
| 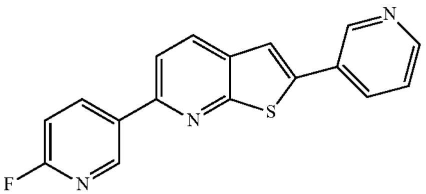 [SMILES: Fc1ccc(-c2ccc3cc(-c4cccnc4)sc3n2)cn1] | 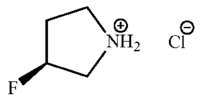 | 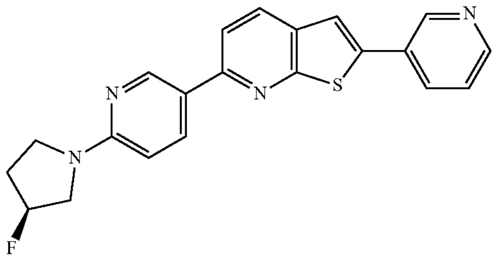<br>112 | 1. 38%<br>2. $^{1}$H NMR (400 MHz, DMSO-$d_6$) δ 9.05 (dd, 1H), 8.94 (d, 1H), 8.61 (dd, 1H), 8.34 (dd, 1H), 8.26 (d, 1H), 8.21 (ddd, 1H), 8.02-7.96 (m, 2H), 7.55 (ddd, 1H), 6.66 (d, 1H), 5.49 (d, 1H), 3.91-3.57 (m, 3H), 3.51 (td, 1H), 2.37-2.14 (m, 2H).<br>3. 376.57 |
| 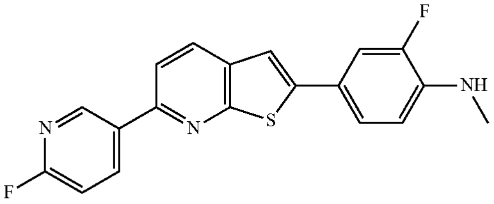 [SMILES: CNc1ccc(-c2cc3ccc(-c4ccc(F)nc4)nc3s2)cc1F] | 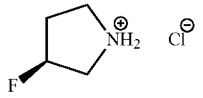 | 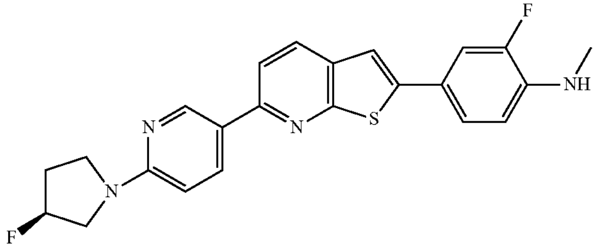<br>113 | 1. 22%<br>2. $^{1}$H NMR (400 MHz, DMSO-$d_6$) δ 8.90 (d, 1H), 8.30 (dd, 1H), 8.10 (d, 1H), 7.89 (d, 1H), 7.60 (s, 1H), 7.53 (dd, 1H), 7.43 (dd, 1H), 6.75 (t, 1H), 6.64 (d, 1H), 6.02 (dd, 1H), 5.49 (d, 1H), 3.90-3.58 (m, 3H), 3.51 (td, 1H), 2.79 (d, 3H), 2.36-2.15 (m, 2H).<br>3. 422.63 |

TABLE 4-continued
| Fluoro Derivative | Amine | Product Example | 1. Yield<br>2. $^1$H-NMR<br>3. MH$^+$ ESI) |
|---|---|---|---|
| 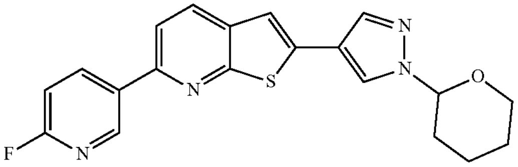 [SMILES: Fc1ccc(-c2ccc3cc(-c4cnn(C5CCCCO5)c4)sc3n2)cn1] | 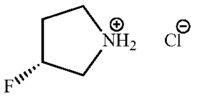 | 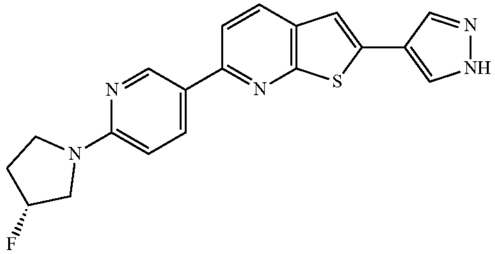<br>114 | 1. 6%<br>2. $^1$H NMR (400 MHz, DMSO-$d_6$) δ 13.22 (s, 1H), 8.91 (d, 1H), 8.30 (m, 2H), 8.13 (d, 1H), 7.97 (s, 1H), 7.90 (d, 1H), 7.49 (s, 1H), 6.65 (d, 1H), 5.49 (d, 1H), 3.97-3.58 (m, 3H), 3.51 (td, 1H), 2.39-2.08 (m, 2H).<br>3. 365.81 |
| 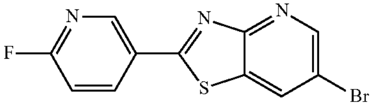 [SMILES: Fc1ccc(-c2nc3ncc(Br)cc3s2)cn1] | 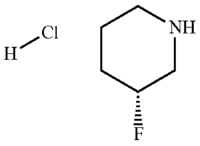 | 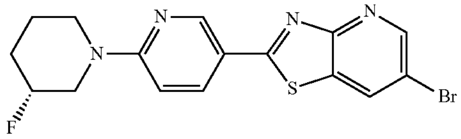<br>115 | 1. 55%<br>2. $^1$H NMR (500 MHz, DMSO-$d_6$) δ 8.88 (d, 1H), 8.84 (d, 1H), 8.71 (d, 1H), 8.17 (dd, 1H), 7.05 (d, 1H), 4.90-4.73 (m, 1H), 4.17 (ddd, 1H), 4.05-3.97 (m, 1H), 3.74 (ddd, 1H), 3.49-3.41 (m, 1H), 2.03-1.84 (m, 2H), 1.83-1.71 (m, 1H), 1.63-1.52 (m, 1H)<br>3. 393.56 |
| 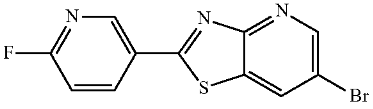 [SMILES: Fc1ccc(-c2nc3ncc(Br)cc3s2)cn1] | 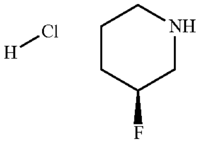 | 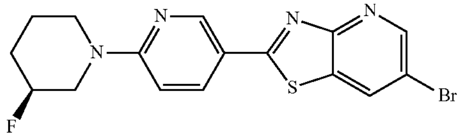<br>116 | 1. 53%<br>2. $^1$H NMR (500 MHz, DMSO-$d_6$) δ 8.88 (d, 1H), 8.84 (d, 1H), 8.71 (d, 1H), 8.17 (dd, 1H), 7.05 (d, 1H), 4.92-4.72 (m, 1H), 4.24-4.12 (m, 1H), 4.05-3.97 (m, 1H), 3.81-3.67 (m, 1H), 3.49-3.40 (m, 1H), 2.02-1.85 (m, 2H), 1.83-1.70 (m, 1H), 1.63-1.51 (m, 1H)<br>3. 393.63 |

TABLE 4-continued
| Fluoro Derivative | Amine | Product Example | 1. Yield<br>2. $^1$H-NMR<br>3. MH$^+$ ESI) |
|---|---|---|---|
| 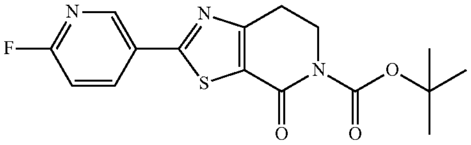 [SMILES: CC(C)(C)OC(=O)N1CCc2nc(-c3ccc(F)nc3)sc2C1=O] | 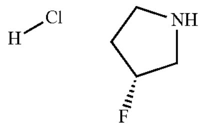 | 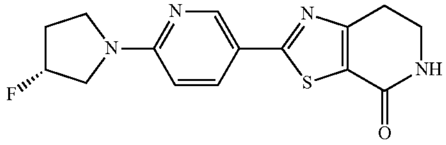<br>117 | 1. 74%<br>2. $^1$H NMR (500 MHz, DMSO-$d_6$) δ 8.78-8.70 (m, 1H), 8.05 (dd, 1H), 7.80 (s, 1H), 6.63 (d, 1H), 5.55-5.39 (m, 1H), 3.88-3.60 (m, 3H), 3.53-3.46 (m, 3H), 2.98 (t, 2H), 2.35-2.06 (m, 2H).<br>3. 319.10 |
| 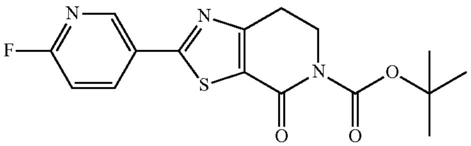 [SMILES: CC(C)(C)OC(=O)N1CCc2nc(-c3ccc(F)nc3)sc2C1=O] | 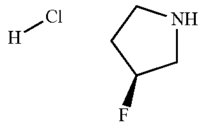 | 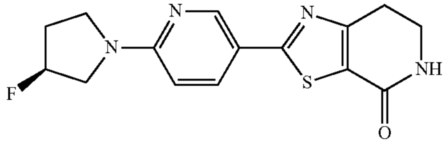<br>118 | 1. 79%<br>2. 2. $^1$H NMR (500 MHz, DMSO-$d_6$) δ 8.69-8.68 (m, 1H), 8.01 (dd, 1H), 7.76 (s, 1H), 6.59 (d, 1H), 5.53-5.31 (m, 1H), 4.03-3.55 (m, 3H), 3.47-3.44 (m, 3H), 2.94 (t, 2H), 2.27-2.13 (m, 2H)<br>3. 319.12 |
| 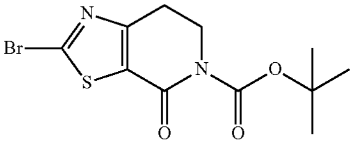 [SMILES: CC(C)(C)OC(=O)N1CCc2nc(Br)sc2C1=O] | 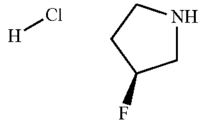 | 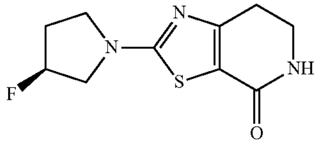<br>119 | 1. 80%<br>2. $^1$H NMR (500 MHz, DMSO-$d_6$) δ 7.31 (s, 1H), 5.59-5.34 (m, 1H), 3.80-3.55 (m, 3H), 3.55-3.42 (m, 1H), 3.37 (td, 2H), 2.73 (t, 2H), 2.34-2.16 (m, 2H)<br>3. 242.19 |

TABLE 4-continued
| Fluoro Derivative | Amine | Product Example | 1. Yield 2. $^{1}$H-NMR 3. $MH^{+}$ ESI) |
|---|---|---|---|
| 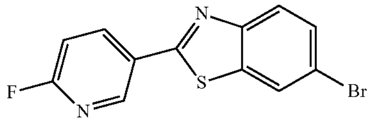 [SMILES: Fc1ccc(-c2nc3ccc(Br)cc3s2)cn1] | 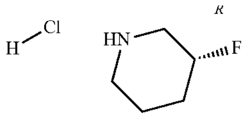 | 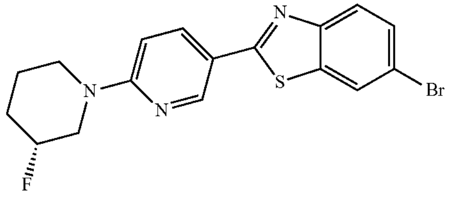 120 | 1. 57% 2. NA 3. 392.06 |
| 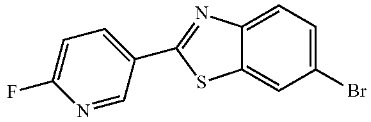 [SMILES: Fc1ccc(-c2nc3ccc(Br)cc3s2)cn1] | 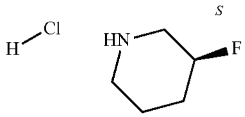 | 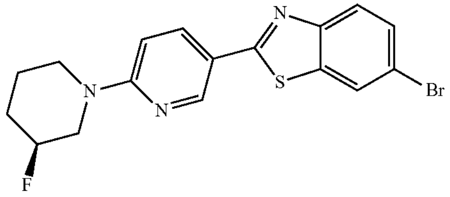 121 | 1. 54% 2. NA 3. 392.07 |
| 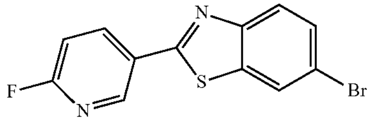 [SMILES: Fc1ccc(-c2nc3ccc(Br)cc3s2)cn1] | 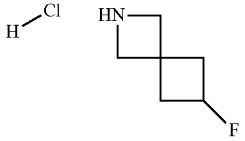 | 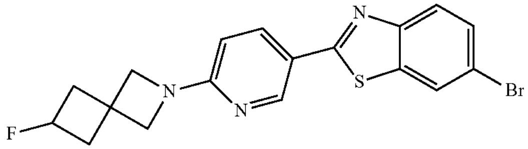 122 | 1. 57% 2. $^{1}$H NMR (400 MHz, DMSO-$d_6$) δ 8.74 (d, 1H), 8.37 (d, 1H), 8.11 (dd, 1H), 7.88 (d, 1H), 7.63 (dd, 1H), 6.47 (d, 1H), 5.04 (dp, 1H), 4.07 (d, 4H), 2.67 (tdd, 2H), 2.41 (dddd, 2H) 3. 404.7 |

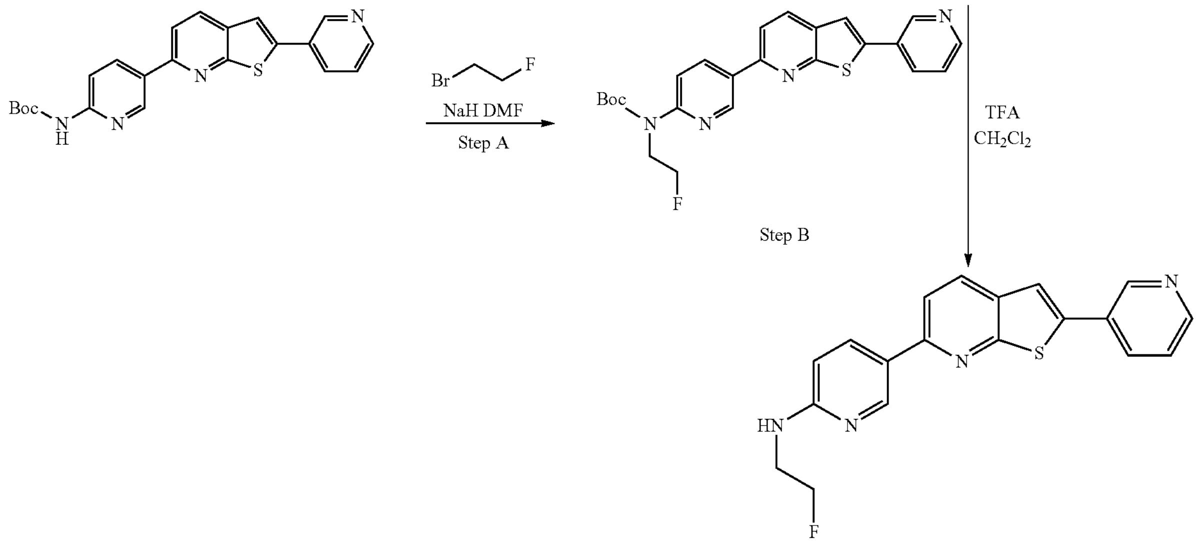

Step A:

A mixture of the title compound from Example 1 (0.070 g, 0.173 mmol) in N,N'-dimethylformamide (4 mL) was cooled at 00° C. and sodium hydride (0.005 g, 0.21 mmol) was added. The mixture was stirred at 00° C. for 1 h and warmed up to room temperature and stirred for additional 30 min and 1-bromo-2-fluoroethane (16 μL, 0.21 mmol) was added. The reaction mixture was stirred at room temperature for 1 hour and sodium hydride (0.005 g, 0.21 mmol) and 1-bromo-2-fluoroethane (0.016 mL, 0.21 mmol) were added again. After 2 hours, water (1 mL) was added and the solvents were removed under reduced pressure. The crude product was taken up in dichloromethane (10 mL), washed with brine (10 mL) and water (10 mL), dried over $Na_2SO_4$, and concentrated under reduced pressure. The residue was purified on HP-Sil SNAP cartridges using a Biotage Isolera One purification system employing a methanol/dichloromethane gradient (0/100→10/90) to afford the title compound (0.04 g, 51%).

$^1$H-NMR (400 MHz, DMSO-$d_6$) δ 9.14 (d, 1H), 9.06 (d, 1H), 8.62 (dd, 1H), 8.53 (dd, 1H), 8.35 (d, 1H), 8.21 (dt, 1H), 8.12 (d, 1H), 8.03 (s, 1H), 7.79 (d, 1H), 7.55 (dd, 1H), 4.64 (dt, 2H), 4.28 (dt, 2H), 1.49 (s, 9H).

MS (ESI); m/z=395.19 [M+H-$^t$Bu], 375.18 [M+H-$^t$Bu-HF]

Step B:

To the compound from Step A above (0.020 g, 0.044 mmol) was added dichloromethane (4 mL) and trifluoroacetic acid (400 μL) and the solution was stirred at room temperature for 5 h. The reaction mixture was concentrated under reduced pressure and water (10 ml) was added, followed by a 1 M aqueous sodium hydroxide solution (pH~13). The crude product was extracted with dichloromethane (2×10 mL), the organic fractions were collected, dried over $Na_2SO_4$, filtered and the solvents were removed under reduced pressure. The residue was purified on HP-Sil SNAP cartridges using a Biotage Isolera One purification system employing a methanol/dichloromethane gradient (0/100→20/80) to afford the title compound (0.007 g, 45%).

$^1$H-NMR (400 MHz, DMSO-$d_6$) δ 9.05 (d, 1H), 8.83 (d, 1H), 8.61 (dd, 1H), 8.29-8.15 (m, 3H), 8.04-7.86 (m, 2H), 7.55 (dd, 1H), 7.24 (t, 1H), 6.68 (d, 1H), 4.59 (dt, 2H), 3.67 (dq, 2H).

MS (ESI); m/z=351.20 [M+H]$^+$

Example 57

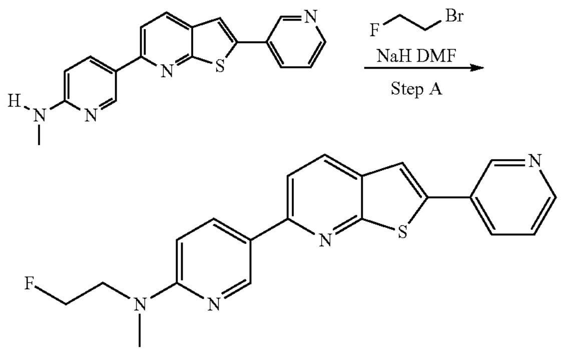

Step A:

To the title compound from Example 47 (0.015 g, 0.036 mmol) in N,N'-dimethylformamide (2 mL) was added sodium hydride (0.0034 g, 0.14 mmol) and the mixture was stirred at room temperature for 1 h, then 1-bromo-2-fluoroethane (0.01 mL, 0.15 mmol) was added. The reaction mixture was stirred at room temperature overnight. Water (2 mL) was added and the solvents were removed under reduced pressure. The crude product was taken up in dichlorometane (10 mL), washed with brine (10 mL) and water (10 mL), dried over $Na_2SO_4$, and concentrated under reduced pressure. The residue was purified on HP-Sil SNAP cartridges using a Biotage Isolera One purification system employing a methanol/dichloromethane gradient (0/100→10/90) to afford the title compound (0.004 g, 23%).

$^1$H-NMR (400 MHz, Chloroform-d) δ 9.02 (d, 1H), 8.85 (d, 1H), 8.61 (d, 1H), 8.31 (dd, 1H), 8.06 (d, 1H), 8.01-7.94 (m, 1H), 7.69 (d, 1H), 7.53 (s, 1H), 7.40 (dd, 1H), 6.67 (d, 1H), 4.70 (dt, 2H), 4.01 (dt, 2H), 3.21 (s, 3H).

MS (ESI); m/z=365.20 [M+H]$^+$

Example 58

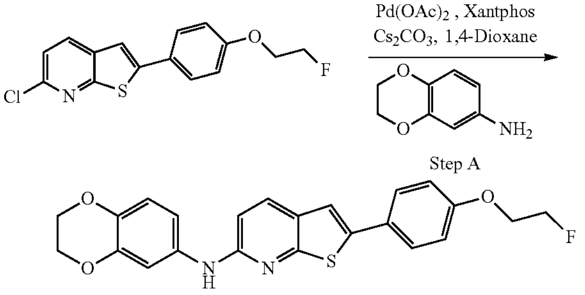

Step A:

An oven dried Schlenk flask was evacuated and back filled with argon gas. The procedure was repeated 3 to 4 times and the flask was cooled to room temperature. Then XANTPHOS (16.9 mg, 0.029 mmol) and palladium(II)-acetate (2.2 mg, 9.75 μmol) were added and degassed (argon). 1,4-Dioxane (5 mL) was added by syringe and the mixture was heated at 110° C. for 2 minutes to become a clear yellow solution, indicating the formation of the Pd-catalyst. Then commercially available 2,3-dihydrobenzo[b][1,4]dioxin-6-amine (16.2 mg, 0.107 mmol), the title compound from Preparative Example 14 (30 mg, 0.097 mmol) and cesium carbonate (95 mg, 0.292 mmol) were added under an argon atmosphere. The reaction mixture was heated at 110° C. in a sand bath for 2 h, cooled to room temperature and the solvents were removed under reduced pressure. The residue was purified on HP-Sil SNAP cartridges using a Biotage Isolera One purification system employing a dichloromethane/ethyl acetate gradient (90/10) to afford the title compound as a white solid (41.2 mg, 37%).

$^1$H-NMR (400 MHz, DMSO-$d_6$) δ 9.15 (s, 1H), 7.90 (d, 1H), 7.65 (d, 2H), 7.52 (s, 1H), 7.45 (d, 1H), 7.14-7.00 (m, 3H), 6.81 (d, 2H), 4.93-4.78 (m, 1H), 4.78-4.65 (m, 1H), 4.41-4.31 (m, 1H), 4.24 (dd, 5H)

MS (ESI); m/z=423.11 $[M+H]^+$

Examples 59 to 73 and 123 to 127

Following the procedure described in Example 58, except using the halogen derivatives and amines/amides indicated in the table below, the following compounds were prepared.

TABLE 5
| Halogen derivative | Amine/amide | Product Example | 1. Yield<br>2. $^1$H-NMR<br>3. MH$^+$ (ESI) |
|---|---|---|---|
| 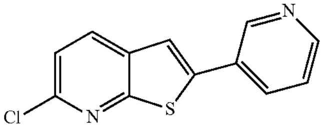 [SMILES: Clc1ccc2cc(-c3cccnc3)sc2n1] | 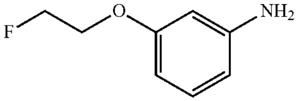 [SMILES: Nc1cccc(OCCF)c1] | 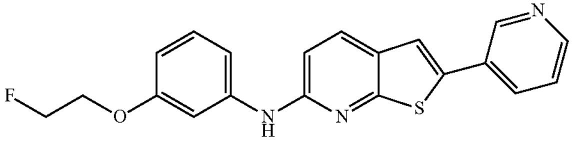<br>59 | 1. 58%<br>2. $^1$H-NMR (400 MHz, DMSO-d$_6$) δ 9.47 (s, 1H), 8.96 (s, 1H), 8.53 (d, 1H), 8.10 (d, 1H), 8.01 (d, 1H), 7.81 (s, 1H), 7.63-7.41 (m, 2H), 7.35-7.16 (m, 2H), 6.93 (d, 1H), 6.57 (d, 1H), 4.84 (t, 1H), 4.72 (t, 1H), 4.27 (t, 1H), 4.20 (t, 1H).<br>3. 365.93 |
| 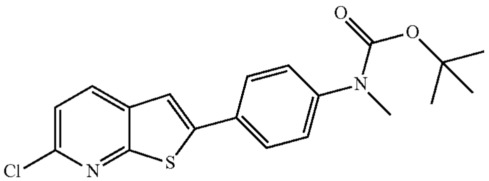 [SMILES: CN(C(=O)OC(C)(C)C)c1ccc(-c2cc3ccc(Cl)nc3s2)cc1] | 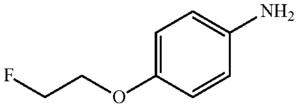 [SMILES: Nc1ccc(OCCF)cc1] | 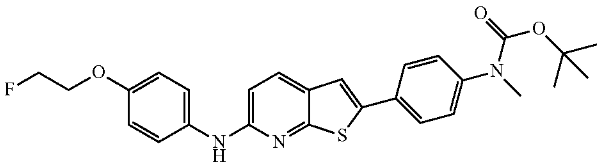<br>60 | 1. 59%<br>2. $^1$H-NMR (400 MHz, DMSO-d$_6$) δ 9.21 (s, 1H), 7.91 (d, 1H), 7.73-7.53 (m, 5H), 7.35 (d, 2H), 6.95 (d, 2H), 6.82 (d, 1H), 4.90-4.73 (m, 1H), 4.73-4.63 (m, 1H), 4.34-4.20 (m, 1H), 4.20-4.09 (m, 1H), 3.20 (s, 3H), 1.41 (s, 9H).<br>3. 494.45 |
| 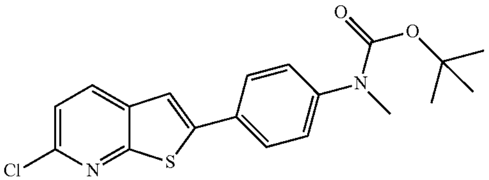 [SMILES: CN(C(=O)OC(C)(C)C)c1ccc(-c2cc3ccc(Cl)nc3s2)cc1] | 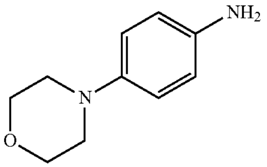 [SMILES: Nc1ccc(N2CCOCC2)cc1] | 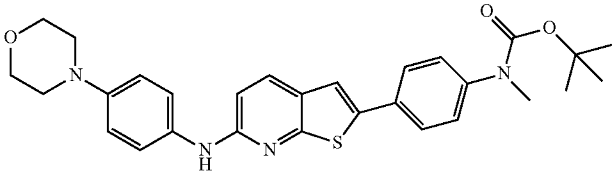<br>61 | 1. 55%<br>2. $^1$H-NMR (400 MHz, DMSO-d$_6$) δ 9.19 (s, 1H), 7.91 (d, 1H), 7.66 (d, 2H), 7.61 (s, 1H), 7.43 (d, 1H), 7.35 (d, 2H), 7.05 (dd, 1H), 6.81 (dd, 2H), 4.33-4.14 (m, 4H), 3.21 (s, 3H), 1.42 (s, 9H).<br>3. 490.42 |

TABLE 5-continued
| Halogen derivative | Amine/amide | Product Example | 1. Yield 2. $^1$H-NMR 3. MH$^+$ (ESI) |
|---|---|---|---|
| 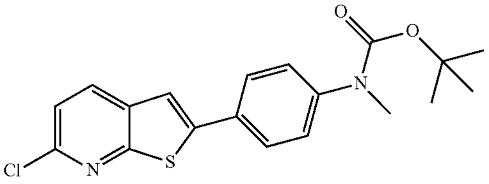 [SMILES: CN(C(=O)OC(C)(C)C)c1ccc(-c2cc3ccc(Cl)nc3s2)cc1] | 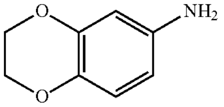 [SMILES: Nc1ccc2c(c1)OCCO2] | 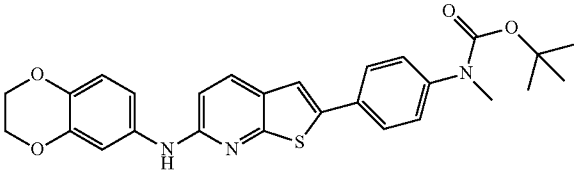 62 | 1. 61% 2. $^1$H-NMR (400 MHz, DMSO-$d_6$) δ 9.14 (s, 1H), 7.89 (d, 1H), 7.66 (d, 2H), 7.63-7.54 (m, 3H), 7.35 (d, 2H), 6.95 (d, 2H), 6.81 (d, 1H), 3.79-3.72 (m, 4H), 3.21 (s, 3H), 3.09-3.01 (m, 4H), 1.42 (s, 9H). 3. 517.56 |
| 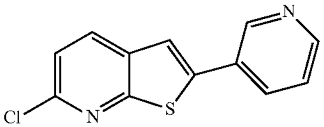 [SMILES: Clc1ccc2cc(-c3cccnc3)sc2n1] | 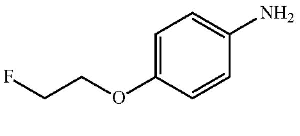 | 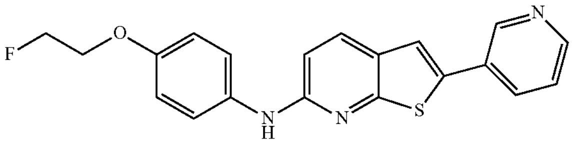 63 | 1. 62% 2. $^1$H-NMR (400 MHz, DMSO-$d_6$) δ 9.28 (s, 1H), 8.94 (d, 1H), 8.52 (dd, 1H), 8.08 (dt, 1H), 7.95 (d, 1H), 7.78 (s, 1H), 7.65 (d, 2H), 7.48 (dd, 1H), 6.97 (d, 2H), 6.85 (d, 1H), 4.87-4.75 (m, 1H), 4.73-4.63 (m, 1H), 4.32-4.22 (m, 1H), 4.22-4.13 (m, 1H). 3. 365.82 |
| 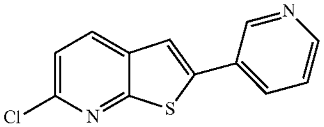 [SMILES: Clc1ccc2cc(-c3cccnc3)sc2n1] | 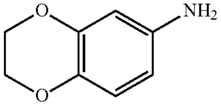 | 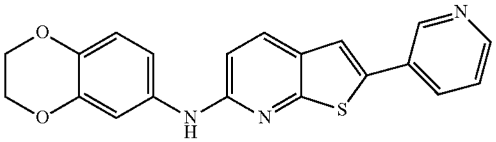 64 | 1. 69% 2. $^1$H-NMR (400 MHz, DMSO-$d_6$) δ 9.25 (s, 1H), 8.94 (s, 1H), 8.52 (d, 1H), 8.08 (d, 1H), 7.94 (d, 1H), 7.78 (s, 1H), 7.57-7.41 (m, 2H), 7.15-6.99 (m, 1H), 6.82 (t, 2H), 4.37-4.13 (m, 4H). 3. 361.80 |

TABLE 5-continued
| Halogen derivative | Amine/amide | Product Example | 1. Yield 2. $^{1}$H-NMR 3. $MH^+$ (ESI) |
|---|---|---|---|
| 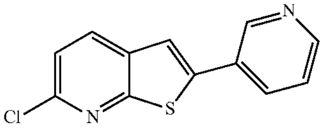 [SMILES: Clc1ccc2cc(-c3cccnc3)sc2n1] | 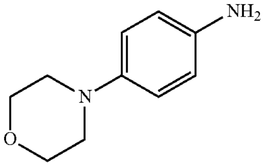 [SMILES: Nc1ccc(N2CCOCC2)cc1] | 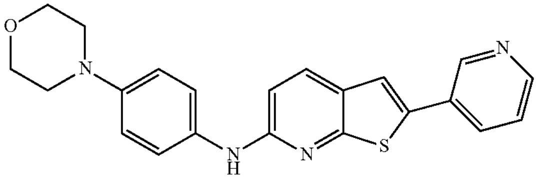 65 | 1. 47% 2. $^{1}$H-NMR (400 MHz, DMSO-$d_6$) δ 9.21 (s, 1H), 8.94 (s, 1H), 8.56-8.46 (m, 1H), 8.08 (d, 1H), 7.93 (d, 1H), 7.77 (s, 1H), 7.59 (d, 2H), 7.51-7.43 (m, 1H), 6.95 (d, 2H), 6.83 (d, 1H), 3.75 (s, 4H), 3.05 (s, 4H). 3. 389.1 |
| 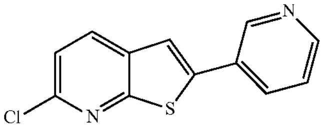 [SMILES: Clc1ccc2cc(-c3cccnc3)sc2n1] | 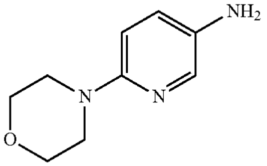 [SMILES: Nc1ccc(N2CCOCC2)nc1] | 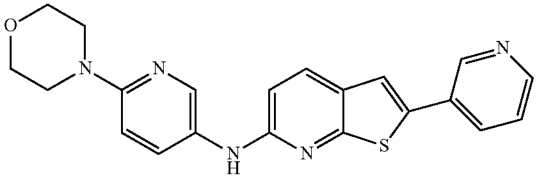 66 | 1. 34% 2. $^{1}$H-NMR (400 MHz, DMSO-$d_6$) δ 9.24 (s, 1H), 8.94 (s, 1H), 8.51 (d, 1H), 8.46 (s, 1H), 8.08 (d, 1H), 7.96 (t, 2H), 7.78 (s, 1H), 7.53-7.42 (m, 1H), 6.89 (d, 1H), 6.82 (d, 1H), 3.72 (s, 4H), 3.37 (s, 4H). 3. 390.1 |
| 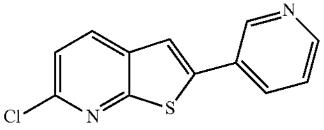 [SMILES: Clc1ccc2cc(-c3cccnc3)sc2n1] | 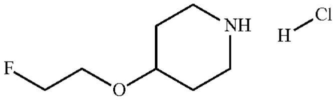 | 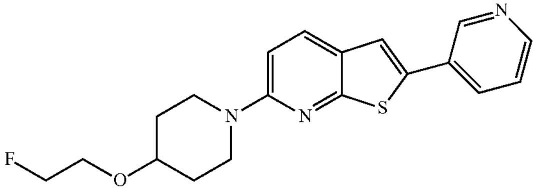 67 | 1. 21% 2. $^{1}$H-NMR (400 MHz, DMSO-$d_6$) δ 8.92 (d, 1H), 8.51 (dd, 1H), 8.05 (dt, 1H), 7.94 (d, 1H), 7.74 (s, 1H), 7.46 (dd, 1H), 7.01 (d, 1H), 4.63-4.44 (m, 2H), 4.05 (dt, 2H), 3.77-3.58 (m, 3H), 3.27 (ddd, 2H), 1.99-1.88 (m, 2H), 1.48 (dtd, 2H). 3. 358.17 |

TABLE 5-continued
| Halogen derivative | Amine/amide | Product Example | 1. Yield<br>2. $^1$H-NMR<br>3. $MH^+$ (ESI) |
|---|---|---|---|
| 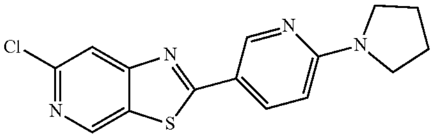 [SMILES: Clc1cc2nc(-c3ccc(N4CCCC4)nc3)sc2cn1] | 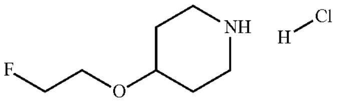 | 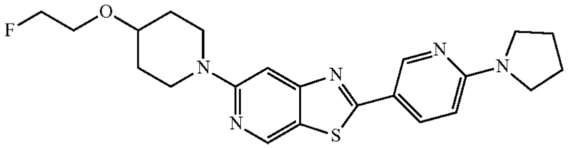<br>68 | 1. 8%<br>2. $^1$H NMR (400 MHz, DMSO-$d_6$) δ 8.79 (d, 1H), 8.77 (s, 1H), 8.09 (dd, 1H), 7.28 (s, 1H), 6.61 (d, J = 9.0 Hz, 1H), 4.53 (dt, 2H), 4.03 (dt, 2H), 3.79-3.72 (m, 1H), 3.70-3.65 (m, 1H), 3.60 (p, 1H), 3.50 (s, 4H), 3.18 (ddd, 2H), 2.03-1.87 (m, 6H), 1.48 (ddt, 2H)<br>3. 428.14 |
| 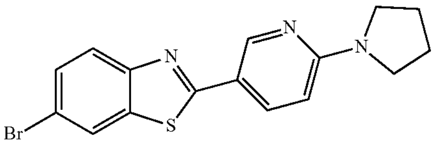 [SMILES: Brc1ccc2nc(-c3ccc(N4CCCC4)nc3)sc2c1] | 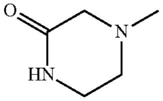 | 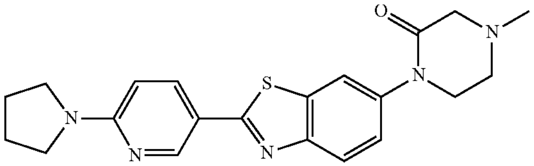<br>69 | 1. 64%<br>2. $^1$H NMR (400 MHz, DMSO-$d_6$) δ 8.77 (d, 1H), 8.11 (dd, 1H), 8.05 (d, 1H), 7.94 (d, 1H), 7.44 (dd, 1H), 6.61 (d, 1H), 3.73 (t, 2H), 3.57-3.44 (m, 4H), 3.15 (s, 2H), 2.76 (t, 2H), 2.31 (s, 3H), 2.05-1.93 (m, 4H).<br>3. 394.05 |
| 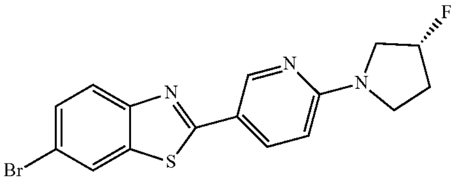 [SMILES: F[C@@H]1CCN(c2ccc(-c3nc4ccc(Br)cc4s3)cn2)C1] | 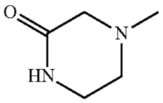 | 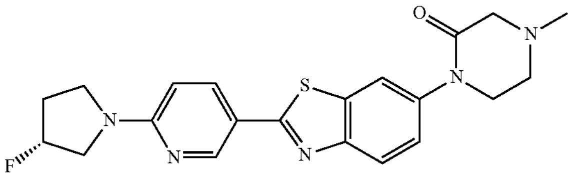<br>70 | 1. 39%<br>2. $^1$H NMR (400 MHz, DMSO-$d_6$) δ 8.79 (d, 1H), 8.15 (dd, 1H), 8.06 (s, 1H), 7.95 (d, 1H), 7.50-7.39 (m, 1H), 6.67 (d, 1H), 5.48 (d, 1H), 3.92-3.59 (m, 5H), 3.59-3.44 (m, 1H), 3.14 (s, 2H), 2.75 (t, 2H), 2.30 (s, 5H).<br>3. 412.02 |

TABLE 5-continued
| Halogen derivative | Amine/amide | Product Example | 1. Yield<br>2. $^1$H-NMR<br>3. $MH^+$ (ESI) |
|---|---|---|---|
| 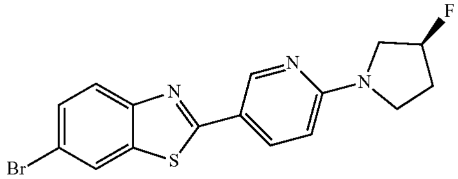 [SMILES: F[C@H]1CCN(c2ccc(-c3nc4ccc(Br)cc4s3)cn2)C1] | 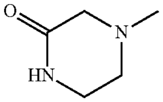 | 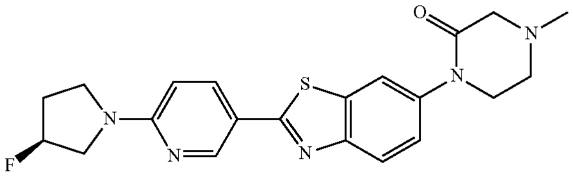<br>71 | 1. 49%<br>2. $^1$H NMR (400 MHz, DMSO-$d_6$) δ 8.79 (d, 1H), 8.16 (dd, 1H), 8.06 (d, 1H), 7.95 (d, 1H), 7.44 (dd, 1H), 6.68 (d, 1H), 5.48 (d, 1H), 3.95-3.60 (m, 5H), 3.52 (td, 1H), 3.14 (s, 2H), 2.76 (t, 2H), 2.30 (s, 5H)<br>3. 412.03 |
| 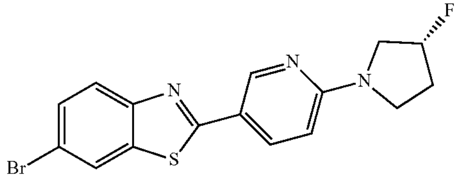 [SMILES: F[C@@H]1CCN(c2ccc(-c3nc4ccc(Br)cc4s3)cn2)C1] | 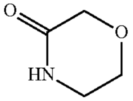 | 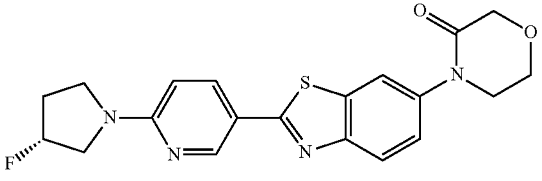<br>72 | 1. 59%<br>2. $^1$H NMR (400 MHz, DMSO-$d_6$) δ 8.80 (s, 1H), 8.21-8.07 (m, 2H), 7.97 (d, 1H), 7.51 (d, 1H), 6.74-6.63 (m, 1H), 5.49 (d, 1H), 4.24 (s, 2H), 4.05-3.97 (m, 2H), 3.92-3.61 (m, 5H), 3.52 (q, 1H), 2.24 (dd, 2H)<br>3. 399.05 |
| 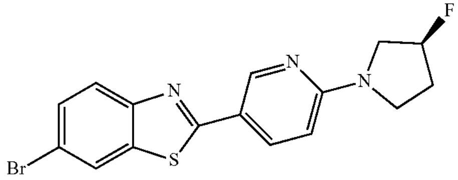 [SMILES: F[C@H]1CCN(c2ccc(-c3nc4ccc(Br)cc4s3)cn2)C1] | 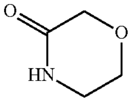 | 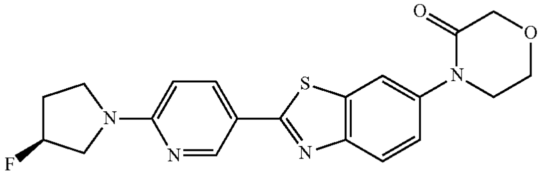<br>73 | 1. 54%<br>2. $^1$H NMR (400 MHz, DMSO-$d_6$) δ 8.80 (s, 1H), 8.24-8.05 (m, 2H), 7.97 (d, 1H), 7.51 (d, 1H), 6.76-6.59 (m, 1H), 5.49 (d, 1H), 4.24 (s, 2H), 4.07-3.96 (m, 2H), 3.93-3.60 (m, 5H), 3.53 (dd, 1H), 2.39-2.09 (m, 2H)<br>3. 399.03 |

TABLE 5-continued
| Halogen derivative | Amine/amide | Product Example | 1. Yield<br>2. $^{1}$H-NMR<br>3. MH$^{+}$ (ESI) |
|---|---|---|---|
| 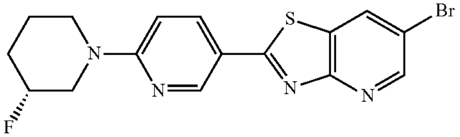 [SMILES: F[C@@H]1CCCN(c2ccc(-c3nc4ncc(Br)cc4s3)cn2)C1] | 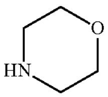 | 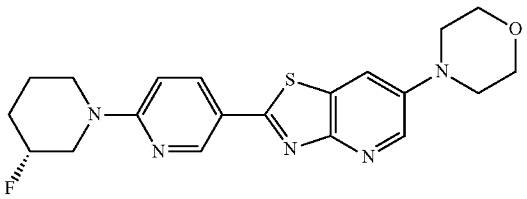<br>123 | 1. 20%<br>2. $^{1}$H NMR (500 MHz, DMSO-$d_6$) δ 8.76 (d, 1H), 8.45 (d, 1H), 8.10 (dd, 1H), 8.05 (d, 1H), 7.03 (d, 1H), 4.90-4.71 (m, 1H), 4.15-4.07 (m, 1H), 3.99-3.89 (m, 1H), 3.82-3.68 (m, 5H), 3.48-3.42 (m, 1H), 3.27-3.23 (m, 4H), 1.91 (d, 2H), 1.84-1.71 (m, 1H), 1.65-1.51 (m, 1H)<br>3. 399.19 |
| 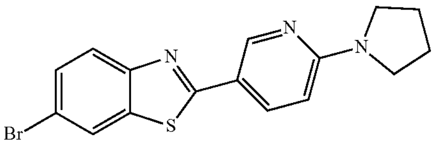 [SMILES: Brc1ccc2nc(-c3ccc(N4CCCC4)nc3)sc2c1] | 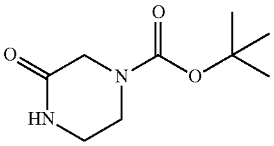 | 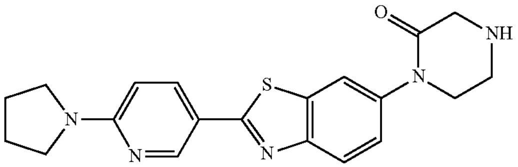<br>124 | 1. 44%<br>2. $^{1}$H NMR (400 MHz, DMSO-$d_6$) δ 8.76 (d, 1H), 8.10 (dd, 1H), 8.03 (d, 1H), 7.93 (d, 1H), 7.42 (dd, 1H), 6.60 (d, 1H), 3.66 (t, 2H), 3.54-3.44 (m, 4H), 3.42 (s, 2H), 3.04 (t, 2H), 2.80 (s, 1H), 2.05-1.87 (m, 4H)<br>3. 380.14 |
| 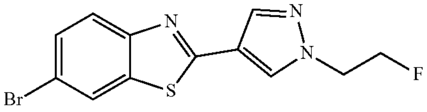 [SMILES: FCCn1cc(-c2nc3ccc(Br)cc3s2)cn1] | 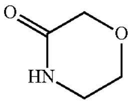 | 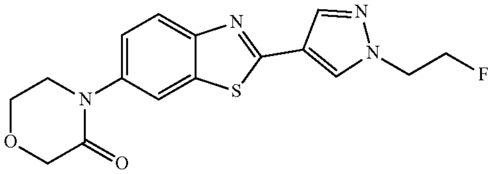<br>125 | 1. 18%<br>2. $^{1}$H NMR (400 MHz, DMSO-$d_6$) δ 8.60 (s, 1H), 8.14 (d, 1H), 7.95 (d, 1H), 7.52 (d, 1H), 4.97-4.73 (m, 2H), 4.54 (dt, 2H), 4.24 (s, 2H), 4.00 (d, 2H), 3.81 (d, , 2H)<br>3. 347.06 |

TABLE 5-continued
| Halogen derivative | Amine/amide | Product Example | 1. Yield<br>2. ¹H-NMR<br>3. $MH^+$ (ESI) |
|---|---|---|---|
| 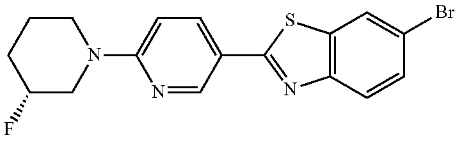 | 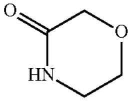 | 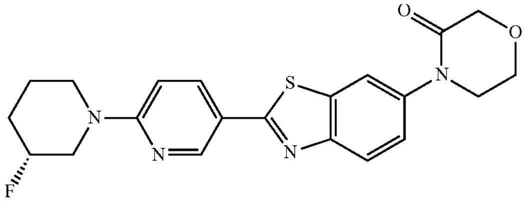<br>126 | 1. 52%<br>2. ¹H NMR (400 MHz, DMSO-$d_6$) δ 8.77 (d, 1H), 8.21-8.04 (m, 2H), 7.97 (d, 1H), 7.52 (dd, 1H), 7.03 (d, 1H), 4.98-4.67 (m, 1H), 4.24 (s, 2H), 4.15-4.05 (m, 1H), 4.04-3.98 (m, 2H), 3.98-3.90 (m, 1H), 3.85-3.78 (m, 2H), 3.78-3.67 (m, 1H), 3.50-3.39 (m, 1H), 2.07-1.83 (m, 2H), 1.83-1.67 (m, 1H), 1.64-1.49 (m, 1H)<br>3. 413.16 |
| 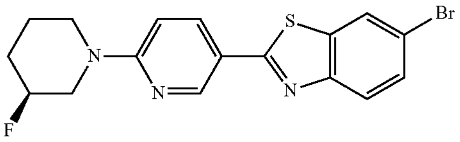 | 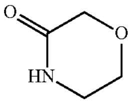 | 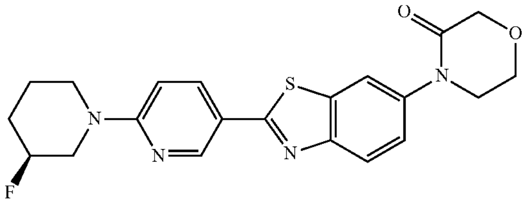<br>127 | 1. 35%<br>2. ¹H NMR (400 MHz, DMSO-$d_6$) δ 8.79 (d, 1H), 8.14 (dt, 2H), 7.99 (dd, 1H), 7.53 (dt, 1H), 7.04 (d, 1H), 4.96-4.69 (m, 1H), 4.26 (s, 2H), 4.11 (td, 1H), 4.03 (t, 2H), 3.96 (dd, 1H), 3.83 (t, 2H), 3.79-3.69 (m, 1H), 3.47 (dd, 1H), 2.09-1.69 (m, 3H), 1.59 (t, 1H)<br>3. 413.16 |

Example 74

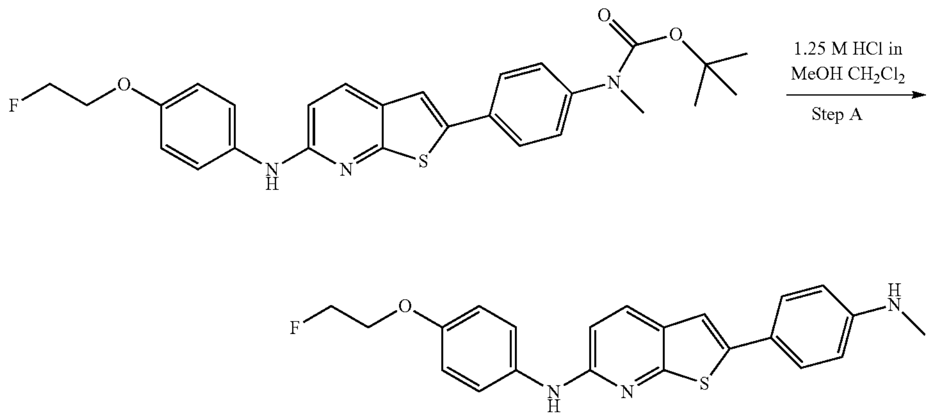 [SMILES: CN(C(=O)OC(C)(C)C)c1ccc(-c2cc3ccc(Nc4ccc(OCCF)cc4)nc3s2)cc1 ; CNc1ccc(-c2cc3ccc(Nc4ccc(OCCF)cc4)nc3s2)cc1]

Step A:

A solution of the title compound from Example 60 (0.037 g, 0.075 mmol) in dichloromethane (2 mL) and 1.25 N HCl (2 mL) in methanol was stirred at room temperature for 6 hours. The reaction mixture was concentrated under reduced pressure to dryness. 1N NaOH was added and the aqueous phase was extracted with dichloromethane (3×20 mL). The combined organics were dried over $Na_2SO_4$, filtered and concentrated under reduced pressure to afford the title compound (0.012 g, 41%).

$^1$H-NMR (400 MHz, DMSO-$d_6$) δ 9.09 (s, 1H), 7.82 (d, 1H), 7.62 (d, 2H), 7.43 (d, 2H), 7.29 (s, 1H), 6.94 (d, 2H), 6.77 (d, 1H), 6.59 (d, 2H), 5.98 (q, 1H), 4.87-4.73 (m, 1H), 4.73-4.62 (m, 1H), 4.32-4.20 (m, 1H), 4.20-4.11 (m, 1H), 2.71 (d, 3H).

MS (ESI); m/z=394.10 $[M+H]^+$

Examples 75 and 76

Following the procedure described in Example 74, except using the Boc-protected derivatives indicated in the table below, the following compounds were prepared.

TABLE 6

| Boc-protected derivative | Product Example | 1. Yield<br>2. $^1$H-NMR<br>3. $MH^+$ (ESI) |
|---|---|---|
| 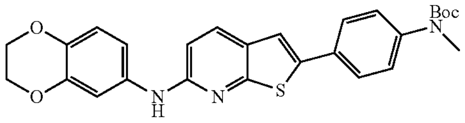 [SMILES: CN(C(=O)OC(C)(C)C)c1ccc(-c2cc3ccc(Nc4ccc5c(c4)OCCO5)nc3s2)cc1] | 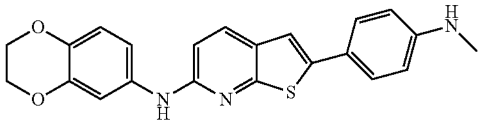<br>75 | 1. 34%<br>2. $^1$H-NMR (400 MHz, DMSO-$d_6$) δ 9.05 (s, 1H), 7.82 (d, 1H), 7.50-7.37 (m, 3H), 7.29 (s, 1H), 7.03 (dd, 1H), 6.77 (dd, 2H), 6.59 (d, 2H), 6.06-5.89 (m, 1H), 4.22 (dd, 4H), 2.71 (d, 3H).<br>3. 390.08 |
| 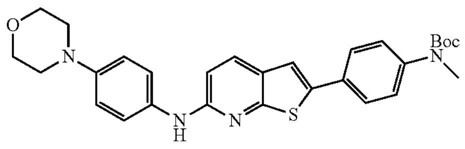 [SMILES: CN(C(=O)OC(C)(C)C)c1ccc(-c2cc3ccc(Nc4ccc(N5CCOCC5)cc4)nc3s2)cc1] | 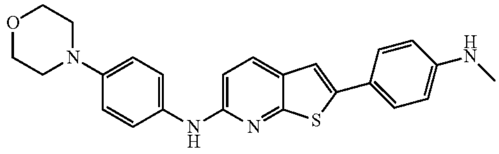<br>76 | 1. 22%<br>2. $^1$H-NMR (400 MHz, DMSO-$d_6$) δ 9.00 (s, 1H), 7.79 (d, 1H), 7.56 (d, 2H), 7.42 (d, 2H), 7.28 (s, 1H), 6.92 (d, 2H), 6.75 (d, 1H), 6.58 (d, 2H), 5.96 (d, 1H), 3.82-3.65 (m, 4H), 3.10-2.98 (m, 4H), 2.70 (d, 3H).<br>3. 417.14 |

Example 77

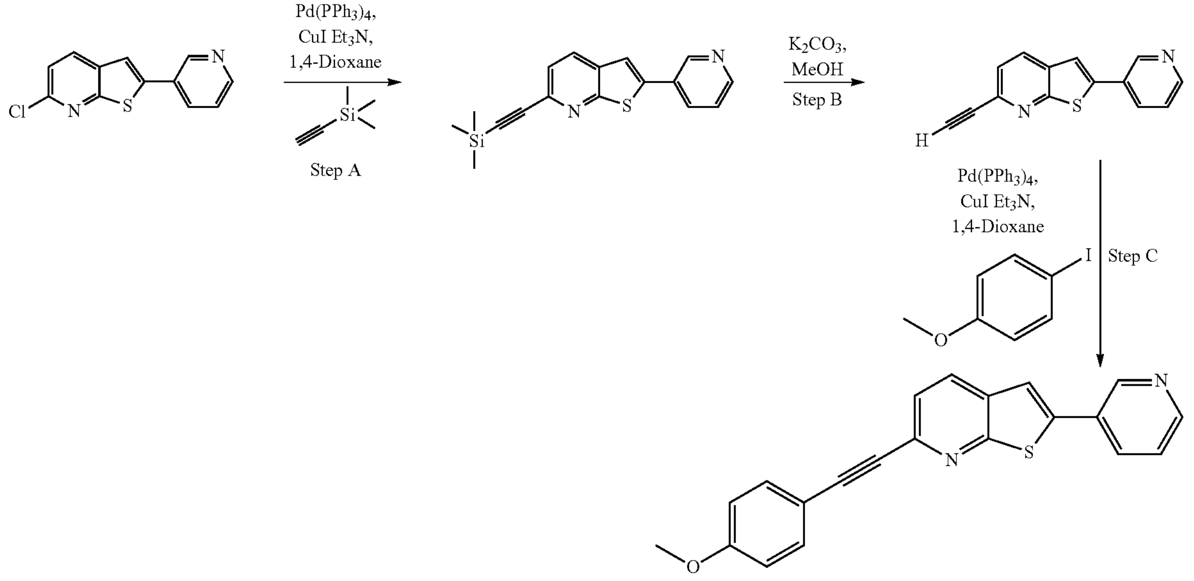

Step A:

An oven dried Schlenk flask was evacuated and back filled with argon gas. The procedure was repeated 3 to 4 times and the flask was cooled to room temperature. Then, 1,4-dioxane (8 mL) was added by syringe and degassed (argon). The title compound from Preparative Example 6 (200 mg, 0.811 mmol), ethynyltrimethylsilane (0.458 mL, 3.240 mmol), copper(I) iodide (7.72 mg, 0.041 mmol), $Pd(Ph_3P)_4$ (94 mg, 0.081 mmol) and triethylamine (0.451 mL, 3.24 mmol) were added under an argon atmosphere. The reaction mixture was heated at 100° C. in a sand bath for 4 h, cooled to room temperature and the reaction mixture was diluted with water (50 mL). The aqueous phase was then extracted with dichloromethane (3×50 mL). The combined organics were dried over $Na_2SO_4$, filtered and concentrated under reduced pressure. The residue was purified on HP-Sil SNAP cartridges using a Biotage Isolera One purification system employing a dichloromethane/ethyl acetate gradient (90/10→70/30) to afford the title compound (200 mg, 80%).

$^1$H-NMR (400 MHz, DMSO-$d_6$) δ 9.06 (s, 1H), 8.71-8.55 (m, 1H), 8.25 (d, 1H), 8.21 (d, 1H), 8.03 (s, 1H), 7.59 (d, 1H), 7.55 (dd, 1H), 0.28 (s, 9H)

MS (ESI); m/z=308.76 $[M+H]^+$

Step B:

An oven dried Schlenk flask was evacuated and back filled with argon gas. The procedure was repeated 3 to 4 times and the flask was cooled to room temperature. Then, methanol (10 mL) was added by syringe and degassed (argon). The title compound from Step A above (200 mg, 0.648 mmol), followed by potassium carbonate (358 mg, 2.590 mmol) were added under an argon atmosphere. The reaction mixture was stirred at room temperature for 1 hour. Then, the reaction mixture was concentrated under reduced pressure to dryness. Water (50 mL) was added and the aqueous phase was extracted with dichloromethane (3×50 mL). The combined organics were dried over $Na_2SO_4$, filtered and concentrated under reduced pressure to afford the title compound (153 mg, 74%).

$^1$H-NMR (400 MHz, DMSO-$d_6$) δ 9.06 (d, 1H), 8.67-8.59 (m, 1H), 8.28 (d, 1H), 8.22 (dt, 1H), 8.04 (s, 1H), 7.62 (d, 1H), 7.55 (dd, 1H), 4.50 (s, 1H).

MS (ESI); m/z=236.60 $[M+H]^+$

Step C:

An oven dried Schlenk flask was evacuated and back filled with argon gas. The procedure was repeated 3 to 4 times and the flask was cooled to room temperature. Then, 1,4-dioxane (8 mL) was added by syringe and degassed (argon). The title compound from Step B above (20 mg, 0.085 mmol), 1-iodo-4-methoxybenzene (24 mg, 0.102 mmol), copper(I) iodide (0.8 mg, 0.004 mmol), $Pd(Ph_3P)_4$ (9.8 mg, 0.008 mmol) and triethylamine (23 μL, 0.169 mmol) were added under an argon atmosphere. The reaction mixture was heated at 100° C. in a sand bath for 4 h, cooled to room temperature and the reaction mixture was diluted with water (50 mL). The aqueous phase was then extracted with dichloromethane (3×50 mL). The combined organics were dried over $Na_2SO_4$, filtered and concentrated under reduced pressure. The residue was purified on HP-Sil SNAP cartridges using a Biotage Isolera One purification system employing a dichloromethane/ethyl acetate gradient (95/5→85/25) to afford the title compound (5 mg, 15%).

$^1$H-NMR (400 MHz, DMSO-$d_6$) δ 8.30-8.20 (m, 2H), 8.07-8.00 (m, 1H), 7.75-7.56 (m, 5H), 7.52-7.46 (m, 1H), 7.03 (d, 2H), 3.82 (s, 3H)

MS (ESI); m/z=342.79 $[M+H]^+$

Example 78

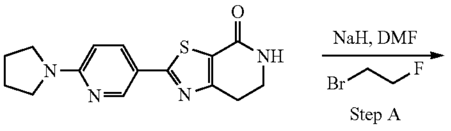

-continued

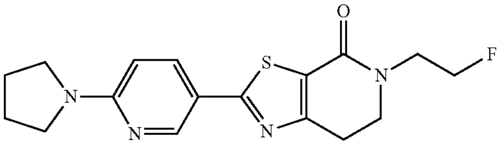

Step A:

An oven dried Schlenk flask was evacuated and back filled with argon gas. The procedure was repeated 3 to 4 times and the flask was cooled to room temperature. Then, DMF (2 mL) was added by syringe and degassed (argon). The title compound from Preparative Example 20 (15 mg, 0.050 mmol) was added under an argon atmosphere, followed by the addition of sodium hydride (1.5 mg, 0.060 mmol). The reaction mixture was stirred at room temperature for 1 hour and 1-bromo-2-fluoroethane (9.5 mg, 0.075 mmol) was added. Then, the reaction mixture was heated at 60° C. for 18 hours. The crude product was allowed to cool to room temperature and EtOAC (40 mL) was added. The organic layer was washed several times with brine, dried over $Na_2SO_4$, filtered and dried under reduced pressure. The residue was purified on HP-Sil SNAP cartridges using a Biotage Isolera One purification system employing a dichloromethane/methanol gradient (98/2→92/8) to afford the title compound (5 mg, 25%).

$^1$H-NMR (400 MHz, DMSO-$d_6$) δ 8.70 (d, 1H), 8.00 (dd, 1H), 6.55 (d, 1H), 4.61 (dt, 2H), 3.83-3.66 (m, 4H), 3.55-3.40 (m, 4H), 3.06 (t, 2H), 2.07-1.88 (m, 4H)

MS (ESI); m/z=347.27 $[M+H]^+$

Examples 79 and 128

Following the procedure described in Example 78, the following compound was prepared.

Example 80

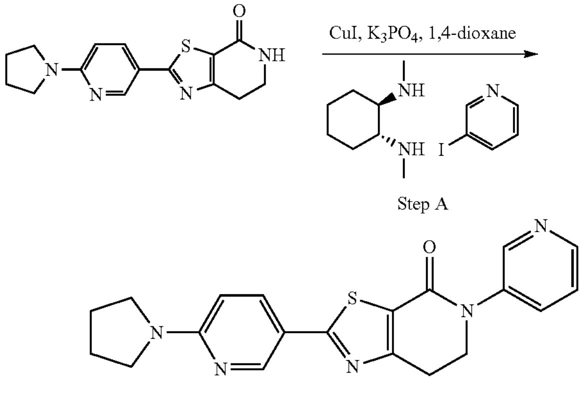

Step A:

An oven dried Schlenk flask was evacuated and back filled with argon gas. The procedure was repeated 3 to 4 times and the flask was cooled to room temperature. Then, 1,4-dioxane (2 mL) was added by syringe and degassed (argon). The title compound from Preparative Example 20 (20 mg, 0.067 mmol), 3-iodopyridine (16.4 mg, 0.080 mmol), copper(I) iodide (1.2 mg, 0.007 mmol), (1R,2R)—N1,N2-dimethylcyclohexane-1,2-diamine (2.8 mg, 0.020 mmol) and potassium phosphate (35.3 mg, 0.166 mmol) were added under an argon atmosphere. The reaction mixture was heated at 100° C. in a sand bath for 18 h, cooled to room temperature and the solvents were removed under reduced pressure. The residue was purified on HP-Sil SNAP cartridges using a Biotage Isolera One purification system employing a dichloromethane/ethyl acetate gradient (98/2→95/5) to afford the title compound (11 mg, 43%).

TABLE 7

| Starting material | Product Example | 1. Yield<br>2. $^1$H-NMR<br>3. $MH^+$ (ESI) |
|---|---|---|
| 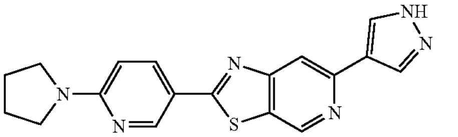 [SMILES: c1n[nH]cc1-c1cc2nc(-c3ccc(N4CCCC4)nc3)sc2cn1] | 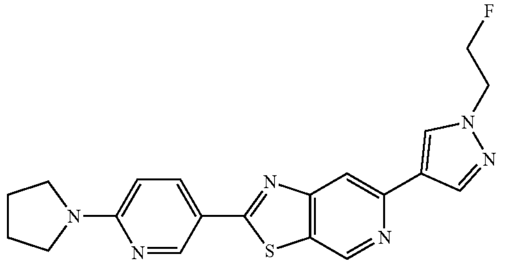<br>79 | 1. 35%<br>2. $^1$H NMR (400 MHz, DMSO-$d_6$) δ 9.18 (s, 1H), 8.85 (d, 1H), 8.42 (s, 1H), 8.21 (s, 1H), 8.18 (s, 1H), 8.14 (dd, 1H), 6.62 (d, 1H), 4.82 (dt, 2H), 4.49 (dt, 2H), 3.50 (s, 4H), 1.99 (m, 4H).<br>3. 395.08 |
| 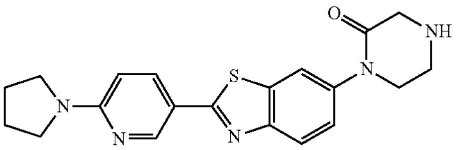 [SMILES: O=C1CNCCN1c1ccc2nc(-c3ccc(N4CCCC4)nc3)sc2c1] | 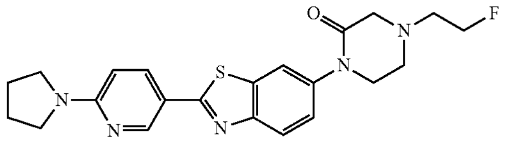<br>128 | 1. 18%<br>2. $^1$H NMR (400 MHz, DMSO-$d_6$) δ 8.77 (s, 1H), 8.11 (d, 1H), 8.06 (s, 1H), 7.93 (d, 1H), 7.44 (d, 1H), 6.61 (d, 1H), 4.78-4.48 (m, 2H), 3.80-3.67 (m, 2H), 3.59-3.40 (m, 4H), 3.31 (s, 2H), 2.91 (s, 2H), 2.80 (dd, 2H), 1.98 (s, 4H).<br>3. 426.35 |

$^1H$-NMR (400 MHz, DMSO-$d_6$) 8.75 (d, 1H), 8.65 (s, 1H), 8.44 (d, 1H), 8.12-7.97 (m, 1H), 7.84 (d, 1H), 7.47 (dd, 1H), 6.58 (d, 1H), 4.15 (t, 2H), 3.48 (s, 4H), 3.23 (t, 2H), 1.97 (s, 4H)

MS (ESI); m/z=378.46 $[M+H]^+$

Examples 129 and 130

Following the procedure described in Example 80, the following compounds were prepared.

TABLE 8

| Amide derivative | Product Example | 1. Yield 2. $^1H$-NMR 3. $MH^+$ (ESI) |
|---|---|---|
| 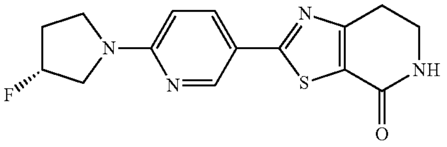 [SMILES: O=C1NCCc2nc(-c3ccc(N4CC[C@@H](F)C4)nc3)sc21] | 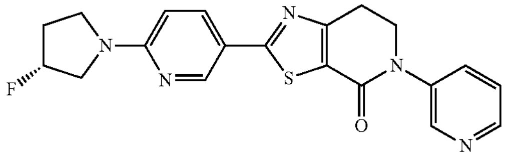 129 | 1. 48% 2. $^1H$ NMR (500 MHz, DMSO-$d_6$) δ 8.81-8.76 (m, 1H), 8.69-8.62 (m, 1H), 8.50-8.40 (m, 1H), 8.10 (dd, 1H), 7.84 (ddd, 1H), 7.47 (dd, 1H), 6.65 (d, 1H), 5.56-5.40 (m, 1H), 4.15 (t, 2H), 3.99-3.59 (m, 3H), 3.51 (td, 1H), 3.25 (t, 2H), 2.42-2.10 (m, 2H) 3. 396.12 |
| 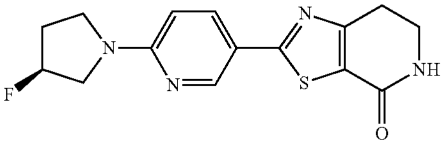 [SMILES: O=C1NCCc2nc(-c3ccc(N4CC[C@H](F)C4)nc3)sc21] | 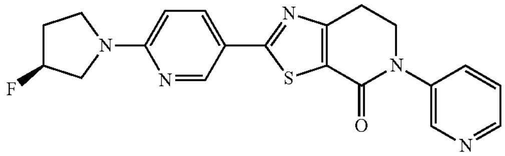 130 | 1. 64% 2. $^1H$ NMR (500 MHz, DMSO-$d_6$) δ 8.78-8.76 (m, 1H), 8.66-8.52 (m, 1H), 8.45-8.44 (m, 1H), 8.09 (dd, 1H), 7.84 (ddd, 1H), 7.47 (dd, 1H), 6.65 (d, 1H), 5.56-5.40 (m, 1H), 4.15 (t, 2H), 3.99-3.59 (m, 3H), 3.51 (td, 1H), 3.24 (t, 2H), 2.42-2.10 (m, 2H) 3. 396.10 |

Example 131

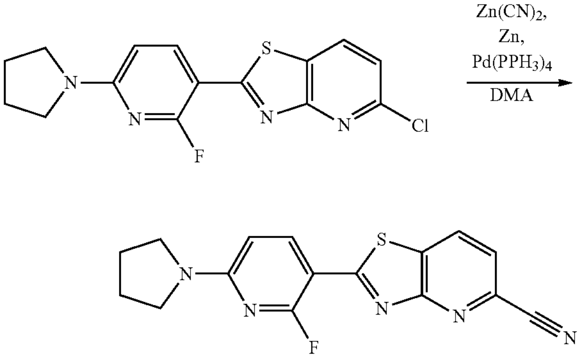

Step A:

An oven dried Schlenk flask was evacuated and back filled with argon gas. The procedure was repeated 3 to 4 times and the flask was cooled to room temperature. Then, DMA (5 mL) was added by syringe and degassed (argon). The title compound from Preparative Example 25 (50 mg, 0.067 mmol), dicyanozinc (52.6 mg, 0.448 mmol), zinc (29.3 mg, 0.448 mmol) and $Pd(Ph_3P)_4$ (8.6 mg, 7.47 μmol) were added under an argon atmosphere. The reaction mixture was heated at 120° C. in a sand bath for 18 h. The crude product was allowed to cool to room temperature and dichloromethane (50 mL) was added. The organic layer was washed several times with 1N NaOH, dried over $Na_2SO_4$, filtered and dried under reduced pressure. The residue was purified on HP-Sil SNAP cartridges using a Biotage Isolera One purification system employing a dichloromethane/methanol eluent (98/2). Then, the solid was washed with DCM (20 mL) and the mother liquor was concentrated under reduced pressure to afford the title compound (6 mg, 12%).

$^1H$ NMR (400 MHz, Chloroform-d) δ 8.78-8.56 (m, 1H), 8.31 (d, 1H), 7.61 (d, 1H), 6.40 (dd, 1H), 3.80-3.34 (m, 4H), 2.07 (s, 4H)

MS (ESI); m/z=326.11 $[M+H]^+$

Example 132

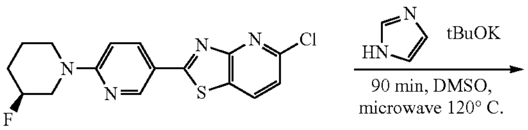

-continued

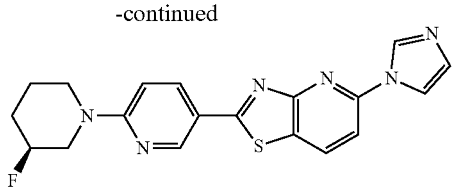

In a 2 mL microwave tube was added (S)-5-chloro-2-(6-(3-fluoropiperidin-1-yl)pyridin-3-yl)thiazolo[4,5-b]pyridine (26 mg, 0.075 mmol) Example 93, potassium 2-methylpropan-2-olate (16.73 mg, 0.149 mmol) and 1H-imidazole (6.09 mg, 0.089 mmol) in DMSO (1242 µl) to give a red/brown suspension, that was heated for 90 minutes at 120° C. After the reaction, 10 mL of ice water was added, then extraction with 15 mL DCM 3 times, the extract was washed with an appropriate amount of water, dried over anhydrous sodium sulfate, and concentrated in vacuo. The residue was purified via Biotage Isolera One (100:0 to 95:5 DCM/MeOH; 10 g HP-Sil column) to give the desired product (22 mg, 78%).

1H NMR (400 MHz, DMSO-$d_6$) δ 8.88 (d, 1H), 8.75 (d, 1H), 8.65 (s, 1H), 8.19 (dd, 1H), 8.08 (t, 1H), 7.88 (d, 1H), 7.18 (s, 1H), 7.07 (d, 1H), 4.84 (d, 1H), 4.27-4.10 (m, 1H), 4.02 (d, 1H), 3.75 (dd, 1H), 2.05-1.85 (m, 2H), 1.79 (s, 1H), 1.60 (s, 1H)

MS (ESI); m/z=381.11 $[M+H]^+$

BIOLOGICAL ASSAY DESCRIPTION

Assay 1 (Fluorescence Based Assay):

Direct Staining of Compounds of this Invention to Human Parkinson's Disease Brain Sections 20 µm frozen sections from amygdala were purchased from an external provider (Tissue Solutions Ltd.). Donors were diagnosed with PD, Braak stage V-VI (Braak et al., Neurobiol. Aging, 2003, 24, 197-211) and thus with confirmed aSyn pathology. PD donors, Braak stage V-VI with mixed pathology, containing aSyn aggregates as well as Aβ plaques, were also used in this assay. Sections were kept at −80° C. until start of the experiment.

Brain sections were encircled with pap pen liquid blocker to reduce the volume of solution for the different incubations. Sections were fixed for 15 min at 4° C. with 4% paraformaldehyde and washed three times for 5 minutes with PBS (phosphate buffered saline) at room temperature. Test compounds were incubated on the sections at 100 µM in 50% ethanol in water for 30 min at room temperature, followed by three washes of 5 minutes with PBS. Sections were then saturated and permeabilized in blocking buffer (PBS, 10% NGS, 0.25% Triton) for 1 hour at room temperature and then incubated for 2 hours at room temperature with the primary antibodies against aSyn: aSyn-211 (SantaCruz Biotechnology sc-12767) or aSyn-pS129 (Abcam AB51253), and primary antibody against AR, 4G8, (Covance, SIG-39220). All primary antibodies diluted 1/250 in PBS, 5% NGS, 0.25% Triton. After three washes in PBS, the sections were incubated for 30 minutes at room temperature with a secondary anti-mouse antibody labeled with AlexaFluor555 (Invitrogen A21422) or anti-rabbit antibody labeled with AlexaFluor555 (Invitrogen A21428) and further washed three times in PBS. To reduce auto-fluorescence of the tissue, the sections were incubated in a solution of 0.1% Sudan Black (Sigma 199664) in 70% ethanol for 15 min at room temperature, followed by four washes with PBS and mounted under cover slips using ProLong Gold Antifade reagent (Invitrogen P36930).

Sections were analyzed on the Nikon Eclipse Ti microscope to detect staining and imaged using Nikon DS-Fi2 camera and NIS-Element AR4.13.1 software. Results from this assay are shown in Table 9.

Direct Staining of Compounds of this Invention to Human Alzheimer's Disease Brain Sections 20 µm frozen sections from amygdala were purchased from an external provider (Tissue Solutions Ltd.). Donors were diagnosed with AD, Braak stage V-VI (Braak et al., Neurobiol. Aging, 1995, 16, 271-284) and thus with confirmed Aβ pathology. Sections were kept at −80° C. until start of the experiment.

Brain sections were encircled with pap pen liquid blocker to reduce the volume of solution for the different incubations. Sections were fixed for 15 min at 4° C. with 4% paraformaldehyde and washed three times for 5 minutes with PBS at room temperature. Test compounds were incubated on the sections at 100 µM in 50% ethanol in water for 30 min at room temperature, followed by three washes of 5 minutes with PBS. Sections were then saturated and permeabilized in blocking buffer (PBS, 10% NGS, 0.25% Triton) for 1 hour at room temperature and then incubated for 2 hours at room temperature with the primary antibodies against AR, 4G8, (Covance, SIG-39220), diluted 1/250 in PBS, 5% NGS, and 0.25% Triton. After three washes in PBS, the sections were incubated for 30 minutes at room temperature with a secondary anti-mouse antibody labeled with AlexaFluor555 (Invitrogen A21422) and further washed three times in PBS. To reduce auto-fluorescence of the tissue, the sections were incubated in a solution of 0.1% Sudan Black (Sigma 199664) in 70% ethanol for 15 min at room temperature, followed by four washes with PBS and mounted under cover slips using ProLong Gold Antifade reagent (Invitrogen P36930).

Sections were analyzed on the Nikon Eclipse Ti microscope to detect staining and imaged using Nikon DS-Fi2 camera and NIS-Element AR4.13.1 software. Results from this assay are shown in Table 9.

TABLE 9

| | Assay 1 (Fluorescence based assay) | | |
|---|---|---|---|
| Example no. | Staining of aSyn aggregates on PD sections | Staining of Aβ plaques on AD sections | Staining of Aβ plaques on PD sections with mixed pathology |
| 10 | + | +++ | n.d. |
| 11 | + | ++ | n.d. |
| 12 | + | ++ | n.d. |
| 13 | ++ | +++ | n.d. |
| 59 | + | + | n.d. |
| 58 | + | ++ | n.d. |
| 14 | ++ | +++ | n.d. |
| 15 | +++ | +++ | n.d. |
| 63 | ++ | ++ | n.d. |
| 64 | + | +++ | n.d. |
| 16 | ++ | ++ | n.d. |
| 47 | +++ | +++ | n.d. |
| 77 | ++ | ++ | n.d. |
| 74 | + | +++ | n.d. |
| 75 | ++ | +++ | n.d. |
| 76 | + | +++ | n.d. |
| 29 | + | ++ | n.d. |
| 30 | ++ | ++ | n.d. |
| 31 | + | ++ | n.d. |
| 9 | ++ | ++ | n.d. |
| 56 | ++ | ++ | n.d. |
| 8 | ++ | +++ | n.d. |
| 32 | +++ | +++ | n.d. |
| 33 | +++ | + | n.d. |

TABLE 9-continued

| | Assay 1 (Fluorescence based assay) | | |
|---|---|---|---|
| Example no. | Staining of aSyn aggregates on PD sections | Staining of Aβ plaques on AD sections | Staining of Aβ plaques on PD sections with mixed pathology |
| 57 | ++ | + | n.d. |
| 65 | + | +++ | n.d. |
| 66 | + | ++ | n.d. |
| 45 | + | ++ | n.d. |
| 48 | ++ | + | n.d. |
| 18 | +++ | +++ | n.d. |
| 4 | +++ | + | n.d. |
| 5 | + | + | n.d. |
| 34 | ++ | +++ | n.d. |
| 49 | ++ | ++ | n.d. |
| 3 | ++ | ++ | n.d. |
| 35 | ++ | ++ | n.d. |
| 19 | +++ | +++ | n.d. |
| 6 | ++ | ++ | n.d. |
| 2 | ++ | ++ | n.d. |
| 7 | ++ | +++ | n.d. |
| 36 | +++ | +++ | n.d. |
| 37 | ++ | + | n.d. |
| 50 | ++ | + | n.d. |
| 69 | ++ | + | n.d. |
| 38 | +++ | +++ | n.d. |
| 39 | + | + | n.d. |
| 44 | + | – | n.d. |
| 67 | + | + | n.d. |
| 46 | + | + | n.d. |
| 40 | +++ | + | n.d. |
| 78 | + | + | n.d. |
| 20 | + | – | n.d. |
| 80 | +++ | ++ | n.d. |
| 28 | + | + | n.d. |
| 23 | ++ | + | n.d. |
| 24 | ++ | + | n.d. |
| 21 | ++ | ++ | n.d. |
| 51 | ++ | + | n.d. |
| 25 | ++ | + | n.d. |
| 79 | + | + | n.d. |
| 68 | + | – | n.d. |
| 42 | + | + | n.d. |
| 52 | + | – | n.d. |
| 53 | + | + | n.d. |
| 70 | + | + | n.d. |
| 71 | + | – | n.d. |
| 72 | +++ | + | n.d. |
| 73 | ++ | + | n.d. |
| 83 | +++ | n.d. | – |
| 85 | +++ | n.d. | – |
| 88 | +++ | n.d. | – |
| 89 | ++ | n.d. | – |
| 90 | ++ | n.d. | – |
| 91 | ++ | n.d. | – |
| 84 | ++ | n.d. | +/– |
| 86 | ++ | n.d. | – |
| 87 | ++ | n.d. | – |
| 123 | + | n.d. | + |
| 101 | ++ | n.d. | + |
| 100 | ++ | n.d. | ++ |
| 130 | ++ | n.d. | +++ |
| 129 | ++ | n.d. | +++ |
| 119 | + | n.d. | – |
| 118 | + | n.d. | + |
| 112 | + | n.d. | ++ |
| 113 | + | n.d. | ++ |
| 105 | +++ | n.d. | ++ |
| 106 | +++ | n.d. | +++ |
| 111 | +++ | n.d. | +++ |
| 114 | +++ | n.d. | +++ |
| 131 | ++ | n.d. | +++ |
| 94 | +++ | n.d. | – |
| 95 | ++ | n.d. | – |
| 108 | ++ | n.d. | +/– |
| 109 | ++ | n.d. | +/– |
| 96 | ++ | n.d. | +/– |
| 97 | + | n.d. | +/– |

TABLE 9-continued

| | Assay 1 (Fluorescence based assay) | | |
|---|---|---|---|
| Example no. | Staining of aSyn aggregates on PD sections | Staining of Aβ plaques on AD sections | Staining of Aβ plaques on PD sections with mixed pathology |
| 110 | + | n.d. | +++ |
| 132 | ++ | n.d. | +/– |
| 98 | + | n.d. | +/– |
| 99 | ++ | n.d. | +/– |
| 128 | ++ | n.d. | ++ |
| 125 | + | n.d. | + |
| 126 | ++ | ++ | n.d. |
| 127 | ++ | + | n.d. |
| 102 | +++ | +++ | n.d. |
| 103 | +++ | +++ | n.d. |
| 104 | +++ | ++ | n.d. |

Table Legend: Staining intensity of alpha-synuclein aggregates and Lewy bodies (PD sections) and Aβ plaques (AD sections and PD sections with mixed pathology): – (No); +/– (very weak); +++ (strong); ++ (good); + (weak); n.d.: not determined Assay 2 (Backscattering Interferometry):

Preparation of Total Brain Homogenates from Control and PD Brain Samples

Approximately 300 mg of cortex from control and PD donors (purchased from Tissue Solutions Ltd., diagnosed with PD Braak stage V-VI, or healthy age-matched donors) were weighed and homogenized on ice using a glass potter in 9× volume/weight of homogenization buffer: 25 mM Tris-HCl pH 7.4, 150 mM NaCl, 1 mM EDTA, 1 mM EGTA containing phosphatase inhibitors (30 mM NaF, 0.2 mM $Na_3VO_4$, 1 nM okadaic acid, 1 mM phenylmethylsulfonyl fluoride (PMSF), 5 mM $Na_4P_2O_7$) and protease inhibitor cocktail (Complete™, Roche). Samples were aliquoted and stored at −80° C.

Determination of Dissociation Constants ($K_d$) of Compounds of this Invention by Backscattering Interferometry Backscattering interferometry (BSI) measurements were performed by Molecular Sensing GmbH (Idstein, Germany). Examples of this invention at 10 mM in DMSO were diluted 1:100 in PBS and then diluted again in PBS to yield 2 μM concentration of compound in PBS with 0.02% DMSO. The refractive index of the assay buffer (PBS pH 7.4 containing 0.02% DMSO) and the compound were matched and then 2× serial dilutions of the compound were done in polypropylene dilution reservoirs. A thawed aliquot of control, AD and PD brain homogenates was diluted 1/150 in PBS, pH 7.4 and used immediately.

Examples of this invention and brain homogenates were mixed 1:1 in 96-well PCR microplates to a final volume of 60 μL and heat sealed with foil. The assays were allowed to incubate at room temperature for 45 minutes before being run on the BSI instrument. Wells were pierced individually prior to sample injection and measurement of BSI signal (each well analyzed in triplicate).

For each assay the reference curve (control brain homogenate) was subtracted from the assay curve point by point. The final data for the difference curve was exported to Graphpad Prism® software (GraphPad Software, La Jolla Calif. USA, www.graphpad.com) and fit with a one-site binding equation to determine a $K_d$ for the example compound. Examples of this invention were run to have at least two successful experiments with good reproducibility. Success was defined as having a binding signal with a $R^2$>0.7. The results of this assay are shown in Table 10.

TABLE 10

| Example no. | Assay 2 (Backscattering Interferometry) $K_d$ on PD brain homogenates (nM) |
|---|---|
| 47 | 14.8 |
| 32 | 7.9 |
| 39 | 36 |
| 44 | 9 |
| 40 | 14 |
| 69 | 15 |
| 78 | 26 |
| 50 | 35 |
| 80 | 36 |
| 67 | 44 |
| 20 | 50 |

The invention claimed is:

1. A compound of formula (IIa):

(IIa)

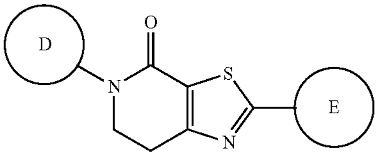

and all derivatives, stereoisomers, racemic mixtures, pharmaceutically acceptable salts, hydrates, solvates, prodrugs and polymorphs thereof;

wherein the compound can be optionally detectably labeled by replacing any atom at any position with a label, and wherein the label is a radionuclide, a positron emitter, or a gamma emitter;

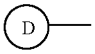

is selected from the group consisting of

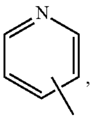, 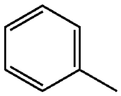, 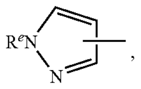, hydrogen and alkyl, wherein

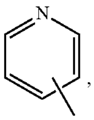, 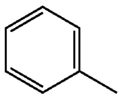, 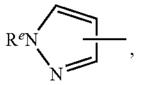, and alkyl can be attached at any available position, and wherein

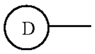

can be optionally substituted by one or more substituents $R^D$;

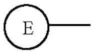

is

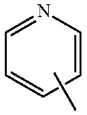, wherein

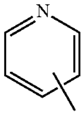

can be attached at any available position, and wherein

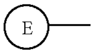

can be optionally substituted by one or more substituents $R^E$;

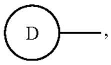, 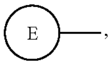, or both, can be optionally substituted by a leaving group (LG) at any available position, wherein the compound is capable of being detectably labeled upon replacement of the LG with a radionuclide, a positron emitter, or a gamma emitter;

for each occurrence, $R^d$ is independently selected from the group consisting of halogen, —OH, —O-alkyl and hydrogen;

for each occurrence, $R^e$ is independently selected from the group consisting of hydrogen, $—(CH_2CH_2—O)_n—R^f$, $—(CH_2CH_2—O)_n—(CH_2CH_2)—R^d$, alkyl, carbocyclyl and heterocyclyl, wherein alkyl, carbocyclyl and heterocyclyl can be optionally substituted, for each occurrence, $R^f$ is independently selected from the group consisting of hydrogen, and alkyl, wherein alkyl can be optionally substituted;

for each occurrence, $R^D$ is independently selected from the group consisting of halogen, CN, $—O—R^{10}$, $—NR^{10}R^{11}$, $—CONR^{10}R^{11}$, $—N(R^{10})—C(O)—R^{11}$, $—N(R^{10})—C(O)—O—R^{11}$, $—(O—CH_2CH_2)_n—R^d$, =O, alkyl, carbocyclyl, carbocyclylalkyl, heterocyclyl, heterocyclylalkyl, alkenyl, and alkynyl;

for each occurrence, $R^E$ is independently selected from the group consisting of halogen, CN, $—O—R^{10}$, $—NR^{10}R^{11}$, $—CONR^{10}R^{11}$, $—N(R^{10})—C(O)—R^{11}$, $—N(R^{10}—C(O)—O—R^{11}$, $—(O—CH_2CH_2)_n—R^d$, =O, alkyl, carbocyclyl, carbocyclylalkyl, heterocyclyl, heterocyclylalkyl, alkenyl, and alkynyl, wherein-alkyl, carbocyclyl, carbocyclylalkyl, heterocyclyl, heterocyclylalkyl, alkenyl, and alkynyl can be optionally substituted, or if more than one group $R^E$ is present and two of the groups $R^E$ are adjacent, they can optionally be taken together and can form a 5- to 8-membered ring containing carbon atoms and optionally one or more heteroatoms or one or more moieties comprising one or more heteroatoms, wherein the one or more heteroatoms are selected from O, S, or N and wherein the 5- to 8-membered ring may be substituted;

for each occurrence, $R^{10}$ is independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, $R^{11}$ is independently selected from the group consisting of: hydrogen, alkyl, carbocyclyl, carbocyclylalkyl, heterocyclyl, and heterocyclylalkyl, wherein alkyl, carbocyclyl, carbocyclylalkyl, heterocyclyl, and heterocyclylalkyl can be optionally substituted;

for each occurrence, n is independently 1 to 4.

2. The compound according to claim 1, wherein the LG is selected from nitro, halogen, trimethylammonium, C1-4 alkyl sulfonate, or C6-10 aryl sulfonate.

3. A diagnostic composition comprising a detectably labeled compound according to claim 1 and a pharmaceutically acceptable carrier, diluent, adjuvant and/or excipient.

4. A pharmaceutical composition comprising a compound according to claim 1 and a pharmaceutically acceptable carrier, diluent, adjuvant or excipient.

5. The compound according to claim 1, wherein

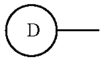

is

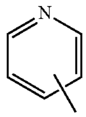

, which is optionally substituted by $R^D$.

6. The compound according to claim 1, wherein $R^E$ is independently selected from the group consisting of halogen, —CN, —O—$R^{10}$, —$NR^{10}R^{11}$, —$N(R^{10})$—C(O)—O—$R^{11}$, —$(O—CH_2CH_2)_n$—$R^d$, optionally substituted alkyl, and optionally substituted heterocyclyl.

7. The compound according to claim 1, wherein $R^E$ is independently selected from the group consisting of halogen and optionally substituted heterocyclyl.

8. The compound according to claim 1, wherein the compound is detectably labeled with $^{2}H$, $^{3}H$, $^{18}F$, $^{123}I$, $^{124}I$, $^{125}I$, $^{131}I$, $^{11}C$, $^{13}N$, $^{15}O$, or $^{77}Br$.

9. The compound according to claim 1, wherein the compound is detectably labeled with $^{18}F$.

10. A mixture comprising a detectably labeled compound as defined in claim 1 and at least one compound which is a beta or tau imaging agent and which is different from the detectably labeled compound as defined in claim 1.

* * * * *